US011649250B2

United States Patent
Dimasi et al.

(10) Patent No.: US 11,649,250 B2
(45) Date of Patent: May 16, 2023

(54) PYRROLOBENZODIAZEPINE CONJUGATES

(71) Applicant: MEDIMMUNE LIMITED, Cambridge (GB)

(72) Inventors: Nazzareno Dimasi, Gaithersburg, MD (US); Philip Wilson Howard, Cambridge (GB); Luke Masterson, Cambridge (GB); Arnaud Charles Tiberghien, Cambridge (GB); Balakumar Vijayakrishnan, Cambridge (GB); Jason White, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 107 days.

(21) Appl. No.: 16/639,667

(22) PCT Filed: Aug. 17, 2018

(86) PCT No.: PCT/EP2018/072298
§ 371 (c)(1),
(2) Date: Feb. 17, 2020

(87) PCT Pub. No.: WO2019/034764
PCT Pub. Date: Feb. 21, 2019

(65) Prior Publication Data
US 2020/0247823 A1    Aug. 6, 2020

Related U.S. Application Data

(60) Provisional application No. 62/547,303, filed on Aug. 18, 2017.

(51) Int. Cl.
| | | |
|---|---|---|
| *C07D 519/00* | (2006.01) | |
| *A61K 47/54* | (2017.01) | |
| *C07K 16/00* | (2006.01) | |
| *A61K 45/06* | (2006.01) | |

(52) U.S. Cl.
CPC .......... *C07D 519/00* (2013.01); *A61K 47/545* (2017.08); *C07K 16/00* (2013.01); *A61K 45/06* (2013.01); *C07K 2317/24* (2013.01); *C07K 2317/52* (2013.01); *C07K 2317/73* (2013.01)

(58) Field of Classification Search
CPC .................. C07D 519/00; C07K 16/00; C07K 2317/24; C07K 2317/52; C07K 2317/73; C07K 2317/53; C07K 16/32; Y02A 50/30; A61P 35/00; A61K 47/545; A61K 45/06; A61K 47/6855; A61K 2039/505; A61K 47/6851; A61K 47/6803
See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair et al., "Antibody-drug conjugates—a perfect synergy," Exp. Opin. Biol. Ther. (2012), pp. 1-16.

(Continued)

*Primary Examiner* — Julie Wu
*Assistant Examiner* — John L Van Druff
(74) *Attorney, Agent, or Firm* — Casimir Jones SC; Lisa Mueller

(57) ABSTRACT

A conjugate of formula (I) wherein Ab is a modified antibody having at least one free conjugation site on each heavy chain.

31 Claims, 4 Drawing Sheets
Specification includes a Sequence Listing.

(56) References Cited

U.S. PATENT DOCUMENTS

| | | |
|---|---|---|
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,561,119 A | 10/1996 | Jacquesy et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,321,774 B2 | 11/2012 | Barthal et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard et al. |
| 9,415,117 B2 | 8/2016 | Howard |
| 9,464,141 B2 | 10/2016 | Asundi et al. |
| 9,526,798 B2 | 12/2016 | Jeffrey et al. |
| 9,562,049 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard et al. |
| 9,889,207 B2 | 2/2018 | Howard |
| 9,956,298 B2 | 5/2018 | Howard et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0175775 A1 | 9/2003 | LePoul et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |

(56) References Cited

U.S. PATENT DOCUMENTS

| | | |
|---|---|---|
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | Mcdonagh et al. |
| 2009/0149449 A1 | 6/2009 | Liu et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0070227 A1 | 3/2011 | Novotney-Barry et al. |
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0121126 A1 | 5/2014 | Bivona et al. |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200055351 | 9/2000 |
| WO | WO 2000053216 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |

(56) References Cited

FOREIGN PATENT DOCUMENTS

| | | |
|---|---|---|
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |
| WO | WO 2007044515 | 4/2007 |
| WO | WO 2007085930 | 8/2007 |

(56) References Cited

FOREIGN PATENT DOCUMENTS

| | | |
|---|---|---|
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015112822 | 7/2015 |
| WO | WO 2015157595 | 10/2015 |
| WO | WO 2015159076 | 10/2015 |
| WO | WO 2016201065 | 12/2015 |
| WO | WO 2016037644 | 3/2016 |
| WO | WO 2016040868 | 3/2016 |
| WO | WO 2016044560 | 3/2016 |
| WO | WO 2016053107 | 4/2016 |
| WO | WO 2016166297 | 10/2016 |
| WO | WO 2016166298 | 10/2016 |
| WO | WO 2016166299 | 10/2016 |
| WO | WO 2016166300 | 10/2016 |
| WO | WO 2016166302 | 10/2016 |
| WO | WO 2016166305 | 10/2016 |
| WO | WO 2016166307 | 10/2016 |
| WO | WO-2017096163 A1 * 6/2017 .......... A61K 31/551 |  |
| WO | WO 2017137553 | 8/2017 |
| WO | WO 2017186894 | 11/2017 |
| WO | WO 2018031662 | 2/2018 |
| WO | WO 2020006722 | 1/2020 |

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird et al., "ABCB1 genetic polymorphism influences the pharmacology of the new pyrrolobenzodiazepine derivative SJG-136," Pharmacogenomics Journal (2008) 8(4):289-296.

Alley et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate CheM 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-lmmolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents. "J Med Chem. Apr. 8, 2010;53(7):2927-41.

Antonow, D. et al., "Synthesis of DNA-lnteractive Pyrrolo [2,1-c][1,4] benzodiazepines (PBDs)" Chemical Reviews, 2011, 111(4):2815-2864.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., "Molecular cloning of human endothelin receptors and their expressiOn in vascular endothelial cells and smooth muscle cells," Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chk1 and chk2 kinases in the cytotoxicity of SJG-136, a new pyrrolobenzodiazepine dimer," Proceedings of the American Asso-

(56) References Cited

OTHER PUBLICATIONS ciation for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non- inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J.M. et al., "Solid-phase synthesis of DNA-interactive pyrrolo[2,1-c][1,4]benzodiazepines," Tetrahedron Letters (2000) 41:6171-6174.
Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.
Bien & Balcerska, "Serum Soluble Interleukin 2 receptor in human cancer of adults and children: a review," Biomarkers, 2008, 13(1): 1-26.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006:26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chem. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chem. 274: 24335-24341.
Cho et al., "Structure of the extracellular region of HER2 alone and in complex with the Herceptin Fab," Nature 421, 756-760, 2003.
Ciccodicola, A., et al., "Molecular characterization of a gene of the 'EGF family' expressed in undifferentiated human NTERA2 teratocarcinoma cells," EMBO J. 8(7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer

(56) References Cited

OTHER PUBLICATIONS

SJG-136 (NSC694501)," Proceedings of the American Association for Cancer Research Annual Meeting (Jul. 2003) 44:524.

Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

Clinical Trial, "Translational research: 4 ways to fix the clinical trial." 2011, http://www.nature.com/news/2011/110928/full/477526a.html.

Clinical Trials Identifier NCT02034227, Safety, Tolerability Study of SG2000 in the Treatment of Advanced Chronic Lymphocytic Leukemia and Acute Myeloid Leukemia [online] NIH U.S. National Library of Medicine 2014 [Retrieved on Nov. 4, 2020], Retrieved from the Internet: <https://www.clinicaltrials.gov/ct2/show/NCT02034227>.

Collins, "Generation and initial analysis of more than 15,000 full-length human and mouse eDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey et al., "LuCap35: a new model of prostate cancer progression to androgen independence." The Prostate 2003;55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens L., et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use• of ATP bioluminescence as a measure of cell proliferation and cytotoxicity," (1993) J. Immunol. Meth. 160:81-88.

Dall'Acqua, W. F. et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2- d][1,4]benzodiazepin-6-one," J. Heterocyclic. Chem. (1980) 17:701-703.

Davis et al., "Identification of a family of Fe receptor homo logs with preferential B cell expression," (2001) Proc. Natl. Acad. Sci. USA 98(17):9772-9777.

De Groot, N.A., et al., "Cascade-Release Dendrimers" Liberate All End Groups upon a Single Triggering Event in the Dendritic Core, (2003) Angew. Chern. Int. Ed. 42:4490-4494.

De Groot et al., "Elongated Multiple Electronic Cascade and Cyclization Spacer Systems in Activatible Anticancer Prodrug for Enhanced Drug Release," (2001) J. Org. Chern. 66:8815-8830.

De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.

Dennis et al., (2002) "Albumin Binding As A General Strategy For Improving The Pharmacokinetics Of Proteins" J Biol Chem. 277:35035-35043.

Duke, P., et al., "Characterization of Type I Receptors for Transforming Growth Factor-beta and Activin," Science 264 (5155):101-104 (1994).

Dimasi et al., "Efficient preparation of site specific antibody drug conjugates using cysteine insertion," Mol. Pharmaceutics 14 1501-1516 (2017).

Dimasi et al., "The Design and Characterization of Oligospecific Antibodies for Simultaneous Targeting of Multiple Disease Mediators" Journal of Molecular Biology, 2009, 393, 672-692.

Dobner et al., "Differentiation-specific expression of a novel G protein-coupled receptor from Burkitt's lymphoma," (1992) Eur. J. Immunol. 22:2795-2799.

Dong, Q. et al., "Reductive cleavage of TROC groups under neutral conditions with cadmium-lead couple," Tetrahedron Lett. (1995) 36(32):5681-5682.

Dono et al., "Isolation and Characterization of the CRI PTO Autosomal Gene and Its X-linked Related Sequence," Am. J. Hum. Genet. 49:555-565, 1991.

Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.

Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech. (2003) 21:778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.

Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.

Dubowchik et al., "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.

Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.

Dumoutier L., et al., "Cutting Edge: STAT Activation By IL-19, IL-20 and mda-7 Through IL-20 Receptor Complexes of Two Types," J. Immunol. 167, 3545-3549, 2001.

Dupont, C. et al., "Synthesis of rhazinilam analogue acting as an inhibitor of tubulin assembly," Tetrahedron Lett. (2000) 41:5853-5856.

Ehsani A., et al., "Characterization of a New Allele of the Human ERBB2 Gene by Allele-Specific Competition Hybridization," (1993) Genomics 15, 426-429.

Eliel et al., Stereochemistry of Organic Compounds, John Wiley & Sons, Inc., New York (1994).

Elshourbagy N.A., et al., "Molecular Characterization and Regulation of the Human Endothelin Receptors," J. Biol. Chem. 268, 3873-3879, 1993.

Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.

Farmer, J.D. et al., "Synthesis and DNA crosslinking ability of a dimeric anthramycin analog," Tetrahedron Letters (1988) 29(40):5105-5108, Abstract only.

Farmer, J.D. et al., "DNA binding properties of a new class of linked anthramycin analogs,", Chemical Abstracts, Abstract No. 239940r, vol. 114, No. 25, 25 899-903 (1991).

Fey, T. et al., "Silica-supported TEMPO catalyst: synthesis and application in the anelli oxidation of alcohols," J. Org. Chem. (2001) 66:8154-8159.

(56) References Cited

OTHER PUBLICATIONS

Field, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.

Fields, G. and Noble, R. (1990) "Solid phase peptide synthesis utilizing 9-fluoroenylmethoxycarbonyl amino acids", Int. J. Peptide Protein Res. 35:161-214.

Firsching, A. et al., "Antiproliferative and angiostatic activity of suramin analogues," Cancer Res. (1995) 55:4957-4961.

Flanagan et al., "The ephrins and Eph receptors in neural development," Annu. Rev. Neurosci. 21:309-345 (1998).

Flygare, "Antibody-drug conjugates forthe treatment of cancer," Chem. Biol. & Drug Design (2013) 81 (1):113-121.

Flynn et al., "Pre-Clinical Activity of Adct-301, a Novel Pyrrolobenzodiazepine (PBD) Dimer-Containing Antibody Drug Conjugate (ADC) Targeting CD25-Expressing Hematological Malignancies," https://www.researchgate.net/publication/275520174.

Foloppe, M.P. et al., "DNA-binding properties of pyrrolo[2,1-c][1,4]benzodiazepine N10-C11 amidines," Eur. J. Med. Chem., 31, 407-410 (1996).

Fox et al., "cDNA cloning and tissue distribution of five human EPH-like receptor protein-tyrosine kinases," Oncogene 10 (5):897-905 (1995).

Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.

Fujisaku et al., "Genomic Organization and Polymorphisms of the Human C3d/Epstein-Barr Virus Receptor," (1989) J. Biol. Chem. 264 (4):2118-2125.

Fujisawa Pharmaceutical Co. Ltd., "Benzodiazepine derivatives," SciFinder Scholar, 2-3 (2002).

Fujisawa Pharmaceutical Co., Ltd., Abstract No. 139983k, "Benzodiazepine derivatives", Chemical Abstracts, vol. 99, No. 17, 603 (1983).

Fujisawa Pharmaceutical Co., Ltd., Abstract No. 72145x, "Benzodiazepine derivatives", Chemical Abstracts, vol. 98, No. 9, 638 (1983).

Fukuyama, T. et al., "Total Synthesis of (+)-Porothramycin B," Tetrahedron Letters, vol. 34, 16, 2577-2580 (1993).

Gallmeier, E., "Targeted disruption of FANCC and FANCG in human cancer provides a preclinical model for specific therapeutic options," Gastroenterology (2006) 130(7):2145-2154.

Gary S.C., et al., "cDNA cloning chromosomal localization, and expression analysis of human BEHAB/brevican, a brain specific proteoglycan regulated during cortical development and in glioma," Gene 256, 139-147, 2000.

Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.

Gavezzotti, A., "Are crystal structures predictable?" Acc. Chem. Res. (1994) 27:309-314.

Geiser et al. "Automation of solid-phase peptide synthesis" in Macromolecular Sequencing and Synthesis, Alan R. Liss, Inc., 1988, pp. 199-218.

Genbank accession No. 11038674 (2013).
Genbank accession No. 20 NM_006424 (2013).
Genbank accession No. AAH32229, version No. AAH32229.1 GI:21619004, record update: Mar. 6, 2012.
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. M76125, version No. M76125.1 GI:292869, 1995.
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).

Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.

Getz et al., "A Comparison between the Sulfhydryl Reductants Tris(2-carboxyethyl)phosphine and Dithiothreitol for Use in Protein Biochemistry," (1999) Anal. Biochem. vol 273:73-80.

Glynne-Jones et al., "TENB2, a proteogl yean identified in prostate cancerthat is associated with disease progression and androgen independence," (2001) Int J Cancer. Oct. 15; 94(2): 178-184.

Gordon et al., "Somatic hypermutation of the B cell receptor genes B29 (Igβ, CD79b) and mb1 (Igα, CD79a)," PNAS, Apr. 1, 2003, vol. 100, No. 7, 4126-4131.

Greene, T.W. and Wuts, P.G.M., Protective Groups in Organic Synthesis, John Wiley & Sons, 2nd ed Ch 7, 315-345 (1991).

Greene, T.W. et al., Protective Groups in Organic Synthesis, John Wiley & Sons (1999) 3rd Edition, 503-549.

Greene, T.W. et al., Protective Groups in Organic Synthesis, John Wiley & Sons (1999) 3rd Edition, 23-200.

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

(56) References Cited

OTHER PUBLICATIONS

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1- c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-lnteractive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro- N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Gu, Z. et al., "Prostate stem cell antigen (PSCA) expression increases with high gleason score, advanced stage and bone metastasis in prostate cancer," Oncogene 19, 1288-1296, 2000.
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1- c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *Streptomyces* sp.", J. Antibiotics, 41, 702-704 (1988).

Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross- linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1- c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1- c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the pyrrolo(1,4)benzodiazepines," Acc. Chem. Res., 19, 230-237 (1986).

(56) References Cited

OTHER PUBLICATIONS

Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion dated Dec. 21, 2012 for Int. Appl. No. PCT/US2012/059864 (7 pages).
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2013/071352 dated Feb. 5, 2014 (14 pages).
International Search Report and Written Opinion for Application No. PCT/EP2014/054958 dated Jul. 2, 2014 (13 pages).
International Search Report and Written Opinion for Application No. PCT/GB2015/052629 dated Nov. 2, 2015 (12 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
International Search Report and Written Opinion for Application No. PCT/EP2018/053163 dated Apr. 4, 2018, 10 pages.
International Search Report and Written Opinion for Application No. PCT/EP2018/053162 dated Apr. 24, 2018 (9 pages).
International Search Report and Written Opinion for Application No. PCT/EP2018/081079 dated Feb. 19, 2019 (12 pages).
Iontcho R Vlahov et al, "Preparation of pyrrolobenzodiazepine peptide conjugates for treating cancer diseases." WO2017172930, Oct. 5, 2017 pp. 1-6.
Itoh et al., "Sibanomicin, a new pyrrolo(1,4)benzodiazepine antitumor antibiotic produced by a *Micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "A Potent Anti-CD70 Antibody-Drug Conjugate Combining a Dimeric Pyrrolobenzodiazepine Drug with Site-Specific Conjugation Technology." Bioconj. Chem. 2013, 24, 1256-1263.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.

Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody—Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.
Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anti-cancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4]Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepine Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1680-1689.
Kasahara et al., "Nucleotide sequence of a chimpanzee DOB cDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor cDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).

(56) References Cited

OTHER PUBLICATIONS

Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman et al., "Phase I Trial of Recombinant Immunotoxin Anti-Tac(Fv)-PE38 (LMB-2) in Patients with Hematologic Malignancies," J. Clin. Oncol., 2000, 18:1622-1636.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kumar et al., "Antibody drug conjugates," Annual Reports in Medicinal Chemistry 2017, 50 441-480.
Kuminoto, et al., "Mazethramycin, a new member of anthramycin group antibiotics" J Antibiot (Tokyo) Jun. 1980; 33(6):665-7.
Kurebayashi et al., "Isolation and characterization of a new human breast cancer cell line, KPL-4, expressing the Erb B family receptors and interleukin 6," (1999) Brit. Jour. Cancer 79(5-6):707-717.
Lambert, "Drug-conjugated monoclonal antibodies for the treatment of cancer," (2005) Current Opin.In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+ -Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered FcγR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II Trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).

Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase:4-Methylene-L-, (E)- and (Z)-4-(Fluoromethylene)-L-, cis- and trans-5-Ethynyl-(±)-, and cis- and trans -5-Vinyl-L- proline," J. Org. Chem. 1992, 57, 2060-2065.
Marin, D., "Voltammetric studies of the interaction of pyrrolo[2,1-][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Masterson et al "Synthesis and biological evaluation of novel pyrrolo[2,1-c][1,4]benzodiazepine prodrugs for use in antibody-directed enzyme prodrug therapy.", Bioorganic & Medicinal Chemistry Letters, vol. 16., No. 2, Jan. 15, 2006, pp. 252-256.
Mastroberardino et al., "Amino-acid transport by heterodimers of 4F2hc/CD98 and members of a permease family," Nature 395 (6699):288-291 (1998).
Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS Is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.

(56) References Cited

OTHER PUBLICATIONS

Mungall A.J., et al., "The DNA sequence and analysis of human chromosome 6," Nature 425, 805-811, 2003.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New cDNA Clones from Brain Which Code for Large Proteins in vitro," (2000) DNA Res. 7 (2):143-150.
Nakamuta M., et al., "Cloning and sequence analysis of a cDNA encoding human non-selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudingerand Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Pei et al., "Exploration of Pyrrolobenzodiazepine (PBD)-Dimers Containing Disulfide-Based Prodrugs as Payloads for Antibody-Drug Conjugates." Mol Pharm. Sep. 4, 2018;15(9):3979-3996.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Purser, et al., "Fluorine in Medicinal Chemistry." Chem. Soc. Rev., 2008, 37, 320-330.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequencedependent intrastrand DNA cross- lins and monoalkylated adducts in addition to interstrand cross-links," J. Am. Chem. Soc., Sep. 2009, 131 (38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.

(56) References Cited

OTHER PUBLICATIONS

Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA For the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, THE DOBeta Gene is a Divergent Member of the Class II P Gene Family," (1987) J. Biol. Chem. 262:8759-8766.
Shamis et al., "Bioactivation of Self-lmmolative Dendritic Prodrugs by Catalytic Antibody 38C2," (2004) J . Am. Chem. Soc. 126:1726-1731.
Sharkey et al., "Epratuzumab-SN-38: a new antibody-drug conjugate forthe therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 2," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV/C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody—Multidrug Immunoconjugates," (2002) Bioorganic & Medicinal Chemistry Letters 12:2213-2215.
Sutherland et al., "SGN-CD33A: a novel CD33-targeting antibody-drug conjugate using a pyrrolobenzodiazepine dimer is active in models of drug-resistant AML." Blood 2013, 122:1455-1463.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Talpur et al., "CD25 Expression is Correlated with Histological Grade and Response to Denileukin Diftitox in Cutaneous T-Cell Lymphoma," J. Investigative Dermatology, 2006, 126:575-583.
Tawaragi Y., et al., "Primary Structure of Nonspecific Crossreacting Antigen (NCA), A Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E et al., "Effect of A-ring modifications on the DNA-binding behavior and cytotoxicity of pyrrolo[2,1-c][1,4]benzodiazepines", Journal of Medicinal Chemistry, 42:1951-1964 (1999).

(56) References Cited

OTHER PUBLICATIONS

Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien et al., "Design and Synthesis of Tesirine, a Clinical Antibody-Drug Conjugate Pyrrolobenzodiazepine Dimer Payload." ACS Med Chem Lett. Nov. 10, 2016; 7(11): 983-987.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
U.S. Appl. No. 62/547,303, filed Aug. 18, 2017.
Van Geel et al., "Chemoenzymatic Conjugation of Toxic Payloads to the Globally Conserved N-Glycan of Native mAbs Provides Homogeneous and Highly Efficacious Antibody-Drug Conjugates," (2015) Bioconjugate Chem. 26: 2233-2242.
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a human protein homologous to the mouse Lyb-2 B cell differentiation antigen and sequence of the corresponding cDNA," (1990) J. Immunol. 144(12):4870-4877.
Wakankar, et al., "Physicochemical stability of the antibody-drug conjugate Trastuzumab-DM1: changes due to modification and conjugation processes." Bioconjugate Chemistry, 2010, 21, 1588-1595.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody-drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na+-Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).

(56) References Cited

OTHER PUBLICATIONS

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 gene: complete edna sequence and its expression in b cells bearing membrane Ig of various isotypes," (1992) J. Immunol. 148(2) 633-637.

Zammarchi et al., "Pre-Clinical Development of Adct-402, a Novel Pyrrolobenzodiazepine (PBD)—Based Antibody Drug Conjugate (ADC) Targeting CD19-Expressing B-Cell Malignancies," Blood, 2015, 126:1564, Abstract.

Zhao et al., "Novel Antibody Therapeutics Targeting Mesothelin In Solid Tumors," (2016) Clin. Cancer Drugs 3: 76-86.

\* cited by examiner

Herceptin-Flexmab: Light Chain
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFI<u>C</u>PPSDEQLKSGTASVVCLLNNFYPREAKVQ
WKVDNALQSGNSQESVTEQDSKDSTYSLSSTLTLSKADYEKHKVYACE
VTHQGLSSPVTKSFNRGE<u>V</u>

Herceptin-Flexmab: Heavy Chain
EVQLVESGGGLVQPGGSLRLSCAASGFNIKDTYIHWVRQAPGKGLEW
VARIYPTNGYTRYADSVKGRFTISADTSKNTAYLQMNSLRAEDTAVYYC
SRWGGDGFYAMDYWGQGTLVTVSSASTKGPSVFP<u>C</u>APSSKSTSGGT
AALGCLVKDYFPEPVTVSWNSGALTSGVHTFPAVLQSSGLYSLSSVVT
VPSSSLGTQTYICNVNHKPSNTKVDKRVEPKS<u>V</u>DKTHT<u>C</u>PP<u>V</u>PAPELLG
GPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIE
KTISKAKGQPREPQVYTLPPSREEMTKNQVSLTCLVGFYPSDIAVEWE
SNGQPENNYKTTPPVLDSDGSFFLYSKLTVDKSRWQQGNVFSCSVMH
EALHNHYTQKSLSLSPGK

Fig. 5

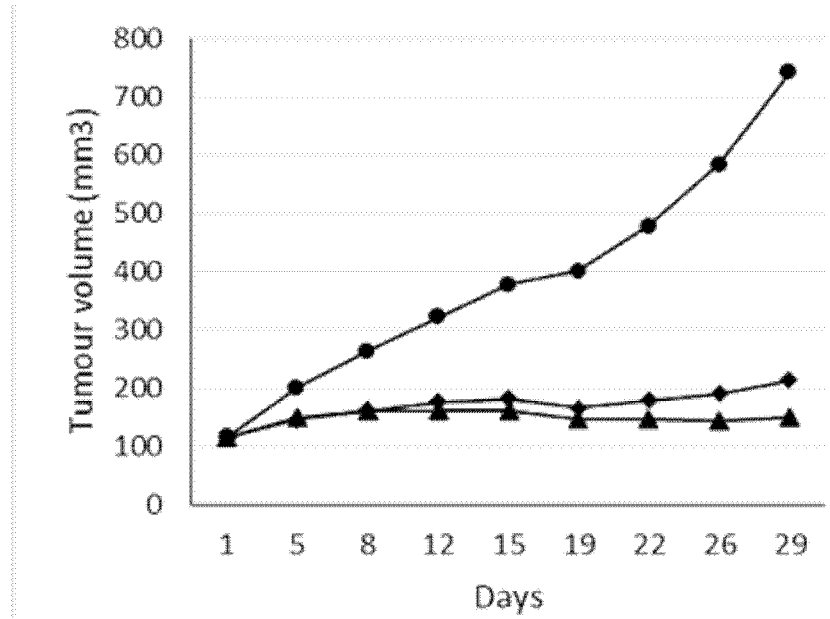

Fig. 6

PYRROLOBENZODIAZEPINE CONJUGATES

CROSS-REFERENCE TO RELATED APPLICATIONS

This application is a national phase application under 35 U.S.C. § 371 of PCT International Application No. PCT/EP2018/072298, filed Aug. 17, 2018, which claims the benefit of U.S. Provisional Patent Application No. 62/547,303, filed Aug. 18, 2017, each of which is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,431 Byte ASCII (Text) file named "38820-252_SQL_ST25.TXT," created on Feb. 22, 2022.

The present invention relates to conjugates comprising pyrrolobenzodiazepines and related dimers (PBDs), and the precursor drug linkers used to make such conjugates.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

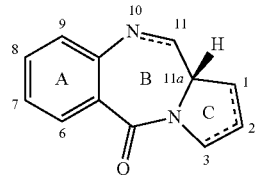

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

It has been previously disclosed that the biological activity of this molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

One example of a PBD dimer is SG2000 (SJG-136):

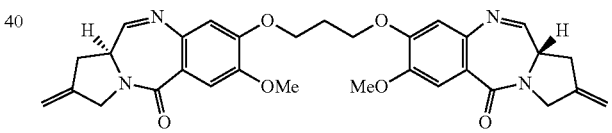

(Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)) which has been involved in clinical trials as a standalone agent, for example, NCT02034227 investigating its use in treating Acute Myeloid Leukemia and Chronic Lymphocytic Leukemia (see: https://www.clinicaltrials.gov/ct2/show/NCT02034227).

Dimeric PBD compounds bearing C2 aryl substituents, such as SG2202 (ZC-207), are disclosed in WO 2005/085251:

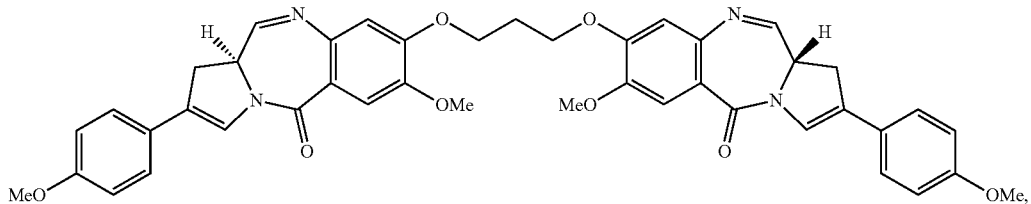

ZC-207 and in WO2006/111759, bisulphites of such PBD compounds, for example SG2285 (ZC-423):

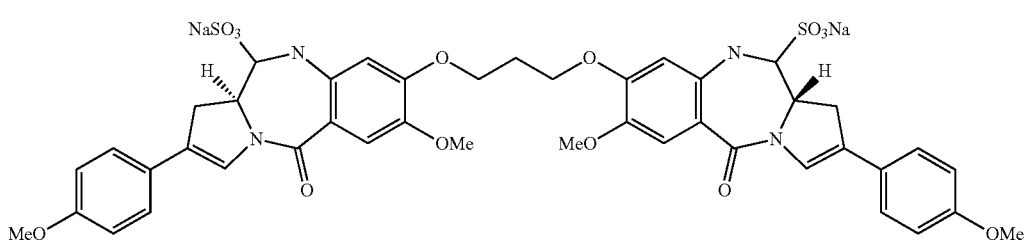

ZC-423

These compounds have been shown to be highly useful cytotoxic agents (Howard, P. W., et al., *Bioorg. Med. Chem.* (2009), doi: 10.1016/j.bmcl.2009.09.012).

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, are described in WO 2011/130598. The linker in these compounds is attached to one of the available N10 positions, and are generally cleaved by action of an enzyme on the linker group. If the non-bound N10 position is protected with a capping group, the capping groups exemplified have the same cleavage trigger as the linker to the antibody.

WO 2014/057074 describes two specific PBD dimer conjugates bound via the N10 position on one monomer, the other PBD monomer being in imine form. One of the drug-linkers disclosed is SG3249, Tesirine:

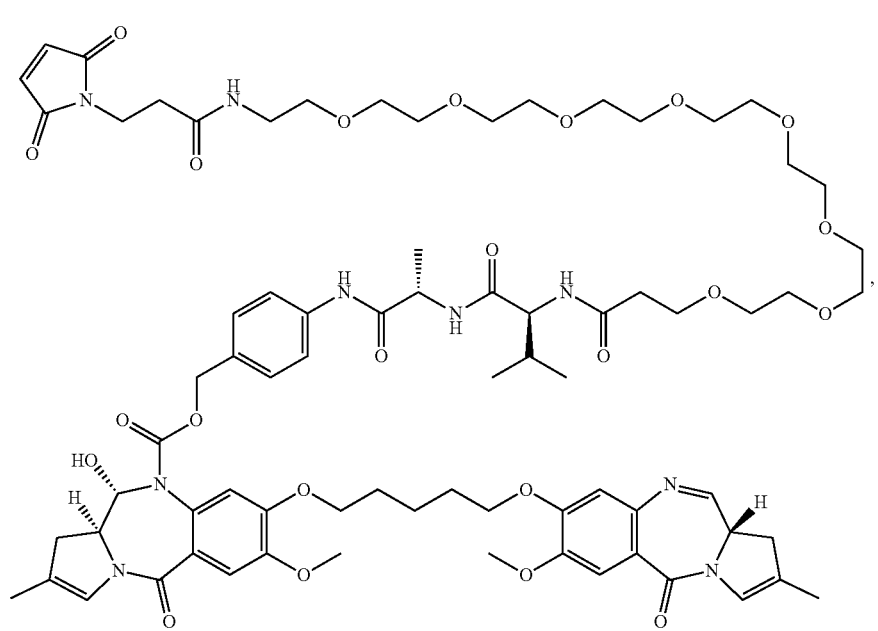

SG3249

Tesirine which, when conjugated to anti-DLL3 rovalpituzumab, is know as rovalpituzumab-tesirine (Rova-T), currently under evaluation for the treatment of small cell lung cancer (Tiberghien, A. C., et al., *ACS Med. Chem. Lett.*, 2016, 7 (11), 983-987; DOI: 10.1021/acsmedchemlett.6b00062). Further conjugates of this drug-linker with an engineered version of tratuzumab and a humanized antibody against human CD19 also began trials in early 2017 by ADC Therapeutics SA (Abstracts #51 and #52 in Proceedings of the American Association for Cancer Research, Volume 58, April 2017).

WO 2015/052322 describes a specific PBD dimer conjugate bound via the N10 position on one monomer, the other PBD monomer being in imine form. It also describes a specific PBD dimer conjugate bound via the N10 position on one monomer, the other PBD monomer having a capping group with the same cleavage trigger as the linker to the antibody:

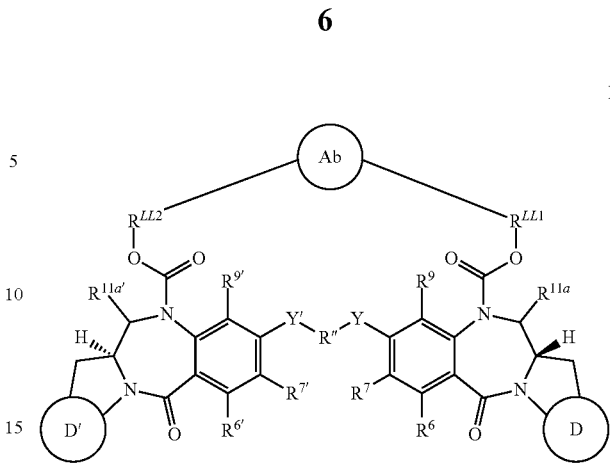

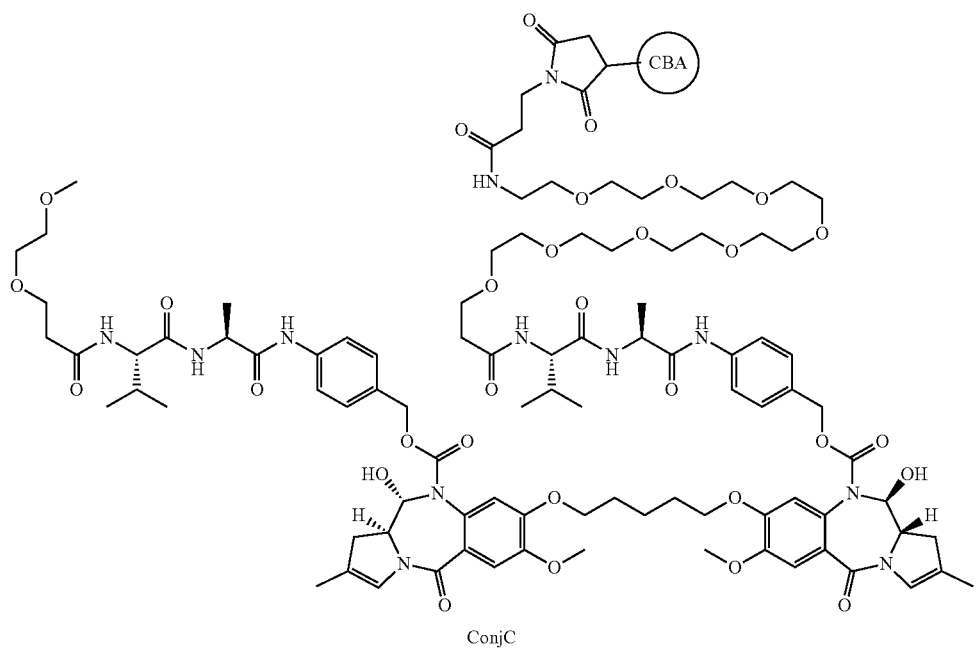 [SMILES: COCCOCCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4[C@H](O)N5C(=O)OCc4ccc(NC(=O)[C@H](C)NC(=O)[C@@H](NC(=O)CCOCCOCCOCCOCCOCCOCCOCCOCCNC(=O)CCN5C(=O)CC(C)C5=O)C(C)C)cc4)c(OC)cc3C(=O)N3C=C(C)C[C@H]3[C@@H]2O)cc1)C(C)C]

ConjC

DISCLOSURE OF THE INVENTION

The present invention provides PBDs, and related PBD dimer conjugates wherein the PBDs are conjugated to antibodies that are modified so as to have at least one free conjugation site on each heavy chain, and where the conjugation is via each N10 group of the PBD via a linker.

The present inventors have found such conjugates to be surprisingly effective, despite the expectation that it was not possible to link a single PBD or related dimer to a single antibody by two linkers.

The present invention also provided PBD and related dimer drug linkers, suitable for conjugating to a modified antibodies, where both N10 groups bear linking groups.

A first aspect of the present invention provides a conjugate of formula I:

Wherein

Ab is a modified antibody having at least one free conjugation site on each heavy chain;

D represents either group D1 or D2:

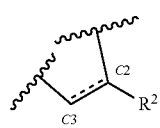

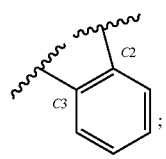

the dotted line indicates the optional presence of a double bond between C2 and C3; when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

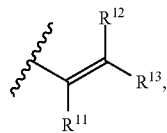

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

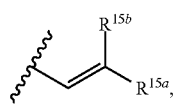

wherein one of $R^{15a}$ and $R^{15b}$ is H and the other is selected from: phenyl, which phenyl is optionally substituted by a group selected from halo, methyl, methoxy; pyridyl; and thiophenyl; and (if)

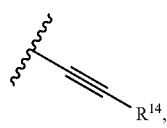

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is selected from H, OH, F, diF and

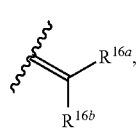

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

D' represents either group D'1 or D'2:

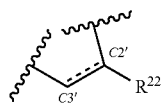

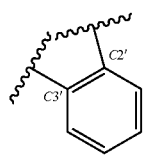

wherein the dotted line indicates the optional presence of a double bond between C2' and C3';

when there is a double bond present between C2' and C3', $R^{12}$ is selected from the group consisting of:

(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(iib) $C_{1-5}$ saturated aliphatic alkyl;

(iic) $C_{3-6}$ saturated cycloalkyl;

(iid)

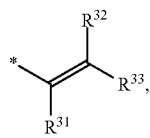

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(iie)

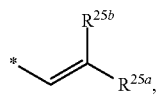

wherein one of $R^{25a}$ and $R^{25b}$ is H and the other is selected from: phenyl, which phenyl is optionally substituted by a group selected from halo, methyl, methoxy; pyridyl; and thiophenyl; and (iif)

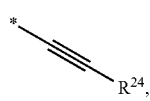

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is selected from H, OH, F, diF and

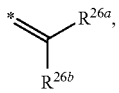

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NRR', nitro, $Me_3Sn$ and halo;
R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;
Y and Y' are selected from O, S, or NH;
$R^{11a}$ is selected from OH, $OR^4$, where $R^4$ is $C_{1-4}$ alkyl;
$R^{6'}$, $R^{7'}$, $R^{9'}$ and $R^{11a'}$ are selected from the same groups as $R^6$, $R^7$, $R^9$ and $R^{11a}$ respectively;
and
$R^{LL1}$ and $R^{LL2}$ are linkers connected to the antibody at different sites which are independently selected from:
(iiia):

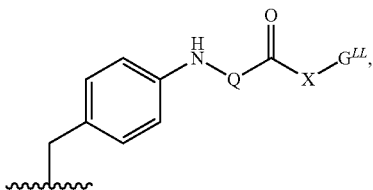

IIIa' wherein
Q is:

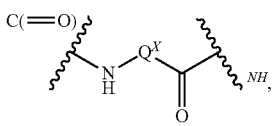

where $Q^X$ is such that Q is an amino-acid residue, a dipeptide residue or a tripeptide residue;
X is:

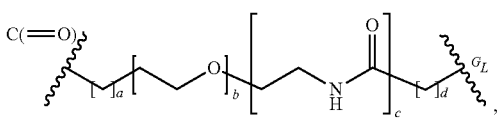

where a=0 to 5, b=0 to 16, c=0 or 1, d=0 to 5;
$G^{LL}$ is a linker connected to the antibody; and
(iiib):

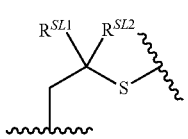

IIIb' where $R^{SL1}$ and $R^{SL2}$ are independently selected from H and methyl, or together with the carbon atom to which they are bound form a cyclopropylene or cyclobutylene group.

It is thought that such ADCs which effectively have a drug antibody ratio (DAR) of 1 could offer significant advantages including reduced off-target toxicity and an enhanced therapeutic window by reducing the minimal effective dose requirement over ADCs consisting of heterogeneous mixtures with higher DARs.

A second aspect of the present invention comprises a compound with the formula II:

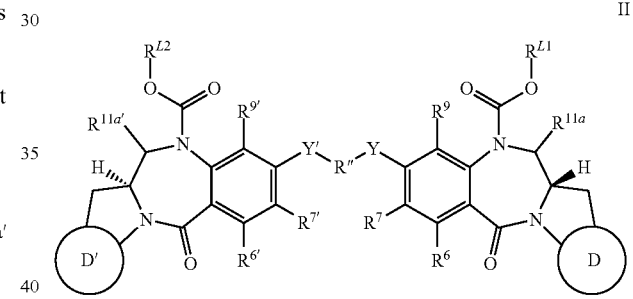

II and salts and solvates thereof,
wherein D, $R^2$, $R^6$, $R^7$, $R^9$, $R^{11a}$, Y, R", Y', D', $R^{6'}$, $R^{7'}$, $R^{9'}$, $R^{11a'}$ and $R^{12}$ (including the presence or absence of double bonds between C2 and C3 and C2' and C3' respectively) are as defined in the first aspect of the invention;
$R^L$ is a linker for connecting to a cell binding agent, which is selected from:
(iiia):

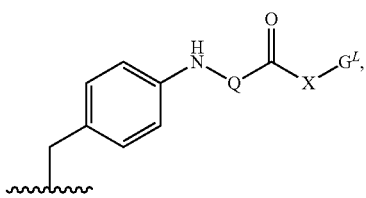

IIIa where Q and X are as defined in the first aspect and $G^L$ is a linker for connecting to an antibody; and
(iiib):

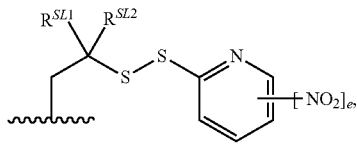

where $R^{SL1}$ and $R^{SL2}$ are as defined in the first aspect and e is 0 or 1.

A third aspect of the present invention provides the use of a conjugate of the first aspect of the invention in the manufacture of a medicament for treating a proliferative disease. The third aspect also provides a conjugate of the first aspect of the invention for use in the treatment of a proliferative disease. The third aspect also provides a method of treating a proliferative disease comprising administering a therapeutically effective amount of a conjugate of the first aspect of the invention to a patient in need thereof.

One of ordinary skill in the art is readily able to determine whether or not a candidate conjugate treats a proliferative condition for any particular cell type. For example, assays which may conveniently be used to assess the activity offered by a particular compound are described in the examples below.

A fourth aspect of the present invention provides the synthesis of a conjugate of the first aspect of the invention comprising conjugating a compound (drug linker) of the second aspect of the invention with an antibody as defined in the first aspect of the invention.

BRIEF DESCRIPTION OF FIGURES

FIG. 5 shows the heavy and light chain sequences of a Herceptin-Flexmab.

FIG. 6 shows the activity of a conjugate of the present invention compared to a conjugate not of the present invention.

DEFINITIONS

Substituents

Figure 1:
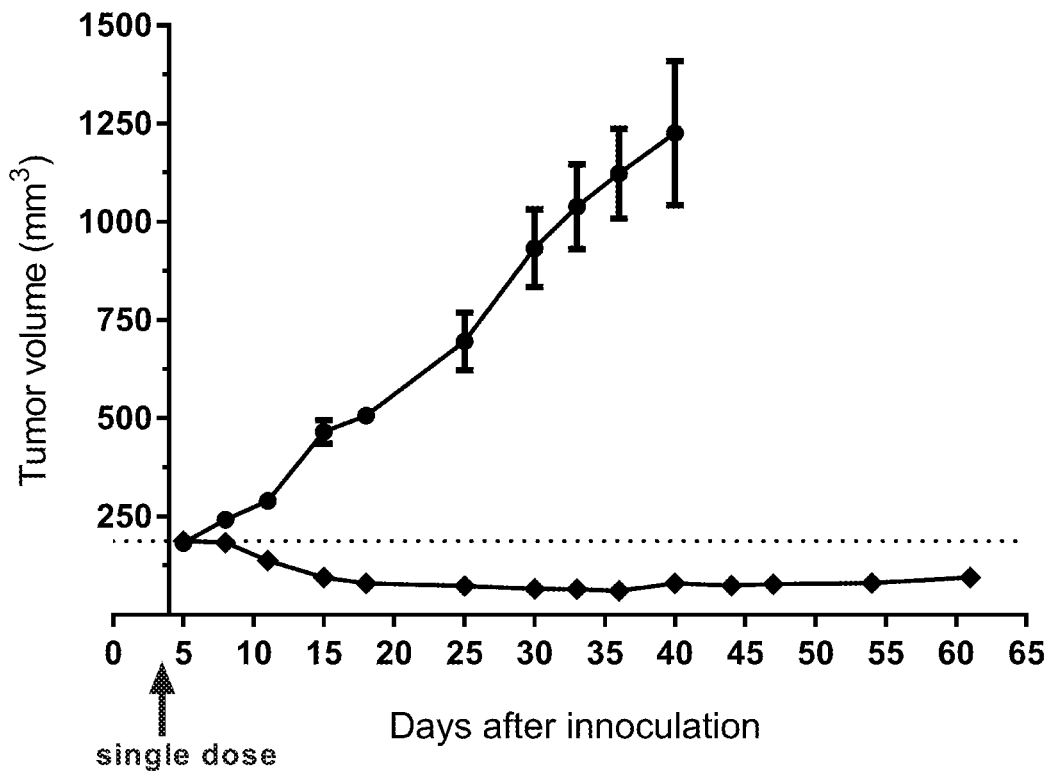
FIG. 1 shows the effect of a single dose of a conjugate of the invention compared to non-treatment in a NCI-N87 xenograft model.

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl (C7).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane ($C_3$), cyclobutane ($C_4$), cyclopentane ($C_5$), cyclohexane ($C_6$), cycloheptane (C7), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane (C7) and methylcyclohexane (C7);
unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene (C7) and methylcyclohexene (C7); and
saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:
$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);
$C_{11}$ (with 2 fused rings) derived from benzodiazepine ($N_2$);
$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and,
$C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.
Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_5$-20 aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

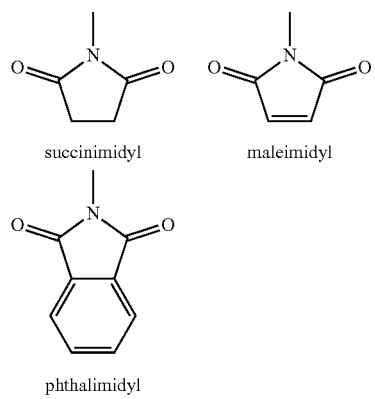

succinimidyl   maleimidyl phthalimidyl

Aminocarbonyloxy: —OC(=O)NR¹R², wherein R¹ and R² are independently amino substituents, as defined for amino groups. Examples of aminocarbonyloxy groups include, but are not limited to, —OC(=O)NH₂, —OC(=O)NHMe, —OC(=O)NMe₂, and —OC(=O)NEt₂.

Ureido: —N(R¹)CONR²R³ wherein R² and R³ are independently amino substituents, as defined for amino groups, and R¹ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom,

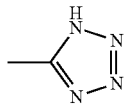

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH₂, —C(=NH)NMe₂, and —C(=NMe)NMe₂.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂C4F₉ (nonaflyl), —S(=O)₂CH₂CF₃ (tresyl), —S(=O)₂CH₂CH₂NH₂ (tauryl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO₂H.

Sulfonic acid (sulfo): —S(=O)₂OH, —SO₃H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH₃ (methoxysulfinyl; methyl sulfinate) and —S(=O)OCH₂CH₃ (ethoxysulfinyl; ethyl sulfinate).

Sulfonate (sulfonic acid ester): —S(=O)₂OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)₂OCH₃ (methoxysulfonyl; methyl sulfonate) and —S(=O)₂OCH₂CH₃ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH₃ and —OS(=O)CH₂CH₃.

Sulfonyloxy: —OS(=O)₂R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)₂CH₃ (mesylate) and —OS(=O)₂CH₂CH₃ (esylate).

Sulfate: —OS(=O)₂OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)₂OCH₃ and —SO(=O)₂OCH₂CH₃.

Sulfamyl (sulfamoyl; sulfinic acid amide; sulfinamide): —S(=O)NR¹R², wherein R¹ and R² are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamido (sulfinamoyl; sulfonic acid amide; sulfonamide): —S(=O)₂NR¹R², wherein R¹ and R² are independently amino substituents, as defined for amino groups. Examples of sulfonamido groups include, but are not limited to, —S(=O)₂NH₂, —S(=O)₂NH(CH₃), —S(=O)₂N(CH₃)₂, —S(=O)₂NH(CH₂CH₃), —S(=O)₂N(CH₂CH₃)₂, and —S(=O)₂NHPh.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_5$-20 aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR¹)—NR²$_2$, where R¹ and R² are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR¹)—NR²², where R¹ and R² are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$—CH$_2$CH$_2$CH$_2$— (heptylene).

Examples of branched saturated $C_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{3-12}$ alkylene groups ($C_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Ligand Unit

The Ligand Units for use in the present invention are Cell Binding Agents, more specifically modified antibodies, or antigen binding fragments thereof, having at least one conjugation site on each heavy chain. Examples of particular modified antibodies suitable for use according to the present invention are disclosed in WO 2012/064733 (filed as PCT/US2011/059775), which is incorporated herein by reference.

Antibodies

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include F(ab')$_2$, and scFv fragments, and dimeric epitope-binding fragments of any of the above which immunospecifically bind to cancer cell antigens, viral antigens or microbial antigens, single-chain antibody molecules; and multispecific antibodies formed from antibody fragments.

Modified antibodies suitable for use in the present invention include those wherein the native interchain cysteine residues have been substituted for amino acid residues lacking thiol groups. The antibodies may comprise at least one additional substitutions in each heavy chain of an amino acid residue comprising a reactive group suitable for conjugation to a linker. The additionally substituted amino acid may be a cysteine or a non-natural amino acid. The position that is substituted may be selected from those set forth below:

| Antibody | Isotype | IgG1 | IgG2 | IgG3 | IgG4 |
|---|---|---|---|---|---|
| Position | 239 | Ser | Ser | Ser | Ser |
| (Kabat | 282 | Val | Val | Val | Val |
| EU) and | 289 | Thr | Thr | Thr | Thr |
| Corre- | 297 | Asn | Asn | Asn | Asn |
| sponding | 312 | Asp | Asp | Asp | Asp |
| Amino | 324 | Ser | Ser | Ser | Ser |
| Acid | 330 | Ala | Ala | Ala | Ser |
|  | 335 | Thr | Thr | Thr | Thr |
|  | 337 | Ser | Ser | Ser | Ser |
|  | 339 | Ala | Thr | Thr | Ala |
|  | 356 | Glu | Glu | Glu | Glu |
|  | 359 | Thr | Thr | Thr | Thr |
|  | 361 | Asn | Asn | Asn | Asn |
|  | 383 | Ser | Ser | Ser | Ser |
|  | 384 | Asn | Asn | Ser | Asn |
|  | 398 | Leu | Leu | Leu | Leu |
|  | 400 | Ser | Ser | Ser | Ser |
|  | 422 | Val | Val | Ile | Val |
|  | 440 | Ser | Ser | Ser | Ser |
|  | 442 | Ser | Ser | Ser | Ser |

Examples of modified antibodies suitable for use in the present invention include the Flexmab structures disclosed in WO 2012/064733, which is incorporated herein. Such Flexmabs have cysteines with free thiol groups in the hinge region of the antibody that may be used as conjugation sites for linking through the N10 groups of the PBDs of the present invention.

Other examples of modified antibodies suitable for use in the present invention include those where cysteines have been inserted in selected sites in antibodies. These are described in Dimasi, N., et al., Molecular Pharmaceutics, 2017, 14, 1501-1516 (DOI: 10.1021/acs.molpharmaceut.6b00995) and WO2015/157595. In particular, antibodies which have been modified by insertion of a cysteine after the S239 position (ie. between positions 239 and 240) are of use.

Reference is made to the listed on pages 60 to 62 of WO 2012/064733, which is incorporated herein. In some embodiments, the antibody may be to a tumour-associated antigen, for example: HER2 (ErbB2); EPHA2 (EPH receptor A2); CD19; IL2RA (Interleukin 2 receptor, alpha).

Tumour-associate antigens and cognate antibodies for use in embodiments of the present invention are listed below, and are described in more detail on pages 14 to 86 of WO 2017/186894, which is incorporated herein.

(1) BMPR1B (bone morphogenetic protein receptor-type IB)
(2) E16 (LAT1, SLC7A5)
(3) STEAP1 (six transmembrane epithelial antigen of prostate)
(4) 0772P (CA125, MUC16)
(5) MPF (MPF, MSLN, SMR, megakaryocyte potentiating factor, mesothelin)
(6) Napi3b (NAPI-3B, NPTIIb, SLC34A2, solute carrier family 34 (sodium phosphate), member 2, type II sodium-dependent phosphate transporter 3b)
(7) Sema 5b (FLJ10372, KIAA1445, Mm.42015, SEMA5B, SEMAG, Semaphorin 5b Hlog, 25 sema domain, seven thrombospondin repeats (type 1 and type 1-like), transmembrane domain (TM) and short cytoplasmic domain, (semaphorin) 5B)
(8) PSCA hlg (2700050C12Rik, C530008016Rik, RIKEN cDNA 2700050C12, RIKEN cDNA 2700050C12 gene)
(9) ETBR (Endothelin type B receptor)
(10) MSG783 (RNF124, hypothetical protein FLJ20315)
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein)
(12) TrpM4 (BR22450, FLJ20041, TRPM4, TRPM4B, transient receptor potential cation 5 channel, subfamily M, member 4)
(13) CRIPTO (CR, CR1, CRGF, CRIPTO, TDGF1, teratocarcinoma-derived growth factor)
(14) CD21 (CR2 (Complement receptor 2) or C3DR (C3d/Epstein Barr virus receptor) or Hs.73792)
(15) CD79b (CD79β, CD79p, IGb (immunoglobulin-associated beta), B29)
(16) FcRH2 (IFGP4, IRTA4, SPAP1A (SH2 domain containing phosphatase anchor protein 1a), SPAP1B, SPAP1C)
(17) HER2 (ErbB2)
(18) NCA (CEACAM6)
(19) MDP (DPEP1)
(20) IL20R-alpha (IL20Ra, ZCYTOR7)
(21) Brevican (BCAN, BEHAB)
(22) EphB2R (DRT, ERK, Hek5, EPHT3, Tyro5)
(23) ASLG659 (B7h)
(24) PSCA (Prostate stem cell antigen precursor)
(25) GEDA
(26) BAFF-R (B cell-activating factor receptor, BLyS receptor 3, BR3)
(27) CD22 (B-cell receptor CD22-B isoform, BL-CAM, Lyb-8, Lyb8, SIGLEC-2, FLJ22814)
(27a) CD22 (CD22 molecule)
(28) CD79a (CD79A, CD79alpha), immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2).
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3,

(30) HLA-DOB (Beta subunit of MHC class II molecule (Ia antigen) that binds peptides and 20 presents them to CD4+T lymphocytes); 273 aa, pI: 6.56, MW: 30820.TM: 1 [P] Gene Chromosome: 6p21.3)

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3).

(32) CD72 (B-cell differentiation antigen CD72, Lyb-2); 359 aa, pI: 8.66, MW: 40225, TM: 1 5 [P] Gene Chromosome: 9p13.3).

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21)

(36) TENB2 (TMEFF2, tomoregulin, TPEF, HPP1, TR, putative transmembrane proteoglycan, related to the EGF/heregulin family of growth factors and follistatin); 374 aa)

(37) PSMA-FOLH1 (Folate hydrolase (prostate-specific membrane antigen) 1)

(38) SST (Somatostatin Receptor; note that there are 5 subtypes)
(38.1) SSTR2 (Somatostatin receptor 2)
(38.2) SSTR5 (Somatostatin receptor 5)
(38.3) SSTR1
(38.4) SSTR3
(38.5) SSTR4
AvB6—Both subunits (39+40)
(39) ITGAV (Integrin, alpha V)
(40) ITGB6 (Integrin, beta 6)
(41) CEACAM5 (Carcinoembryonic antigen-related cell adhesion molecule 5)
(42) MET (met proto-oncogene; hepatocyte growth factor receptor)
(43) MUC1 (Mucin 1, cell surface associated)
(44) CA9 (Carbonic anhydrase IX)
(45) EGFRvIII (Epidermal growth factor receptor (EGFR), transcript variant 3,
(46) CD33 (CD33 molecule)
(47) CD19 (CD19 molecule)
(48) IL2RA (Interleukin 2 receptor, alpha); NCBI Reference Sequence: NM_000417.2);
(49) AXL (AXL receptor tyrosine kinase)
(50) CD30-TNFRSF8 (Tumor necrosis factor receptor superfamily, member 8)
(51) BCMA (B-cell maturation antigen)-TNFRSF17 (Tumor necrosis factor receptor superfamily, member 17)
(52) CT Ags-CTA (Cancer Testis Antigens)
(53) CD174 (Lewis Y)-FUT3 (fucosyltransferase 3 (galactoside 3(4)-L-fucosyltransferase, Lewis blood group)
(54) CLEC14A (C-type lectin domain family 14, member A; Genbank accession no. NM175060)
(55) GRP78-HSPA5 (heat shock 70 kDa protein 5 (glucose-regulated protein, 78 kDa)
(56) CD70 (CD70 molecule) L08096
(57) Stem Cell specific antigens. For example:
5T4 (see entry (63) below)
CD25 (see entry (48) above)
CD32
LGR5/GPR49
Prominin/CD133
(58) ASG-5
(59) ENPP3 (Ectonucleotide pyrophosphatase/phosphodiesterase 3)
(60) PRR4 (Proline rich 4 (lacrimal))
(61) GCC-GUCY2C (guanylate cyclase 2C (heat stable enterotoxin receptor)
(62) Liv-1-SLC39A6 (Solute carrier family 39 (zinc transporter), member 6)
(63) 5T4, Trophoblast glycoprotein, TPBG-TPBG (trophoblast glycoprotein)
(64) CD56-NCMA1 (Neural cell adhesion molecule 1)
(65) CanAg (Tumor associated antigen CA242)
(66) FOLR1 (Folate Receptor 1)
(67) GPNMB (Glycoprotein (transmembrane) nmb)
(68) TIM-1-HAVCR1 (Hepatitis A virus cellular receptor 1)
(69) RG-1/Prostate tumor target Mindin-Mindin/RG-1
(70) B7-H4-VTCN1 (V-set domain containing T cell activation inhibitor 1
(71) PTK7 (PTK7 protein tyrosine kinase 7)
(72) CD37 (CD37 molecule)
(73) CD138-SDC1 (syndecan 1)
(74) CD74 (CD74 molecule, major histocompatibility complex, class II invariant chain)
(75) Claudins-CLs (Claudins)
(76) EGFR (Epidermal growth factor receptor)
(77) Her3 (ErbB3)-ERBB3 (v-erb-b2 erythroblastic leukemia viral oncogene homolog 3 (avian))
(78) RON-MST1R (macrophage stimulating 1 receptor (c-met-related tyrosine kinase))
(79) EPHA2 (EPH receptor A2)
(80) CD20-MS4A1 (membrane-spanning 4-domains, subfamily A, member 1)
(81) Tenascin C-TNC (Tenascin C)
(82) FAP (Fibroblast activation protein, alpha)
(83) DKK-1 (Dickkopf 1 homolog (*Xenopus laevis*))
(84) CD52 (CD52 molecule)
(85) CS1-SLAMF7 (SLAM family member 7)
(86) Endoglin-ENG (Endoglin)
(87) Annexin A1-ANXA1 (Annexin A1)
(88) V-CAM (CD106)-VCAM1 (Vascular cell adhesion molecule 1)

Connection of Linker Unit to Ligand Unit

The Ligand unit may be connected to the Linker unit through a disulfide bond.

In one embodiment, the connection between the Ligand unit and the Drug Linker is formed between a thiol group of a cysteine residue of the Ligand unit and a maleimide group of the Drug Linker unit. Other possible groups for linking, and the resulting linking groups, are shown below.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds.

These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008/070593, which are incorporated herein.

Methods of Treatment

The compounds of the present invention may be used in a method of therapy. Also provided is a method of treatment, comprising administering to a subject in need of treatment a therapeutically-effective amount of a conjugate of formula I. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a conjugate of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Drug Loading

The drug loading (p) is the average number of PBD drugs per cell binding agent, e.g. antibody. In the present invention, this is always 1. However, any composition may comprise antibodies where a PBD is conjugated and antibodies where a PBD is not conjugated. Thus for a composition, the drug loading (or DAR) may be less than 1, for example 0.75 and higher, 0.80 and higher, 0.85 and higher, 0.90 and higher or 0.95 or higher.

General Synthetic Routes

The synthesis of PBD compounds is extensively discussed in the following references, which discussions are incorporated herein by reference:

a) WO 00/12508 (pages 14 to 30);

b) WO 2005/023814 (pages 3 to 10);

c) WO 2004/043963 (pages 28 to 29); and d) WO 2005/085251 (pages 30 to 39).

Synthesis Route

Compounds of the present invention of formula I:

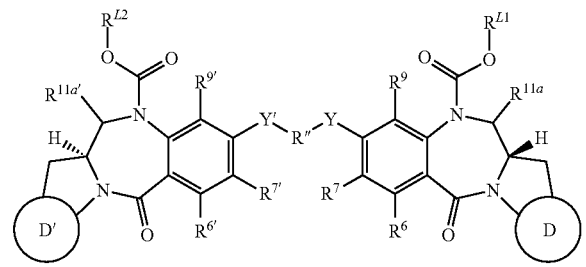

can be synthesised from a compound of Formula 2:

Formula 2

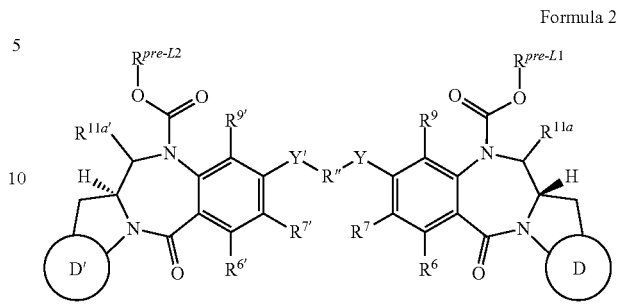

where $R^2$, $R^6$, $R^7$, $R^9$, $R^{11a}$, $R^{6'}$, $R^{7'}$, $R^{9'}$, $R^{11a'}$, Y, Y' and R" are as defined for compounds of formula I, $R^{pre-L1}$ is a precursor of $R^{L1}$ and $R^{pre-L2}$ is a precursor of $R^{L2}$—this method is particularly applicable to compounds of formula I where $R^{L1}$ and $R^{L2}$ are of formula IIIa. For these compounds, $R^{pre-L1}$ and $R^{pre-L2}$ will typically be portions of $R^{L1}$ and $R^{L2}$, such as a group of formula IIIa':

IIIa'

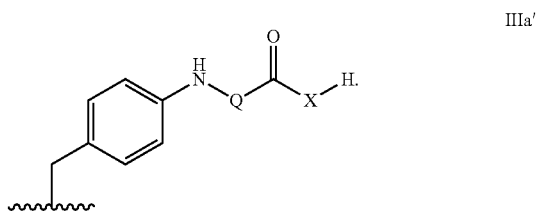

In such as case, the reaction involves adding the group $G^L$.

The compounds of Formula 2 may be made by deprotecting compounds of Formula 3:

Formula 3

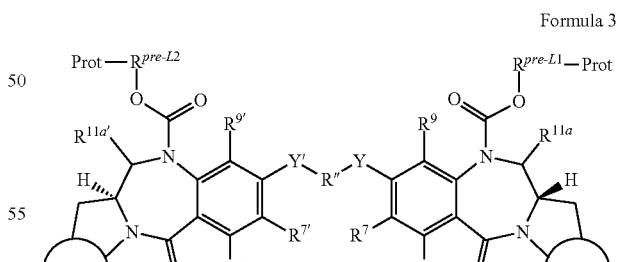

where $R^2$, $R^6$, $R^7$, $R^9$, $R^{11a}$, $R^{6'}$, $R^{7'}$, $R^{9'}$, $R^{11a'}$, Y, Y' and R" are as defined for compounds of formula I, $R^{pre-L1Prot}$ is a protected version of $R^{pre-L1}$, $R^{pre-L2Prot}$ is a protected version of $R^{pre-L2}$ and the Prot represents an appropriate carboxy/hydroxy protecting group.

Compounds of formula 3 may be made by ring-closure of compounds of Formula 4:

Formula 4

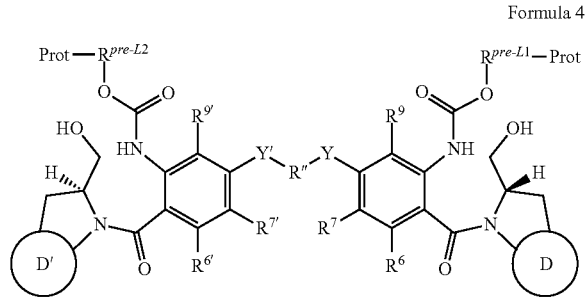

where the ring closure is carried out by oxidation, e.g. Swern.

Compounds of formula 4 can be synthesised from compounds of formula 5:

Formula 5

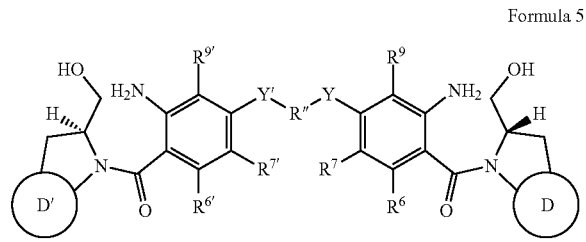

by addition of the two amino protecting groups. If the groups are different, step-wise addition can be achieved by simple protection of one amino group (e.g. by Fmoc), followed by installation of a desired protecting group at the other amino group. This can be followed by removal of the simple protecting group, and then installation of the other desired amino protecting group.

Compounds of formula I where $R^{L1}$ and $R^{L2}$ are of formula IIIb, may be synthesised in a similar manner, although the complete $R^{L1}$ and/or $R^{L2}$ group may be installed starting from a compound of Formula 5, rather than with the use of a protected precursor.

Compounds of Formula 5 can be synthesised by known methods, such as those disclosed in WO 2011/130598.

Synthesis of Drug Conjugates

Antibodies can be conjugated to the Drug Linker compound generally as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 3 equivalents of drug-linker per antibody. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Further Preferences

The following preferences may apply to all aspects of the invention as described above, or may relate to a single aspect. The preferences may be combined together in any combination.

$R^{6'}$, $R^{7}$, $R^{9'}$, $R^{11a'}$ and Y' are selected from the same groups as $R^6$, $R^7$, $R^9$, $R^{11a}$ and Y respectively. In some embodiments, $R^{6'}$, $R^{7'}$, $R^{9'}$, $R^{11a'}$ and Y' are the same as $R^6$, $R^7$, $R^9$, $R^{11a}$ and Y respectively.

In some embodiments, $R^{12}$ is the same as $R^2$.

Dimer Link

In some embodiments, Y and Y' are both O.

In some embodiments, R" is a $C_{3-7}$ alkylene group with no substituents. In some of these embodiments, R" is a $C_3$, $C_5$ or $C_7$ alkylene. In particular, R" may be a $C_3$ or $C_5$ alkylene.

In other embodiments, R" is a group of formula:

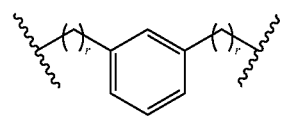

where r is 1 or 2.

$R^6$ to $R^9$

In some embodiments, $R^9$ is H.

In some embodiments, $R^6$ is selected from H, OH, OR, SH, $NH_2$, nitro and halo, and may be selected from H or halo. In some of these embodiments $R^6$ is H.

In some embodiments, $R^7$ is selected from H, OH, OR, SH, SR, $NH_2$, NHR, NRR', and halo. In some of these embodiments $R^7$ is selected from H, OH and OR, where R is selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. $-NMe_2$); $-(OC_2H_4)_q$OMe, where q is from 0 to 2; nitrogen-containing $C_6$ heterocyclyls, including morpholino, piperidinyl and N-methyl-piperazinyl.

These embodiments and preferences apply to $R^{9'}$, $R^{6'}$ and $R^{7'}$ respectively.

D and D'

In some embodiments, D and D' are D1 and D'1 respectively.

In some embodiments, D and D' are D2 and D'2 respectively.

$R^2$

When there is a double bond present between C2 and C3, $R^2$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;
(c) $C_{3-6}$ saturated cycloalkyl;
(d)

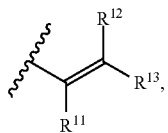

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;
(e)

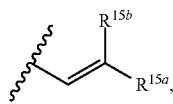

wherein one of $R^{15a}$ and $R^{15b}$ is H and the other is selected from: phenyl, which phenyl is optionally substituted by a group selected from halo methyl, methoxy; pyridyl; and thiophenyl; and
(f)

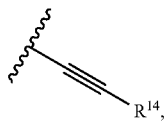

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^2$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^2$ is preferably phenyl. In other embodiments, $R^2$ is preferably thiophenyl, for example, thiophen-2-yl and thiophen-3-yl.

When $R^2$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^2$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^2$ is $C_{5-7}$ aryl group, a single substituent is preferably on a ring atom that is not adjacent the bond to the remainder of the compound, i.e. it is preferably p or y to the bond to the remainder of the compound. Therefore, where the $C_{5-7}$ aryl group is phenyl, the substituent is preferably in the meta- or para-positions, and more preferably is in the para-position.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^2$ Substituents, when $R^2$ is a $C_{5-10}$ Aryl Group

If a substituent on $R^2$ when $R^2$ is a $C_{5-10}$ aryl group is halo, it is preferably F or Cl, more preferably Cl.

If a substituent on $R^2$ when $R^2$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^2$ when $R^2$ is a $C_{5-10}$ aryl group is $C_{1-7}$ alkyl, it may preferably be a $C_{1-4}$ alkyl group (e.g. methyl, ethyl, propryl, butyl).

If a substituent on $R^2$ when $R^2$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^2$ when $R^2$ is a $C_{5-10}$ aryl group is bis-oxy-$C_{1-3}$ alkylene, this is preferably bis-oxy-methylene or bis-oxy-ethylene.

If a substituent on $R^2$ when $R^2$ is a $C_{5-10}$ aryl group is ester, this is preferably methyl ester or ethyl ester.

Particularly preferred substituents when $R^2$ is a $C_{5-10}$ aryl group include methoxy, ethoxy, fluoro, chloro, cyano, bis-oxy-methylene, methyl-piperazinyl, morpholino and methylthiophenyl. Other particularly preferred substituents for $R^2$ are dimethylaminopropyloxy and carboxy.

Particularly preferred substituted $R^2$ groups when $R^2$ is a $C_{5-10}$ aryl group include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^2$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

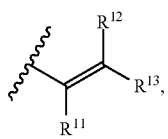

each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5. In some embodiments, the total number of carbon atoms in the $R^2$ group is no more than 4 or no more than 3.

In some embodiments, one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{11}$ is H.
In some embodiments, $R^{12}$ is H.
In some embodiments, $R^{13}$ is H.
In some embodiments, $R^{11}$ and $R^{12}$ are H.
In some embodiments, $R^{11}$ and $R^{13}$ are H.
In some embodiments, $R^{12}$ and $R^{13}$ are H.

An $R^2$ group of particular interest is:

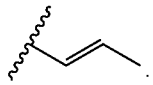

When $R^2$ is

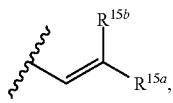

one of $R^{15a}$ and $R^{15b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^2$ is

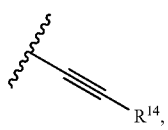

$R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{14}$ is selected from H, methyl, ethyl, ethenyl and ethynyl. In some of these embodiments, $R^{14}$ is selected from H and methyl.

When there is a single bond present between C2 and C3, $R^2$ is H or

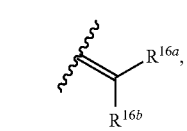

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester.

In some embodiments, $R^2$ is H.
In some embodiments, $R^2$ is

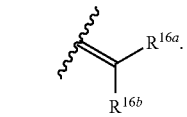

In some embodiments, it is preferred that $R^{16a}$ and $R^{16b}$ are both H.

In other embodiments, it is preferred that $R^{16a}$ and $R^{16b}$ are both methyl.

In further embodiments, it is preferred that one of $R^{16a}$ and $R^{16b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{22}$

When there is a double bond present between C2' and C3', $R^{22}$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

(d)

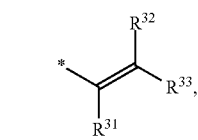

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{22}$ group is no more than 5;

(e)

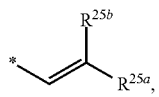

wherein one of $R^{25a}$ and $R^{25b}$ is H and the other is selected from: phenyl, which phenyl is optionally substituted by a group selected from halo methyl, methoxy; pyridyl; and thiophenyl; and (f)

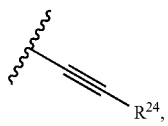

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{22}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{22}$ is preferably phenyl. In other embodiments, $R^{22}$ is preferably thiophenyl, for example, thiophen-2-yl and thiophen-3-yl.

When $R^{22}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^{22}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{22}$ is $C_{5-7}$ aryl group, a single substituent is preferably on a ring atom that is not adjacent the bond to the remainder of the compound, i.e. it is preferably p or y to the bond to the remainder of the compound. Therefore, where the $C_{5-7}$ aryl group is phenyl, the substituent is preferably in the meta- or para-positions, and more preferably is in the para-position.

Where $R^{22}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{22}$ Substituents, when $R^{22}$ is a $C_{5-10}$ Aryl Group

If a substituent on $R^{22}$ when $R^{22}$ is a $C_{5-10}$ aryl group is halo, it is preferably F or Cl, more preferably Cl.

If a substituent on $R^{22}$ when $R^{22}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g.

phenoxy, pyridyloxy, furanyloxy). The alkoxy group may itself be further substituted, for example by an amino group (e.g. dimethylamino).

If a substituent on $R^{22}$ when $R^{22}$ is a $C_{5-10}$ aryl group is $C_{1-7}$ alkyl, it may preferably be a $C_{1-4}$ alkyl group (e.g. methyl, ethyl, propryl, butyl).

If a substituent on $R^{22}$ when $R^{22}$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{22}$ when $R^{22}$ is a $C_{5-10}$ aryl group is bis-oxy-$C_{1-3}$ alkylene, this is preferably bis-oxy-methylene or bis-oxy-ethylene.

If a substituent on $R^{22}$ when $R^{22}$ is a $C_{5-10}$ aryl group is ester, this is preferably methyl ester or ethyl ester.

Particularly preferred substituents when $R^{22}$ is a $C_{5-10}$ aryl group include methoxy, ethoxy, fluoro, chloro, cyano, bis-oxy-methylene, methyl-piperazinyl, morpholino and methylthiophenyl. Other particularly preferred substituents for $R^{22}$ are dimethylaminopropyloxy and carboxy.

Particularly preferred substituted $R^{22}$ groups when $R^{22}$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{22}$ group is 4-nitrophenyl. $R^{22}$ groups of particular interest include 4-(4-methylpiperazin-1-yl)phenyl and 3,4-bisoxymethylene-phenyl.

When $R^{22}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{22}$ is $C_{3-6}$ saturated cycloalkyl, it may be cyclopropyl, cyclobutyl, cyclopentyl or cyclohexyl. In some embodiments, it may be cyclopropyl.

When $R^{22}$ is

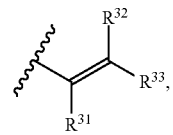

each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{22}$ group is no more than 5. In some embodiments, the total number of carbon atoms in the $R^{22}$ group is no more than 4 or no more than 3.

In some embodiments, one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{31}$ is H.
In some embodiments, $R^{32}$ is H.
In some embodiments, $R^{33}$ is H.
In some embodiments, $R^{31}$ and $R^{32}$ are H.
In some embodiments, $R^{31}$ and $R^{33}$ are H.
In some embodiments, $R^{32}$ and $R^{33}$ are H.

An $R^{22}$ group of particular interest is:

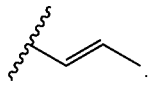 [SMILES: */C=C/C]

When $R^{22}$ is

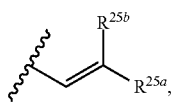

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{22}$ is

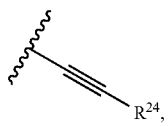

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2' and C3', $R^{22}$ is H or

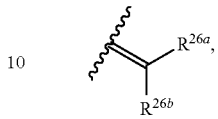

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, $R^{22}$ is H.
In some embodiments, $R^{22}$ is

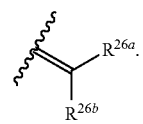

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{11}$
In some embodiments, $R^{11a}$ is OH.
In some embodiments, $R^{11a}$ is $OR^A$, where $R^A$ is $C_{1-4}$ alkyl. In some of these embodiments, $R^A$ is methyl.

In some embodiments of the first aspect of the present invention are of formula Ia-1, Ia-2 or Ia-3:

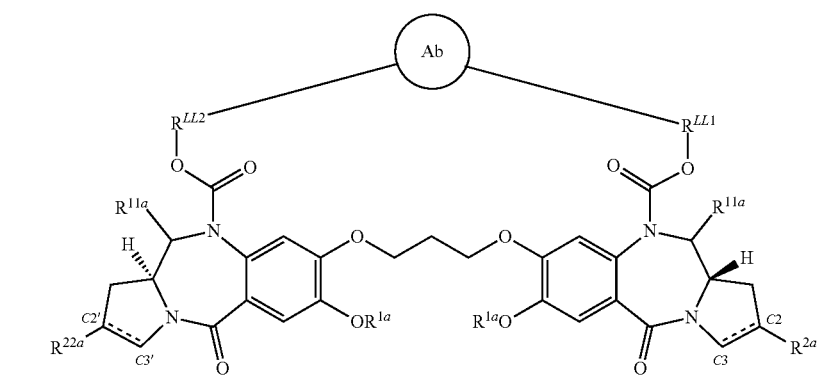

Ia

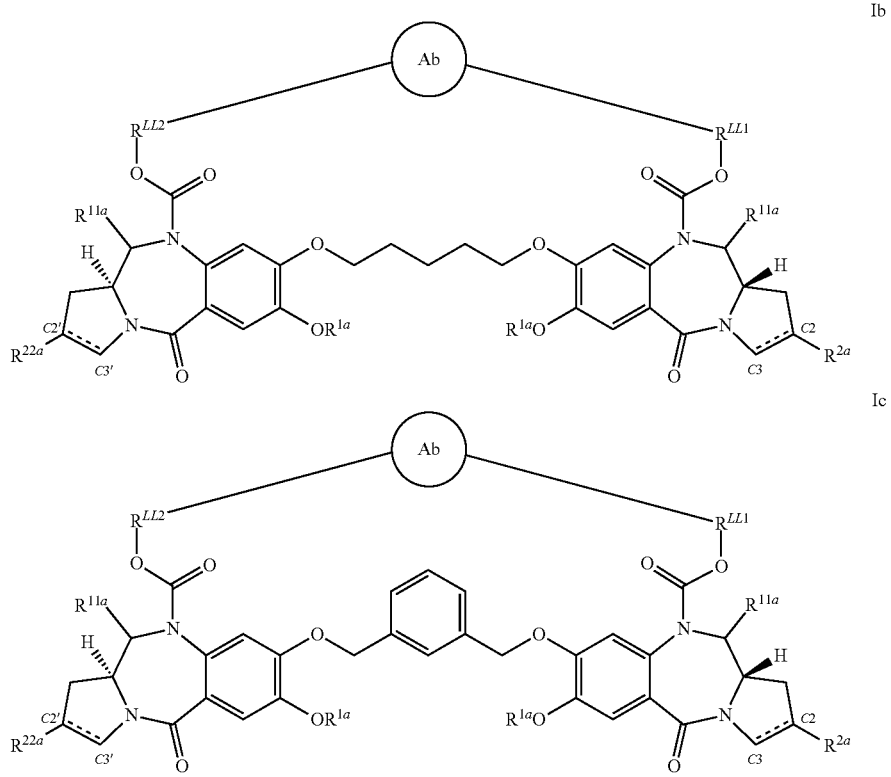

where $R^{2a}$ and $R^{22a}$ are the same and are selected from:

(a) 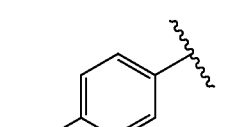;

(b) 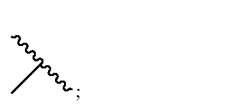;

(c) 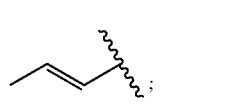;

(d) 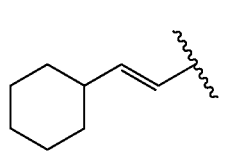;

(e) ;

(f) 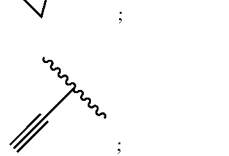;

(g) 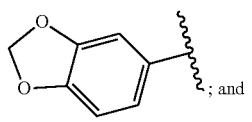; and (h) 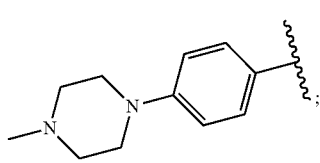;

$R^{1a}$ is selected from methyl and benzyl;

$R^{LL1}$, $R^{LL2}$ and $R^{11a}$ are as defined above.

In some embodiments of the present invention both $R^2$ and $R^{22}$ comprise no more than 3 carbon atoms.

Thus in these embodiments where there is a double bond present between C2 and C3, $R^2$ may be selected from:

(i) Methyl;

(ii) Ethyl;

(iii) Propyl;

(iv) Cyclopropyl;

-continued (v)
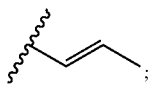;

(vi)
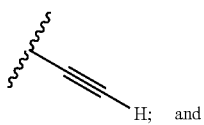 H; and (vi)
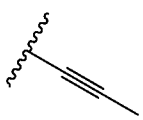

Thus in these embodiments where there is no double bond present between C2 and C3, R² may be selected from:

(i)
H;

(ii)
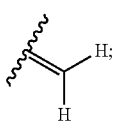 H;

(iii)
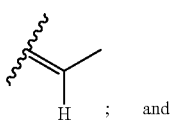 ; and (iv)
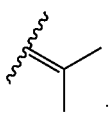.

Thus in these embodiments where there is a double bond present between C2' and C3', R²² may be selected from:

(i) Methyl;

(ii) Ethyl;

(iii) Propyl;

(iv) Cyclopropyl;

(v)
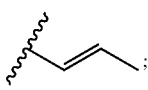;

(vi)
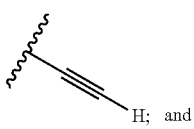 H; and (vi)
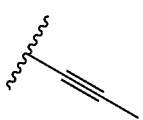

Thus in these embodiments where there is no double bond present between C2' and C3', R²² may be selected from:

(i)
H;

(ii)
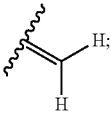 H;

(iii)
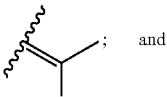 ; and (iv)
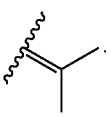.

In some of these embodiments both R² and R²² comprise no more than 2 carbon atoms.

Thus in these embodiments where there is a double bond present between C2 and C3, R² may be selected from:

(i) Methyl;

(ii) Ethyl; and (iv)
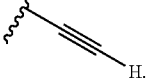 H.

Thus in these embodiments where there is no double bond present between C2 and C3, R² may be selected from:

(i)
H;

(ii)
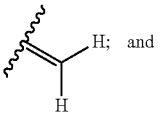 H; and (iii)
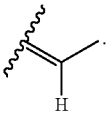.

Thus in these embodiments where there is a double bond present between C2' and C3', R²² may be selected from:

(i) Methyl;

(ii) Ethyl; and (iv)

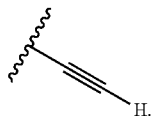

Thus in these embodiments where there is no double bond present between C2' and C3', $R^{22}$ may be selected from:

(i)

H;

(ii)

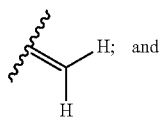

and (iii)

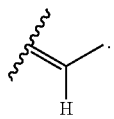

In further of these embodiments both $R^2$ and $R^{22}$ comprise no more than 1 carbon atom.

Thus in these embodiments where there is a double bond present between C2 and C3, $R^2$ may be methyl. Thus in these embodiments where there is no double bond present between C2 and C3, $R^2$ may be selected from:

(i)

H; and (ii)

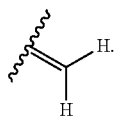

Thus in these embodiments where there is a double bond present between C2' and C3', $R^{22}$ may be methyl. Thus in these embodiments where there is no double bond present between C2' and C3', $R^{22}$ may be selected from:

(i)

H; and (ii)

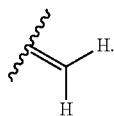

Without wishing to be bound by theory, where the substituent at the C2 position of the PBD dimers are small, the use of the glucuronide capping unit in these drug linkers is believed to be particularly advantageous, as it significantly increases the hydrophilicity of the drug linker, making the drug linkers easier to conjugate to a ligand unit.

These embodiments and preferences also apply to the second aspect of the invention.

Linker ($R^L/R^{LL}$)

In some embodiments, $R^{LL1}$ and $R^{LL2}$ are of formula IIIa'.

In some embodiments, $R^{L1}$ and $R^{L2}$ are of formula IIIa.

$G^L$ $G^L$ may be selected from ($G^{L1-1}$)

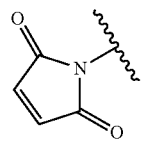

($G^{L1-2}$)

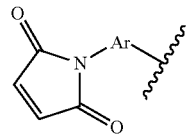

($G^{L2}$)

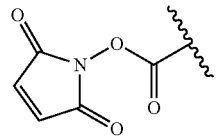

($G^{L3-1}$)

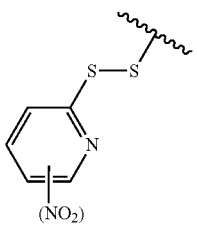

where the $NO_2$ group is optional ($G^{L3-2}$)

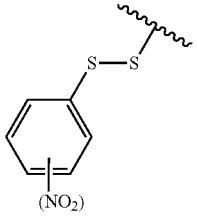

where the $NO_2$ group is optional ($G^{L3-3}$)

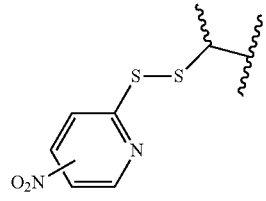

where the $NO_2$ group is optional

-continued (G^{L3-4})

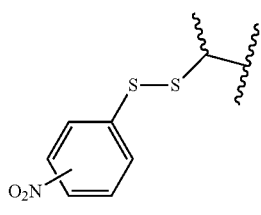

where the NO$_2$ group is optional (G^{L4})

(G^{L5})

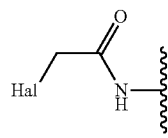

Where Hal = I, Br, Cl (G^{L6})

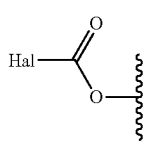

(G^{L7})

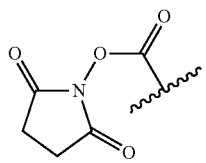

(G^{L8})

(G^{L9})

(G^{L10})

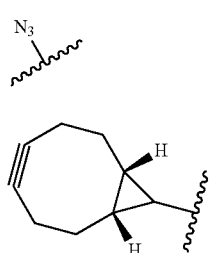

(G^{L11})

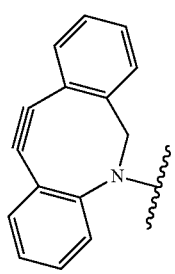

-continued (G^{L12})

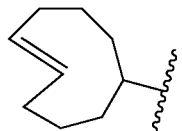

(G^{L13})

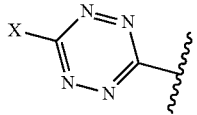

where Ar represents a $C_{5-6}$ arylene group, e.g. phenylene, and X represents $C_{1-4}$ alkyl In some embodiments, $G^L$ is selected from $G^{L1-1}$ and $G^{L1-2}$. In some of these embodiments, $G^L$ is $G^{L1-1}$.

$G^{LL}$ $G^{LL}$ may be selected from:

(G^{LL1-1})

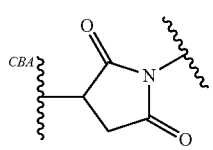

(G^{LL1-2})

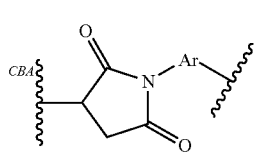

(G^{LL2})

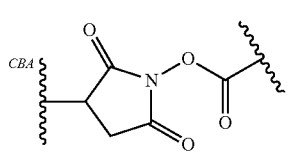

(G^{LL3-1})

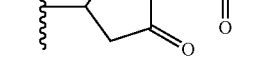

(G^{LL3-2})

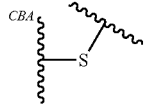

(G^{LL4})

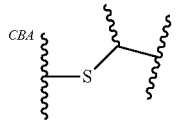

(G^{LL5})

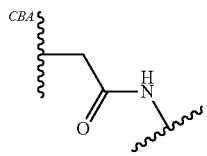

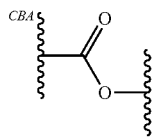

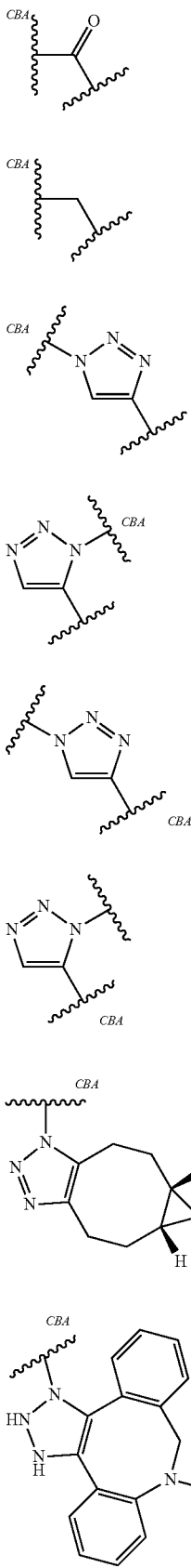

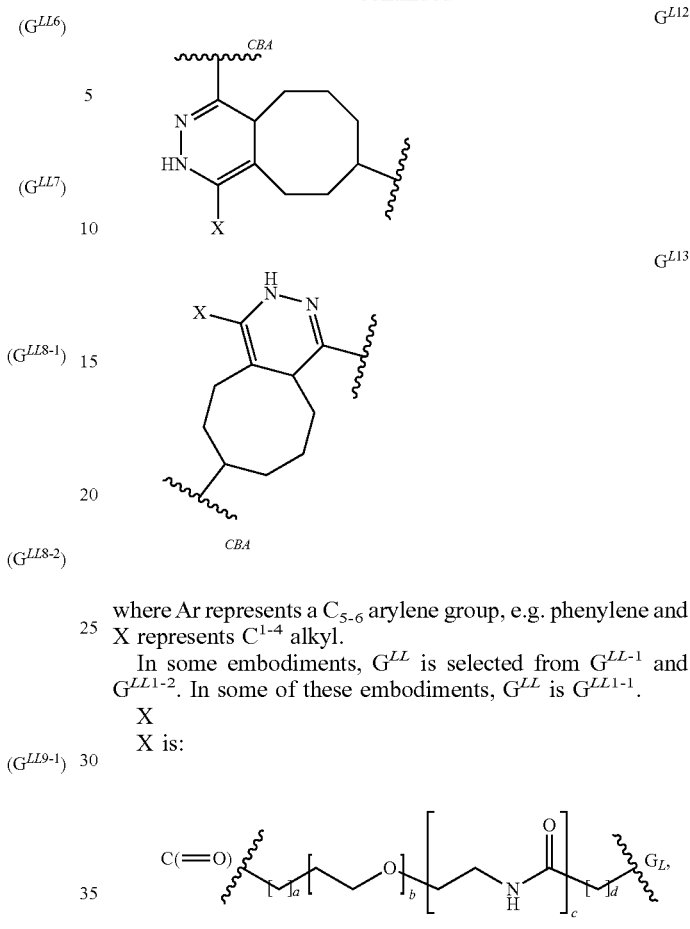

where Ar represents a $C_{5-6}$ arylene group, e.g. phenylene and X represents $C^{1-4}$ alkyl.

In some embodiments, $G^{LL}$ is selected from $G^{LL-1}$ and $G^{LL1-2}$. In some of these embodiments, $G^{LL}$ is $G^{LL1-1}$.

X

X is:

where a=0 to 5, b=0 to 16, c=0 or 1, d=0 to 5.

a may be 0, 1, 2, 3, 4 or 5. In some embodiments, a is 0 to 3. In some of these embodiments, a is 0 or 1. In further embodiments, a is 0.

b may be 0, 1, 2, 3, 4, 5, 6, 7, 8, 9, 10, 11, 12, 13, 14, 15 or 16. In some embodiments, b is 0 to 12. In some of these embodiments, b is 0 to 8, and may be 0, 2, 4 or 8.

c may be 0 or 1.

d may be 0, 1, 2, 3, 4 or 5. In some embodiments, d is 0 to 3. In some of these embodiments, d is 1 or 2. In further embodiments, d is 2.

In some embodiments of X, a is 0, c is 1 and d is 2, and b may be from 0 to 8. In some of these embodiments, b is 0, 4 or 8.

$Q^X$

In one embodiment, $Q^X$ is an amino acid residue. The amino acid may a natural amino acids or a non-natural amino acid.

In one embodiment, $Q^X$ is selected from: Phe, Lys, Val, Ala, Cit, Leu, Ile, Arg, and Trp, where Cit is citrulline.

In one embodiment, $Q^X$ comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, $Q^X$ is selected from:
$^{CO}$-Phe-Lys-$^{NH}$,
$^{CO}$-Val-Ala-$^{NH}$, $^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$;
where Cit is citrulline.

Preferably, $Q^X$ is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$.

Most preferably, $Q^X$ is selected from $^{CO}$-Phe-Lys-$^{NH}$, $^{CO}$-Val-Cit-$^{NH}$ and $^{CO}$-Val-Ala-$^{NH}$.

Other dipeptide combinations of interest include:
$^{CO}$-Gly-Gly-$^{NH}$,
$^{CO}$-Pro-Pro-$^{NH}$, and
$^{CO}$-Val-Glu-$^{NH}$.

Other dipeptide combinations may be used, including those described by Dubowchik et al., *Bioconjugate Chemistry*, 2002, 13,855-869, which is incorporated herein by reference.

In some embodiments, $Q^X$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, $R^{LL1}$ and $R^{LL2}$ are of formula IIIb'.
In some embodiments, $R^{L1}$ and $R^{L2}$ are of formula IIIb.
$R^{SL1}$ and $R^{SL2}$ are independently selected from H and methyl, or together with the carbon atom to which they are bound form a cyclopropylene or cyclobutylene group.
In some embodiments, both $R^{SL1}$ and $R^{SL2}$ are H.
In some embodiments, $R^{SL1}$ is H and $R^{SL2}$ is methyl.
In some embodiments, both $R^{SL1}$ and $R^{SL2}$ are methyl.
In some embodiments, $R^{SL1}$ and $R^{L2}$ together with the carbon atom to which they are bound form a cyclopropylene group.
In some embodiments, $R^{SL1}$ and $R^{SL2}$ together with the carbon atom to which they are bound form a cyclobutylene group.
In the group IIIb, in some embodiments, e is 0. In other embodiments, e is 1 and the nitro group may be in any available position of the ring. In some of these embodiments, it is in the ortho position. In others of these embodiments, it is in the para position.
In some embodiments, $R^{L1}$ and $R^{L2}$ are the same.
In some embodiments, $R^{LL1}$ and $R^{LL2}$ are the same.
In one particular embodiment, the first aspect of the invention comprises a conjugate of formula Id:

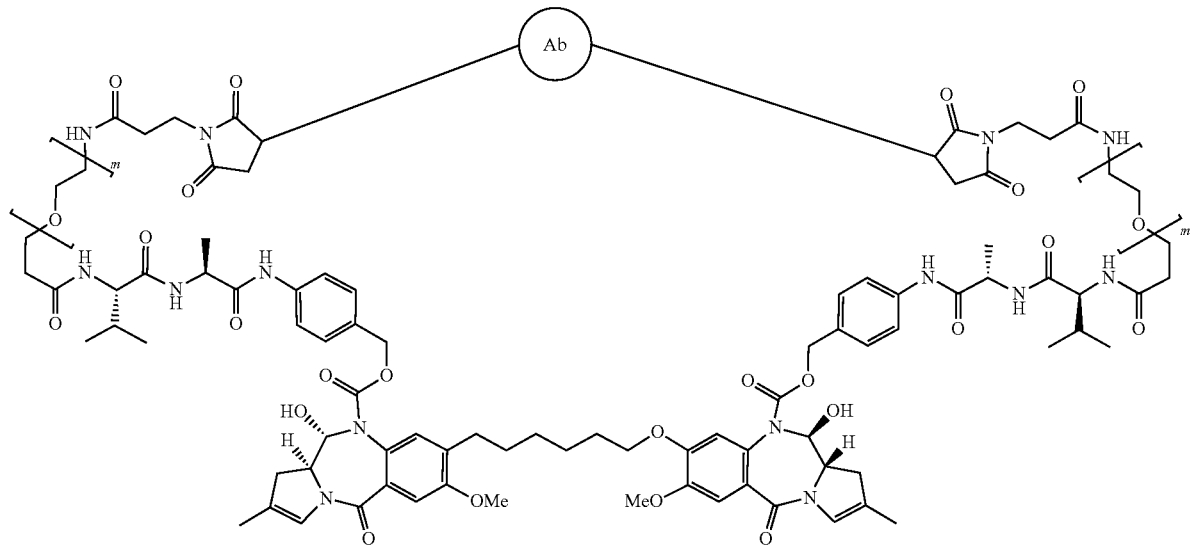

where m is an integer from 2 to 8.

In one particular embodiment, the second aspect of the invention, the Drug linker ($D^L$) is of formula (Id'):

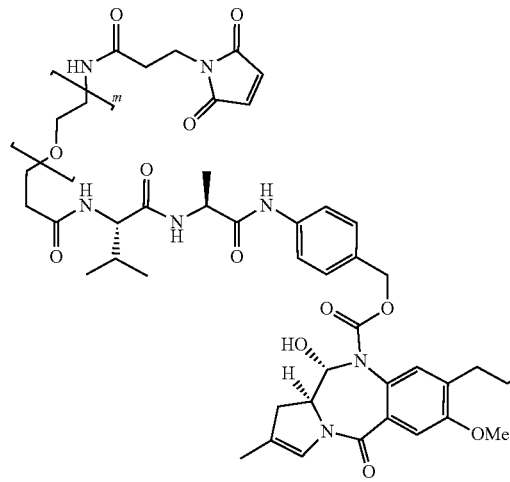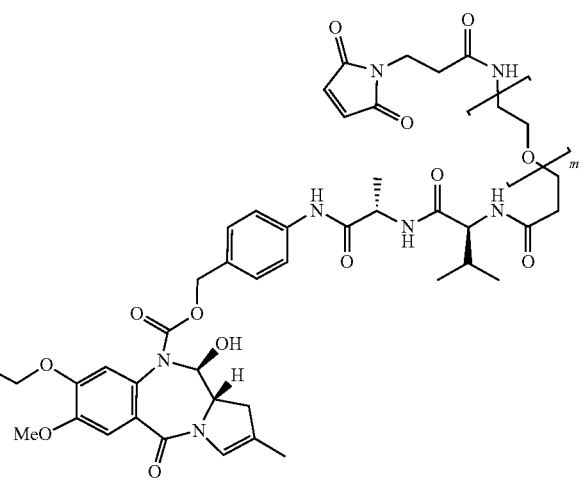

where m is an integer from 2 to 8.

In some embodiments, $R^{L1}$ and $R^{L2}$ are different.

In some embodiments, $R^{LL1}$ and $R^{LL2}$ are different.

In particular, in embodiments where the linking groups are different, differences may only be in the G groups, such that the remainder of the linking groups are the same (so that the cleavage triggers are the same).

In some embodiments of the present invention, the C11 substituent may be in the following stereochemical arrangement relative to neighbouring groups:

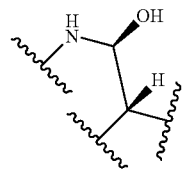

In other embodiments, the C11 substituent may be in the following stereochemical arrangement relative to neighbouring groups:

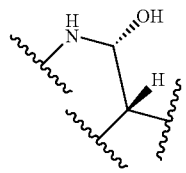

Compounds of particular interest include those of the examples.

EXAMPLES

Flash chromatography was performed using silica gel under pressure. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich unless otherwise stated. Pegylated reagents were obtained from Quanta biodesign US via Stratech UK or from Pierce Scientific via Thermo Fisher $^1$H and $^{13}$C NMR spectra were obtained on a Bruker Avance® 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), and m (multiplet).

The analytical LC/MS conditions (for reaction monitoring and purity determination) were as follows: Positive mode electrospray mass spectrometry was performed using a Shimadzu Nexera®/Prominence® LCMS-2020. Mobile phases used were solvent A ($H_2O$ with 0.1% formic acid) and solvent B ($CH_3CN$ with 0.1% formic acid). Gradient for routine 3-minute run: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Gradient for 15-minute run: Initial composition 5% B held over 1.25 minutes, then increased from 5% B to 100% B over an 8.75 minute period. The composition was held for 2.5 minutes at 100% B, then returned to 5% B in 30 seconds and held there for 2 minutes. The total duration of the gradient run was 15.0 minutes. Flow rate was 0.8 mL/minute (for 3-minute run) and 0.5 mL/minute (for 15-minute run). Detection was at 254 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm (routine 3-minute run); and Waters Acquity UPLC CSH C18, 1.7p, 2.1×100 mm fitted with Waters Acquity UPLC® BEH Shield RP18 VanGuard Pre-column, 130A, 1.7 μm, 2.1 mm×5 mm (15 minute run).

The preparative HPLC conditions were as follows: Reverse-phase ultra-fast high-performance liquid chromatography (UFLC) was carried out on a Shimazdzu Prominence® machine using a Phenomenex® Gemini NX 5μ C18 column (at 50° C.) 150×21.2 mm. Eluents used were solvent A (H₂O with 0.05% formic acid) and solvent B (CH₃CN with 0.05% formic acid). All UFLC experiments were performed with gradient conditions: Initial composition 13% B, the composition was then increased to 100% B over a total of 17 minutes at a gradient suitable to effect the desired separation, then held for 1 minute at 100% B, then returned to 13% B in 0.1 minute and held there for 1.9 minutes. The total duration of the gradient run was 20.0 minutes. Flow rate was 20.0 mL/minute and detection was at 254 and 280 nm.

Example 1

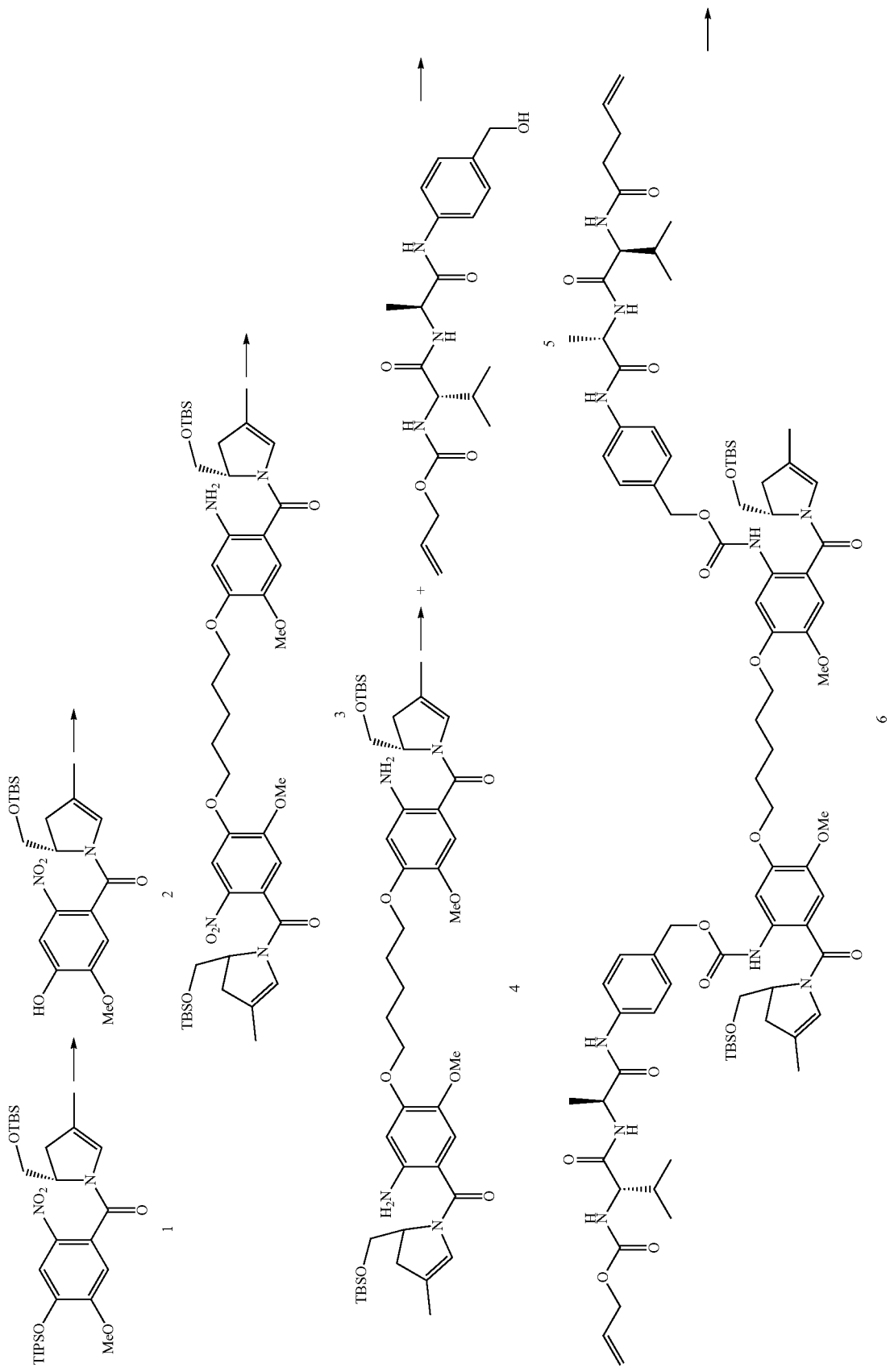

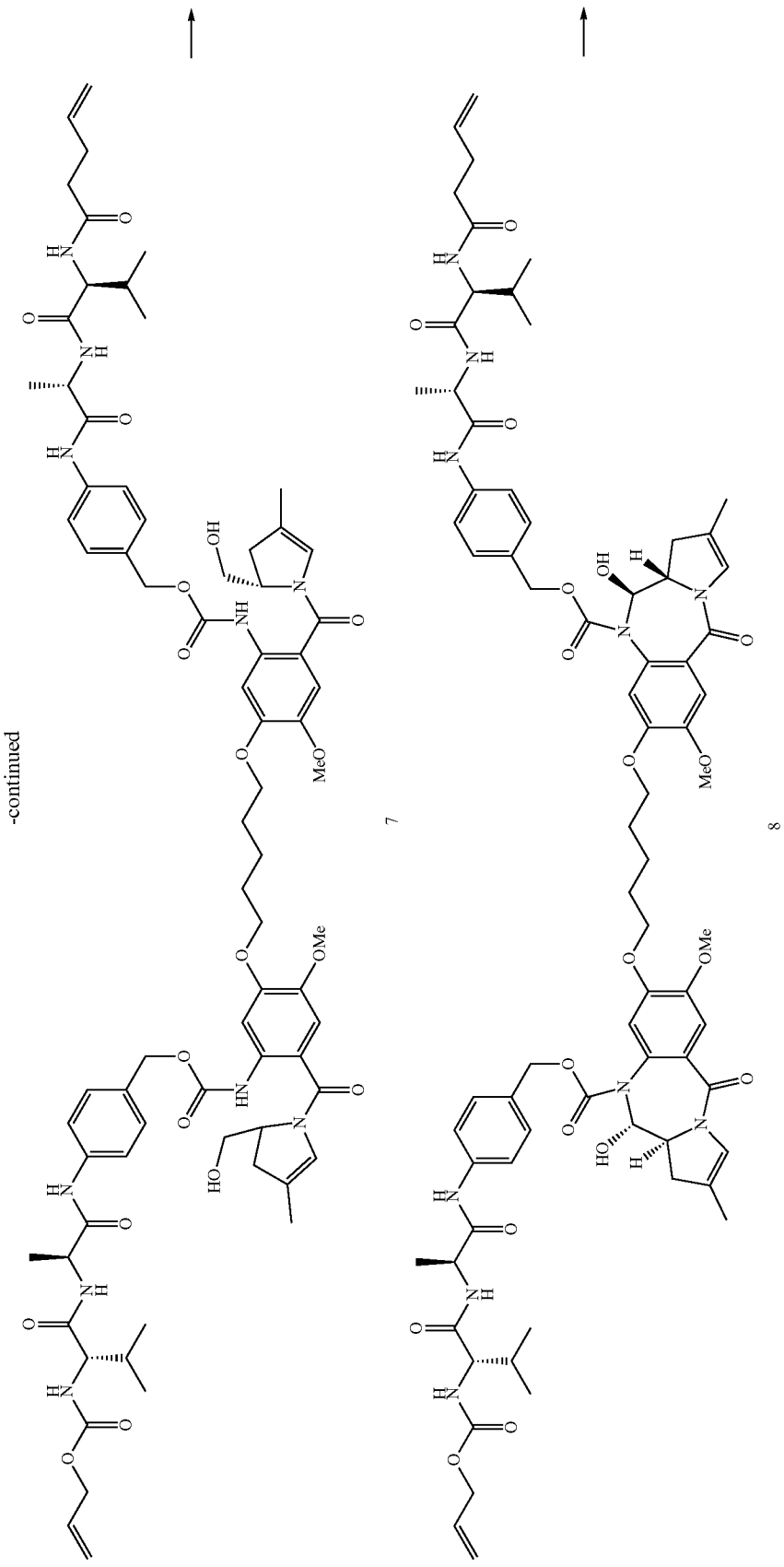

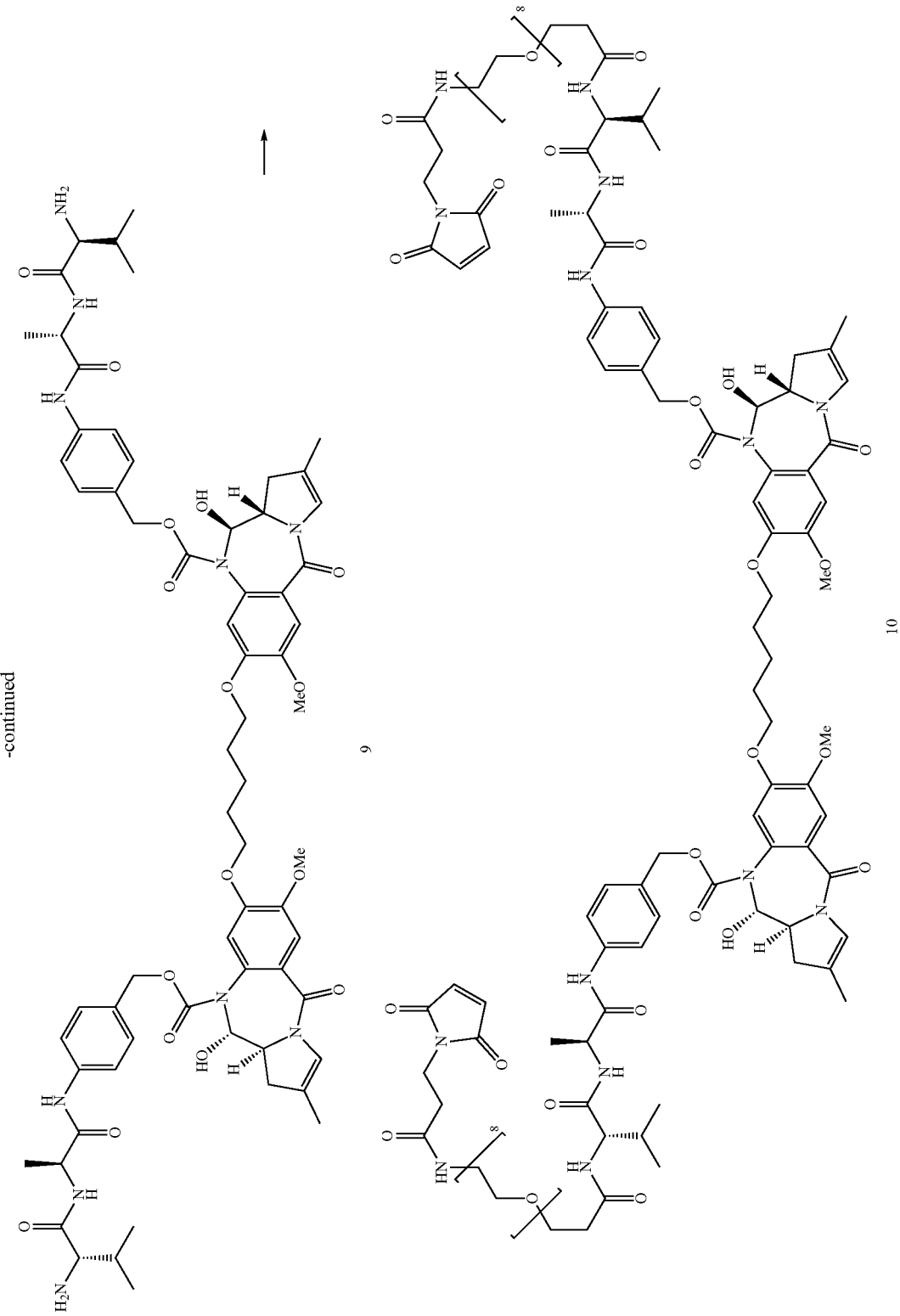

(a) (S)-(2-(((tert-butyldimethylsilyl)oxy)methyl)-4-methyl-2,3-dihydro-1H-pyrrol-1-yL)(4-hydroxy-5-methoxy-2-nitrophenyl)methanone (2)

Lithium acetate dihydrate (3.52 g, 34.5 mmol, 1.0 eq.) was added to a stirred solution of TIPS ether (1) (19.96 g, 34.5 mmol, 1.0 eq.) in DMF/H$_2$O (300 mL/4 mL). The resultant red solution was stirred at room temperature for 3.5 h. The reaction mixture was diluted with EtOAc (600 mL) and washed with 1M citric acid solution (2×250 mL), H$_2$O (2×250 mL), saturated brine (300 mL) and dried (MgSO$_4$). The solvent was evaporated under reduced pressure to afford the product as a yellow solid (14.57 g, 100%). The product was used without further purification. Analytical Data: LC/MS, RT 1.74 min; MS (ES$^+$) m/z (relative intensity) 423 ([M+H]$^+$, 100); 445 ([M+Na]$^{+•}$, 75).

(b) ((Pentane-1,5-diylbis(oxy))bis(5-methoxy-2-nitro-4,1-phenylene))bis(((S)-2-(((tert-butyldimethylsilyl)oxy)methyl)-4-methyl-2,3-dihydro-1H-pyrrol-1l-yl)methanone) (3)

Potassium carbonate (5.03 g, 36.44 mmol, 1.1 eq.) was added to a stirred solution of phenol (2) (14 g, 33.13 mmol, 1.0 eq.) and 1,5 diiodopentane (21.46 g, 9.86 mL, 66.26 mmol, 2.0 eq.) in DMF (250 mL). The solution was heated at 7000 for 3.5 h. The solution was poured into a mixture of ice/water (800 mL) and extracted with EtOAc (4×500 mL). The combined extracts were washed with H$_2$O (2×250 mL), saturated brine (400 mL), dried (MgSO$_4$) and evaporated under reduced pressure to give a brown oil. Purification by flash column chromatography [n-heptane/EtOAc 40% to 80% in 10% increments] gave the product as a yellow foam (12.7 g, 85%). Analytical Data: LC/MS, RT 2.16 min; MS (ES$^+$) m/z (relative intensity) 913 ([M+H]$^{+•}$, 100); 935 ([M+Na]$^{+•}$, 100).

(c) ((Pentane-1,5-diylbis(oxy))bis(2-amino-5-methoxy-4,1-phenylene))bis(((S)-2-(((tert-butyldimethylsilyl)oxy)methyl)-4-methyl-2,3-dihydro-1H-pyrrol-1-yl)methanone) (4)

Zinc dust (19.9 g, 304 mmol, 40 eq.) was treated with 1M HCl (100 mL) and stirred for 10 minutes at room temperature. The mixture was then sonicated for 10 minutes and the activated Zinc collected by vacuum filtration then washed with 1M HCl (50 mL), H$_2$O (to pH 6 to 7), MeOH and dried in vacuo on the filter pad. The activated zinc was added to a vigorously stirred solution of the bis nitro compound (3) (6.94 g, 7.6 mmol, 1.0 eq.) in EtOH/H$_2$O/EtOAc (60 mL/4 mL/60 mL) at room temperature. The reaction mixture was treated drop-wise with a solution of 5% v/v HCO$_2$H in MeOH (76 mL). A colour change from green to metallic grey and an exotherm to 42° C. were observed. Once the exotherm had subsided to 30° C. LC/MS indicated that the reaction was not complete. A further portion of 5% v/v HCO$_2$H in MeOH (20 mL) was added and a further exotherm was observed (34° C.) The reaction mixture was allowed to cool to room temperature at which point analysis by LC/MS revealed complete conversion to desired product. The mixture was filtered through Celite® and the pad washed with EtOAc. The filtrate was washed with saturated aqueous NaHCO$_3$ (2×300 mL), water (300 mL), saturated brine (300 mL), dried (MgSO$_4$), filtered and evaporated in vacuo to provide the bis-aniline as a yellow foam (6.22 g, 96%). The product was used without further purification.

Analytical Data: LC/MS, RT 2.12 min; MS (ES$^+$) m/z (relative intensity) 853 ([M+H]$^{+•}$, 15).

(d) Bis(4-((S)-2-((S)-2-(((allyloxy)carbonyl)amino)-3-methylbutanamido)propanamido)benzyl) ((pentane-1,5-diylbis(oxy))bis(6-((S)-2-(((tert-butyldimethylsilyl)oxy)methyl)-4-methyl-2,3-dihydro-1H-pyrrole-1-carbonyl)-4-methoxy-3,1-phenylene)) dicarbamate (6)

Triethylamine (0.171 g, 235 μL, 1.69 mmol, 4.4 eq.) was added via syringe to a stirred solution of bis aniline (4) (0.33 g, 0.38 mmol, 1.0 eq.) and triphosgene (0.082 g, 0.28 mmol, 0.72 eq.) in dry THE under an argon atmosphere. The resultant suspension was heated to 40° C. and after 5 min sampled in MeOH for LC/MS as the bis methyl carbamate (MS (ES$^+$) m/z (relative intensity) 969 ([M+H]$^{+•}$, 80); 992 ([M+Na])$^{+•}$, 100). Dibutyltin dilaurate (0.024 g, 23 μL, 38 μmol, 0.1 eq.) then solid linker (5) (0.319 g, 0.85 mmol, 2.2 eq.) and trimethylamine (0.085 g, 118 μL, 0.85 mmol, 2.2 eq.) were added and the mixture heated at 40° C. with stirring under an argon atmosphere for 5 h. The reaction mixture was allowed to cool, filtered and the THF evaporated under reduced pressure. The residue was purified by flash column chromatography [CHCl$_3$/MeOH 0%, 1%, 1.5%, 2%, gradient elution] to give the product as a yellow foam (0.42 g, 66%). Analytical Data: LC/MS, RT 2.16 min; MS (ES$^+$) m/z (relative intensity) 1660 ([M+H]$^{+•}$, 60); 1682 ([M+Na])$^{+•}$, 65).

(e) Bis(4-((S)-2-((S)-2-(((allyloxy)carbonyl)amino)-3-methylbutanamido)propanamido)benzyl) ((pentane-1,5-diylbis(oxy))bis(6-((S)-2-(hydroxymethyl)-4-methyl-2,3-dihydro-1H-pyrrole-1-carbonyl)-4-methoxy-3,1-phenylene))dicarbamate (7)

p-Toluenesulfonic acid (0.296 g, 1.7 mmol, 2.2 eq.) was added to a stirred solution of bis-tert-butyldimethylsilyl ether (6) (1.26 g, 0.76 mmol, 1.0 eq.) in 10% v/v H$_2$O in THF. The solution was stirred at room temperature for 18 h. The reaction mixture was diluted with EtOAc (100 mL) and washed with saturated NaHCO$_3$ solution (2×100 mL), H$_2$O (100 mL), saturated brine (100 mL), dried (MgSO$_4$) and evaporated under reduced pressure. The residue was purified by flash column chromatography [CHCl$_3$/MeOH 0% to 5% in 1% increments] to give the product as a white foam (0.896 g, 92%). Analytical Data: LC/MS, RT 1.61 min; MS (ES$^+$) m/z (relative intensity) 1432 ([M+H]$^{+•}$, 5); 1454 ([M+Na])$^{+•}$, 5).

(f) Bis(4-((S)-2-((S)-2-(((allyloxy)carbonyl)amino)-3-methylbutanamido)propanamido)benzyl) 8,8'-(pentane-1,5-diylbis(oxy))(11S,11aS,11'S,11a'S)-bis (11-hydroxy-7-methoxy-2-methyl-5-oxo-11,11a-dihydro-1H-pyrrolo[2,1-c][1,4]benzodiazepine-10 (5H)-carboxylate) (8)

Dess-Martin periodinane (0.24 g, 0.57 mmol, 2.0 eq.) was added to a stirred solution of bis-alcohol (7) in dry DCM (20 mL). The resultant white suspension was stirred at room temperature for 24 h. The reaction mixture was diluted with DCM (100 mL) and extracted with saturated NaHCO$_3$ solution (2×100 mL), water (100 mL), saturated brine (100 mL), dried (MgSO$_4$) and evaporated under reduced pressure. Purification by flash column chromatography [CHCl$_3$/MeOH 0% to 3% in 0.5% increments] gave the product as a white foam (0.28 g, 69%). Analytical Data: LC/MS, RT 1.58 min; MS (ES⁺) m/z (relative intensity) 1428 ([M+H]⁺˙, 20); 1450 ([M+Na])⁺˙, 30).

(g) Bis(4-((S)-2-((S)-2-amino-3-methylbutanamido) propanamido)benzyl) 8,8'-(pentane-1,5-diylbis(oxy)) (11S,11aS,11'S,11a'S)-bis(11-hydroxy-7-methoxy-2-methyl-5-oxo-11,11a-dihydro-1H-pyrrolo[2,1-c][1,4] benzodiazepine-10(5H)-carboxylate) (9)

Pd(PPh₃)₄ (8 mg, 7 μmol, 0.04 eq.) was added to a stirred solution of bis-alloc derivative (8) (0.25 g, 0.176 mmol 1.0 eq.) and pyrrolidine (31 mg, 36 μL 0.44 mmol, 2.5 eq.) in dry DCM (10 mL). The solution was stirred at room temperature for 2 h. The reaction mixture was partitioned between saturated NH₄Cl solution (50 mL) and DCM (50 mL). The DCM was separated and washed with saturated brine (100 mL), dried (MgSO₄) and evaporated under reduced pressure. The solid residue was triturated/sonicated with Et₂O (3×15 mL) and dried under vacuum to give the product as a white solid (0.207 g, 93%). The product was used without further purification. Analytical Data: LC/MS, RT 1.06 min; MS (ES⁺) m/z (relative intensity) 630 ([M+2H]⁺˙, 100).

(h) Bis(4-((2S,5S)-37-(2,5-dioxo-2,5-dihydro-1H-pyrrol-1-yl)-5-isopropyl-2-methyl-4,7,35-trioxo-10, 13,16,19,22,25,28,31-octaoxa-3,6,34-triazaheptatriacontanamido)benzyl) 8,8'-(pentane-1,5-diylbis(oxy)) (11S,11aS,11'S, 11a'S)-bis(11-hydroxy-7-methoxy-2-methyl-5-oxo-11,11a-dihydro-1H-pyrrolo[2,1-c][1, 4]benzodiazepine-10(5H)-carboxylate) (10)

EDCI.HCl (56 mg, 0.29 mmol, 3 eq.) was added to a stirred solution of bis-amine (9) (0.123 g, 98 μmol, 1.0 eq.) and MaldPEG®OH (0.128 g, 0.22 mmol, 2.2 eq.) in CHCl₃ (15 mL). The reaction mixture was stirred at room temperature for 30 min then diluted with CHCl₃ (50 mL) washed with H₂O (100 mL), saturated brine (100 mL), dried (MgSO₄) and evaporated under reduced pressure. Purification by preparative HPLC followed by lyophilisation gave the product as a white foam (0.047 g, 20%). Analytical Data: LC/MS, RT 6.61 min; MS (ES⁺) m/z (relative intensity) 1205 ([M+2H]⁺˙, 55).

Example 2

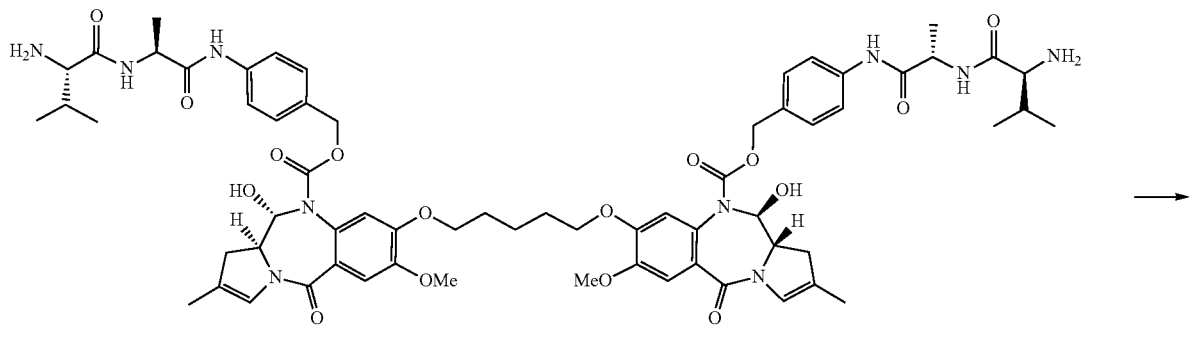

9

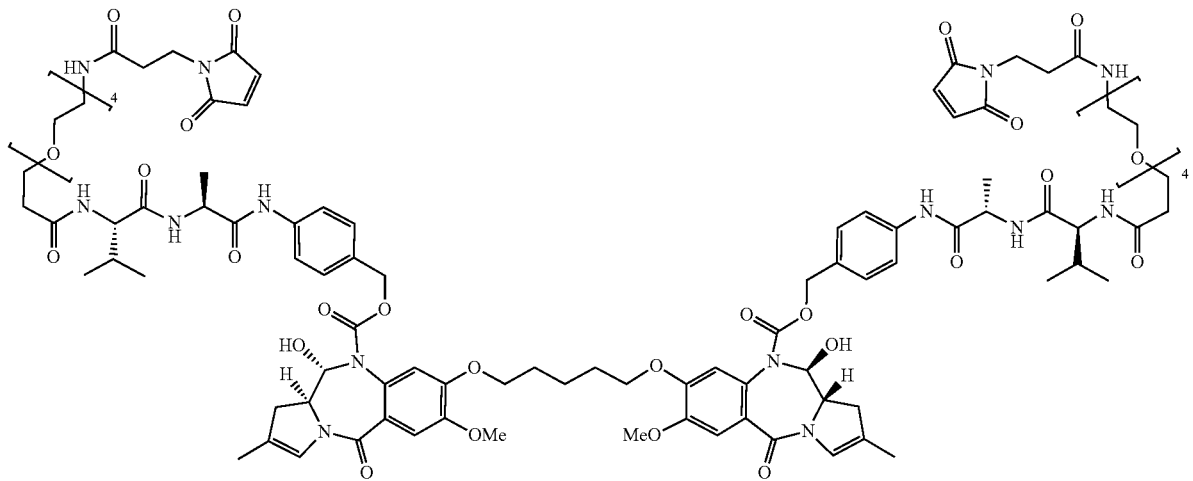

11

Bis(4-((2S,5S)-25-(2,5-dioxo-2,5-dihydro-1H-pyrrol-1-yl)-5-isopropyl-2-methyl-4,7,23-trioxo-10,13,16,19-tetraoxa-3,6,22-triazapentacosanamido)benzyl) 8,8'-(pentane-1,5-diylbis(oxy))(11S,11aS,11'S,11a'S)-bis(11-hydroxy-7-methoxy-2-methyl-5-oxo-11,11a-dihydro-1H-pyrrolo[2,1-c][1,4]benzodiazepine-10(5H)-carboxylate) (11)

DIPEA (30 mg, 42 μL, 0.23 mmol, 3 eq.) was added to a stirred solution of bis-amine (9) (98 mg, 78 μmol, 1.0 eq.) and MalPEG₄OSu (88 mg, 0.17 mmol, 2.2 eq.) in CHCl₃ (10 mL). The reaction mixture was stirred at room temperature for 72 h then diluted with CHCl₃ (50 mL) washed with H₂O (100 mL), saturated brine (100 mL), dried (MgSO₄) and evaporated under reduced pressure. Purification by preparative HPLC followed by lyophilisation gave the product as a white foam (0.043 g, 25%). Analytical Data: LC/MS, RT 6.11 min; MS (ES$^+$) m/z (relative intensity) 1028 ([M+2H]$^+$·, 80).

Example 3

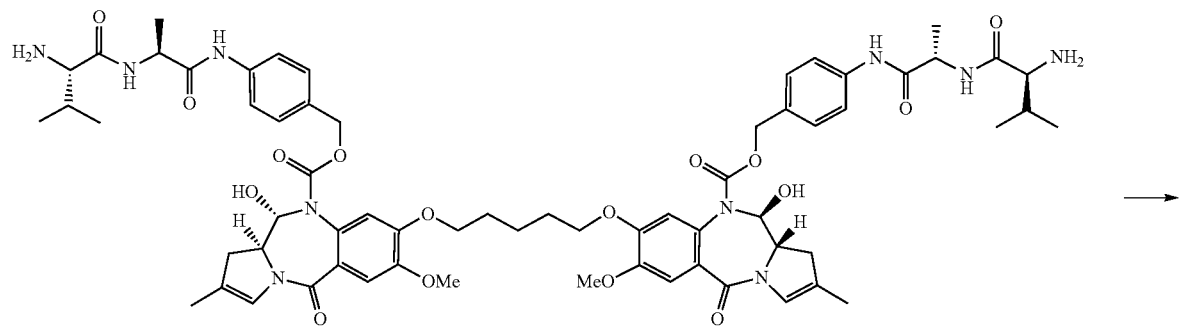

9

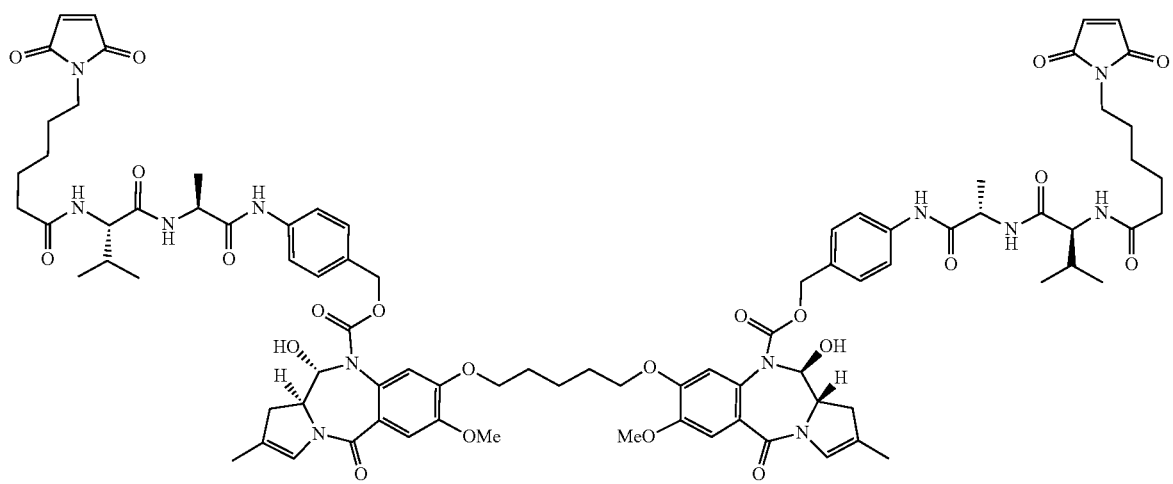

12 bis(4-((S)-2-((S)-2-(6-(2,5-dioxo-2,5-dihydro-1H-pyrrol-1-yl)hexanamido)-3-methylbutanamido)propanamido)benzyl) 8,8'-(pentane-1,5-diylbis(oxy))(11S,11aS,11'S,11a'S)-bis(11-hydroxy-7-methoxy-2-methyl-5-oxo-11,11a-dihydro-1H-pyrrolo[2,1-c][1,4]benzodiazepine-10(5H)-carboxylate) (12)

EDCI.HCl (50 mg, 0.26 mmol, 3 eq.) was added to a stirred solution of bis-amine (9) (0.109 g, 86.5 μmol, 1.0 eq.) and MCOSu (40 mg, 0.19 mmol, 2.2 eq.) in CHCl$_3$ (10 mL). The reaction mixture was stirred at room temperature for 30 min then diluted with CHCl$_3$ (50 mL) washed with H$_2$O (100 mL), saturated brine (100 mL), dried (MgSO$_4$) and evaporated under reduced pressure. Purification by preparative HPLC followed by lyophilisation gave the product as a white foam (0.045 g, 32%). Analytical Data: LC/MS, RT 6.82 min; MS (ES$^+$) m/z (relative intensity) 1646 ([M+H]$^{+\bullet}$, 20); 1667 ([M+Na]$^{+\bullet}$, 30).

Example 4

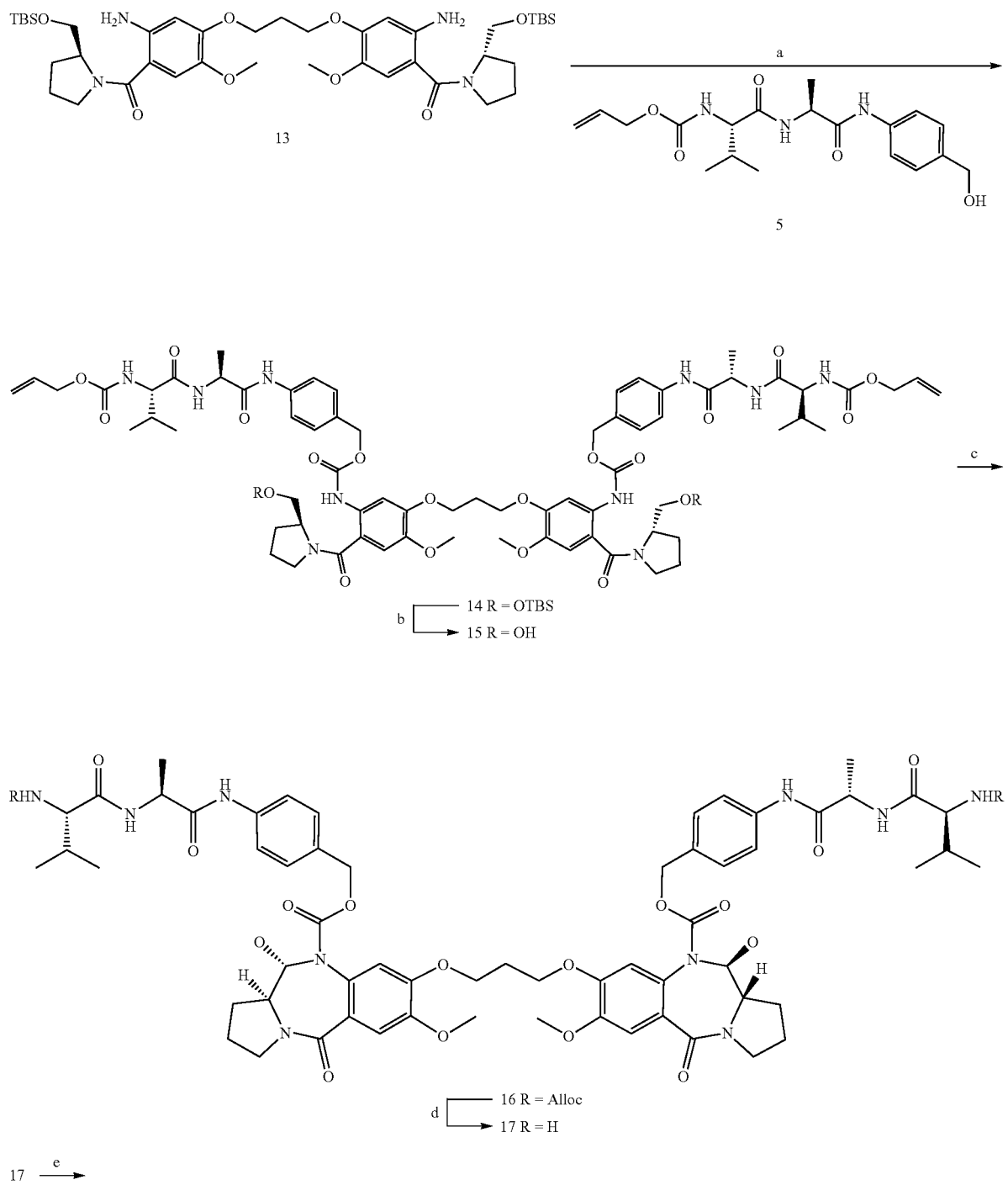

-continued

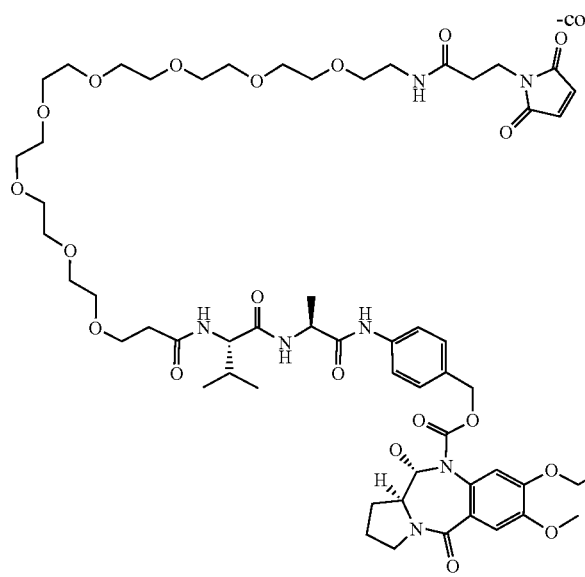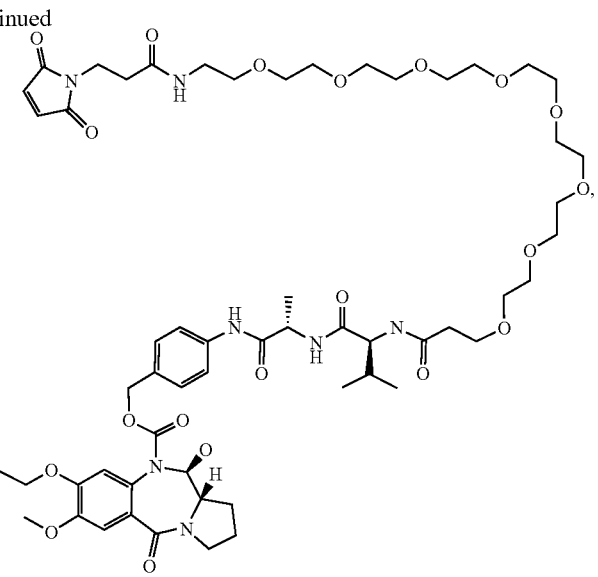

18

(a) bis(4-((S)-2-((S)-2-(((allyloxy)carbonyl)amino)-3-methylbutanamido)propanamido)benzyl) ((propane-1,3-diylbis(oxy))bis(6-((S)-2-(((tert-butyldimethylsilyl)oxy)methyl)pyrrolidine-1-carbonyl)-4-methoxy-3,1-phenylene))dicarbamate (14)

Triphosgene (472 mg, 1.59 mmol, 0.72 eq) was added in one portion to a mixture of 13 (1.77 g, 2.21 mmol) and triethylamine (1.35 mL, 9.69 mmol, 4.38 eq) in dichloromethane (3.6 mL). After 10 min, 5 (1.83 g, 4.85 mmol, 2.19 eq) was added in one portion as a fine powder, followed by triethylamine (0.68 mL, 4.9 mmol, 2.2 eq) and dibutyltin dilaurate (132 µL, 0.221 mmol, 0.1 eq) The reaction mixture was allowed to stir at 37° C. for 4 h, followed by stirring at room temperature overnight. The organic phase was washed with water and decanted in a filtration cartridge. The DCM was removed by evaporation, and the residue was dry loaded on silica gel, followed by chromatography with a 50 g ultra biotage cartridge (gradient DCM/DCM:MeOH 90:10, from 5% up to 32%, elution at 32%). The pure fractions were combined to yield the product 14 (2.35 g, 1.46 mmol, 66.2% Yield). Analytical Data: LC/MS, 3 min lipophilic method, RT 2.24 min; MS (ES$^+$) m/z (relative intensity) 1608.9 ([M+H]$^{+\cdot}$, 100);

(b) bis(4-((S)-2-((S)-2-(((allyloxy)carbonyl)amino)-3-methylbutanamido)propanamido)benzyl) ((propane-1,3-diylbis(oxy))bis(6-((S)-2-(hydroxymethyl)pyrrolidine-1-carbonyl)-4-methoxy-3,1-phenylene))dicarbamate (15)

Paratoluenesulfonic acid hydrate (277 mg, 1.46 mmol, 1 eq) was added in one portion to a mixture of 14 (2.34 g, 1.46 mmol) in tetrahydrofuran (53.0 mL) and water (5.00 mL) at 0° C. (ice/water bath). The reaction mixture was allowed to stir at 20° C. for 7 h until completion as monitored by LCMS. The reaction mixture was partitioned between ethyl acetate and water, and washed with NaHCO$_3$, then brine. The organics were dried over magnesium sulfate and concentrated under vacuum. The residue was purified by chromatography (50 g ultra, dry loaded on a samplet, DCM versus DCM:MeOH 90:10, gradient from 20% to 64%, elution around 64%. Pure fractions were combined and concentrated under vacuum to give the product 15 (1.60 g, 1.16 mmol, 79.7% Yield) as a white solid.

Analytical Data: LC/MS, 3 min lipophilic method, RT 1.50 min; MS (ES$^+$) m/z (relative intensity) 1380.9 ([M+H]$^{+\cdot}$, 100);

(c) bis(4-((S)-2-((S)-2-(((allyloxy)carbonyl)amino)-3-methylbutanamido)propanamido)benzyl) 8,8'-(propane-1,3-diylbis(oxy))(11S,11aS,11'S,11a'S)-bis(11-hydroxy-7-methoxy-5-oxo-2,3,11,11a-tetrahydro-1H-benzo[e]pyrrolo[1,2-a][1,4]diazepine-10(5H)-carboxylate) (16)

Stahl Tempo 0.2M Solution (2.10 mL, 0.420 mmol, 0.44 eq) followed by tetrakisacetonitrile copper(I) triflate (160 mg, 0.425 mmol, 0.44 eq) was added to a solution of 15 (1.32 g, 0.957 mmol) in DMF (4.00 mL) in a 500 mL flask. The reaction mixture was stirred rapidly and heated at 40° C. for 5 h, then 35° C. for 18 h under an air balloon, at which point completion was observed by LCMS. The solvents were removed by evaporation. Traces of DMF were removed by a second evaporation with butanone, followed by hard vacuum. The residue was dry loaded on a samplet (10 g) with acetone, followed by chromatography with a 50 g ultra column on a biotage isolera system. Gradient with 10% MeOH in DCM/DCM, from 20% up to 63% in 8 CV. Elution and hold around 60%. The impure front fractions were repurified using the same system on a 25 g column. All pure fractions were pooled. The residue was dissolved in acetone. Addition of heptane caused the precipitation of a white product. The volatiles were evaporated to leave the product 16 as a white powder after hard vacuum. (892 mg, 0.648 mmol, 67.8% Yield) Analytical Data: LC/MS, 3 min lipophilic method, RT 1.42 min; MS (ES$^+$) m/z (relative intensity) 1376.6 ([M+H]$^{+\cdot}$, 100);

(d) bis(4-((S)-2-((S)-2-amino-3-methylbutanamido) propanamido)benzyl) 8,8'-(propane-1,3-diylbis(oxy))(11S,11aS,11'S,11a'S)-bis(11-hydroxy-7-methoxy-5-oxo-2,3,11,11a-tetrahydro-1H-benzo[e] pyrrolo[1,2-a][1,4]diazepine-10(5H)-carboxylate) (17)

Tetrakis(triphenylphosphine)palladium(0) (10.0 mg, 0.00865 mmol, 0.034 eq) was added to a mixture of 16 (350 mg, 0.254 mmol) and pyrrolidine (65.0 µL, 0.780 mmol, 3.07 eq) in dichloromethane (7.50 mL) and methanol (0.5 mL). The reaction mixture was stirred under argon at room temperature for 1 h 30 minutes and was found complete by LCMS Ammonium chloride in water (30 mL, 34.3 mmol, 6 mass %) was added and the mixture was stirred vigorously. The mixture was then decanted in a biotage phase separation cartridge. The DCM layer was evaporated to dryness under vacuum. The residue was dissolved in chloroform (20 mL) and the solvent removed by evaporation under vacuum at 35° C. This cycle was repeated a second time, followed by drying under hard vacuum (3 mbar) to give the crude product 17 (307 mg, 0.254 mmol, 100%) as a white solid which was used directly in the next step without further purification. Analytical Data: LC/MS, 3 min lipophilic method, 2 peaks, RT 0.22 min; MS (ES$^+$) m/z (relative intensity) 604.9 ([M+2H]$^{2+\cdot}$, 100); 1208.2 ([M+H]$^{+\cdot}$, 10);

(e) bis(4-((2S,5S)-37-(2,5-dioxo-2,5-dihydro-1H-pyrrol-1-yl)-5-isopropyl-2-methyl-4,7,35-trioxo-10, 13,16,19,22,25,28,31-octaoxa-3,6,34-triazaheptatriacontanamido)benzyl) 8,8'-(propane-1,3-diylbis(oxy)) (11S,11aS,11'S,11a'S)-bis(11-hydroxy-7-methoxy-5-oxo-2,3,11,11a-tetrahydro-1H-benzo[e]pyrrolo[1,2-a][1,4]diazepine-10(5H)-carboxylate) (18)

Chloroform (10.00 mL) and methanol (0.4 mL) were added to crude 17 (307 mg, 0.254 mmol) followed by mal-amido-peg8-acid (339 mg, 0.561 mmol, 2.2 eq) and EDCI (107 mg, 0.558 mmol, 2.19 eq). The reaction was allowed to proceed at room temperature for 45 min when completion was observed by LCMS. Ammonium chloride in water (30 mL, 6 mass %) was added and the mixture was stirred vigorously. The mixture was decanted in a biotage phase separation cartridge. The DCM layer was evaporated to dryness under vacuum. The volatiles were removed by rotoevaporation and the crude residue was purified by chromatography (50 g Ultra, Biotage, gradient 30/70 to 100/0 of 16% MeOH in DCM/DCM in 10CV; Elution at more than 10% of MeOH). All fractions were analysed by TLC (10% MeOH in DCM). The pure fractions were pooled. The solvent was removed by evaporation to give 18 (200 mg). LCMS analysis showed traces of mal-peg8-acid, and the material was purified further by preparative HPLC, freeze-dried, aliquoted in dichloromethane, and dried under high vacuum to give 18 as a white solid. The purity was 99.45%. (B, 110 mg, 0.0467 mmol, 18.3% Yield). Analytical Data: LC/MS, 15 min method, RT 5.90 min; MS (ES$^+$) m/z (relative intensity) 1179.5 ([M+2H]$^{2+\cdot}$, 100); $^1$H NMR (400 MHz, DMSO-d6) δ 9.92 (s, 2H), 8.16 (d, J=6.9 Hz, 2H), 7.99 (t, J=5.7 Hz, 2H), 7.86 (d, J=8.7 Hz, 2H), 7.55 (s, 4H), 7.18 (s, 4H), 7.07 (s, 2H), 7.00 (s, 4H), 6.79 (s, 2H), 6.50 (s, 2H), 5.48 (s, 2H), 5.23-4.77 (m, 4H), 4.39 (t, J=7.0 Hz, 2H), 4.22 (dd, J=8.7, 6.6 Hz, 2H), 4.10 (s, 4H), 3.77 (s, 6H), 3.64-3.55 (m, 8H), 3.55-3.42 (m, 56H), 3.37 (t, J=5.9 Hz, 6H), 3.28 (t, J=8.3 Hz, 2H), 3.15 (q, J=5.8 Hz, 4H), 2.49-2.37 (m, 4H), 2.37-2.30 (m, 4H), 2.17 (s, 2H), 2.09-1.73 (m, 10H), 1.30 (d, J=7.0 Hz, 6H), 0.85 (dd, J=15.3, 6.7 Hz, 12H).

Example 5

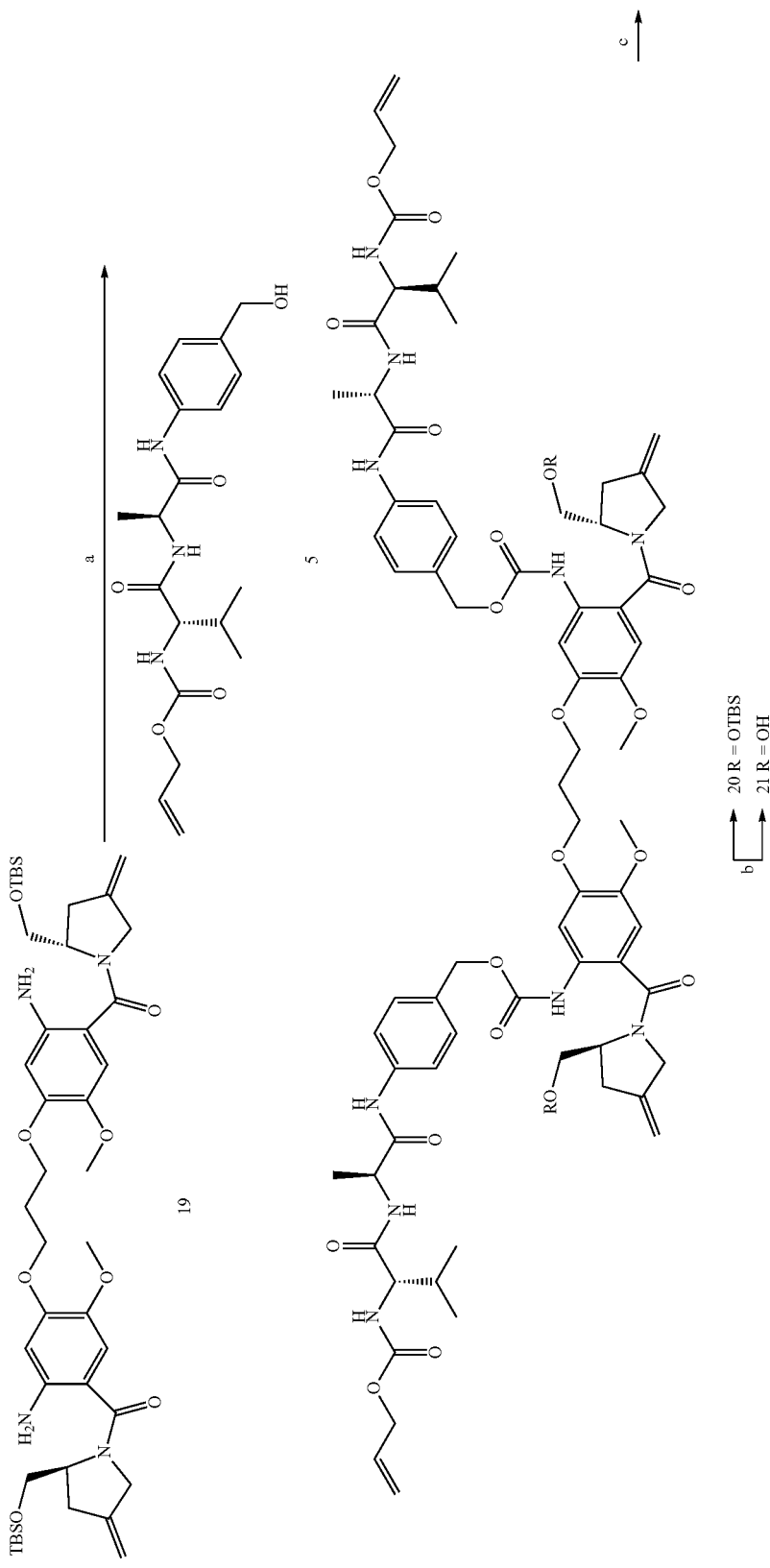

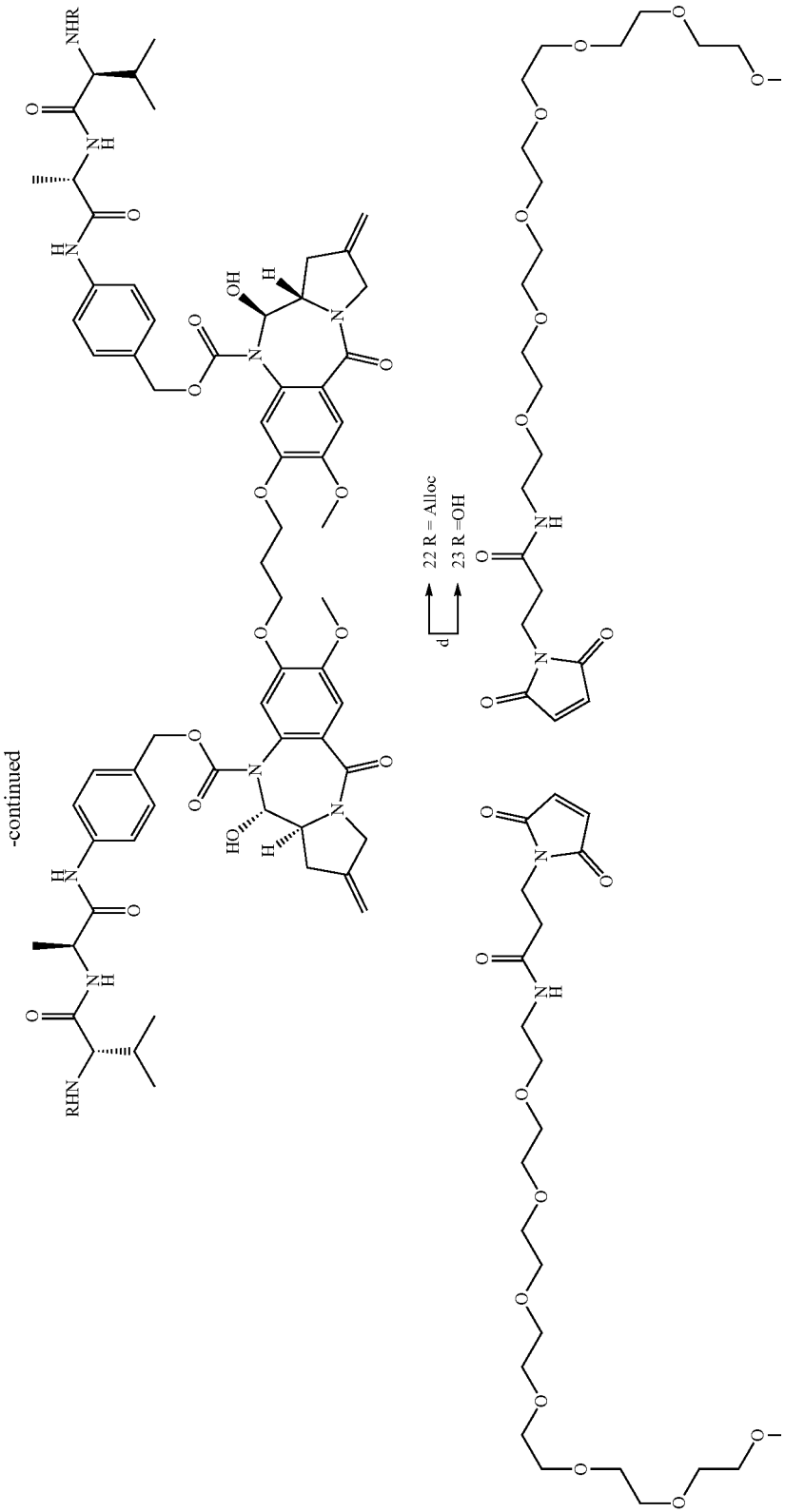

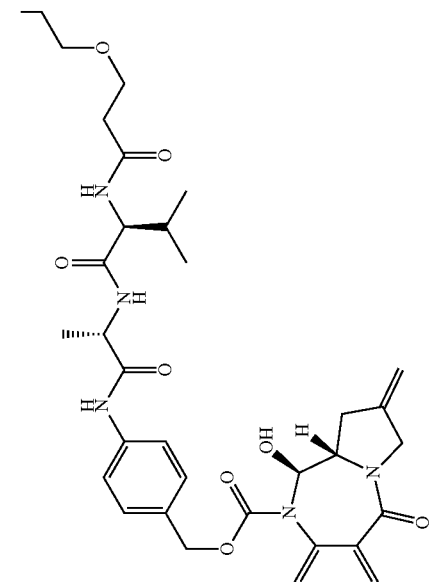
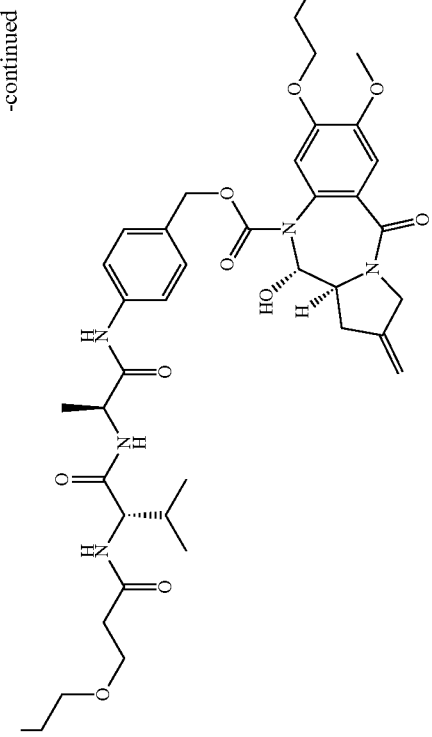

(a) bis(4-((S)-2-((S)-2-(((allyloxy)carbonyl)amino)-3-methylbutanamido)propanamido)benzyl) ((propane-1,3-diylbis(oxy))bis(6-((S)-2-(((tert-butyldimethylsilyl)oxy)methyl)-4-methylenepyrrolidine-1-carbonyl)-4-methoxy-3,1-phenylene))dicarbamate (20)

Triphosgene (816 mg, 2.75 mmol, 0.72 eq) was added in one portion to a mixture of 19 (3.15 g, 3.82 mmol) and triethylamine (2.34 mL, 16.8 mmol, 4.4 eq) in dichloromethane (75 mL) at 0° C. The ice batch was removed, and after 15 min, alcohol 5 (3.17 g, 8.40 mmol, 2.2 eq) was added in one portion as a fine powder, followed by triethylamine (1.17 mL, 8.39 mmol, 2.2 eq) and dibutyltin dilaurate (229 µL, 0.383 mmol, 0.1 eq). The reaction mixture was allowed to stir at 37° C. for 1 h, followed by stirring at room temperature overnight. The organic phase was diluted with DCM (100 mL) and washed with water (200 mL), saturated ammonium chloride (100 mL), and brine (50 mL), followed by drying over magnesium sulfate. The volatiles were removed by evaporation under reduced pressure. The crude product was dry-loaded on silica gel and eluted on a 340 g Ultra, with a gradient of ethyl acetate-acetone, from 20% up to 100% in 7CV. Rapid elution in 2CV at around 30% acetone gave pure fractions which were dried under vacuum to give 20 (4.00 g, 2.45 mmol, 100 mass %, 64.2% Yield). Analytical Data: LC/MS, 3 min lipophilic method, RT 2.34 min; MS (ES$^+$) m/z (relative intensity) 1661.1 ([M+H]$^{+\cdot}$, 100);

(b) bis(4-((S)-2-((S)-2-(((allyloxy)carbonyl)amino)-3-methylbutanamido)propanamido)benzyl) ((propane-1,3-diylbis(oxy))bis(6-((S)-2-(hydroxymethyl)-4-methylenepyrrolidine-1-carbonyl)-4-methoxy-3,1-phenylene))dicarbamate (21)

Bis-TBS ether 20 (4.00 g, 2.45 mmol) and paratoluenesulfonic acid hydrate (300 mg, 1.58 mmol) were dissolved in a mixture of 2-methyltetrahydrofuran (25.0 mL, 249 mmol, 100 mass %), acetic acid (4.00 mL, 69.8 mmol, 100 mass %) and water (4.00 mL, 222 mmol, 100 mass %). The mixture was heated at 40 C. After 2 h, completion was observed by LCMS. The reaction mixture was partitioned between ethyl acetate (150 mL) and water (200 mL), then washed with saturated NaHCO$_3$ (150 mL), and brine (100 mL). The organics were dried over magnesium sulfate and concentrated under vacuum. The residue was purified by chromatography (100 g ultra, dry loaded on 10 g samplet, ethyl acetate/acetone, gradient from 85/15 to 0/100, elution around 80% acetone. The pure fractions were combined and concentrated under vacuum to give the pure product 21 (960 mg, 0.684 mmol, 27.9% Yield) as a white solid. Analytical Data: LC/MS, 3 min lipophilic method, RT 1.54 min; MS (ES$^+$) m/z (relative intensity) 1402.3 ([M+H]$^{+\cdot}$, 100);

(c) bis(4-((S)-2-((S)-2-(((allyloxy)carbonyl)amino)-3-methylbutanamido)propanamido)benzyl) 8,8'-(propane-1,3-diylbis(oxy))(11S,11aS,11'S,11a'S)-bis(11-hydroxy-7-methoxy-2-methylene-5-oxo-2,3,11,11a-tetrahydro-1H-benzo[e]pyrrolo[1,2-a][1,4]diazepine-10(5H)-carboxylate) (22)

Stahl Tempo 0.2M Solution (1.34 mL, 0.268 mmol, 0.4 eq) followed by Tetrakisacetonitrile copper(I) triflate (190 mg, 0.504 mmol, 0.75 eq) was added to a solution of alcohol 21 (940 mg, 0.670 mmol) in DMF (3.00 mL) and DCM (13.0 mL) in a 500 mL flask. The reaction mixture was stirred rapidly and heated at 37° C. for 5 h (almost complete), followed by −20° C. for 96 h, at which point the reaction mixture was diluted with dichloromethane (60 mL) and water (60 mL) and stirred for 5 min. The reaction mixture was decanted in a phase separator and the DCM phase was dried under reduce pressure. MEK (60 mL) was added and the residual DMF was removed by azeotroping with MEK under reduce pressure (2 times) to give the crude product as a solid. This was redissolved in DCM/isopropanol 80/20 (5 to 10 mL) and loaded onto a Biotage samplet (10 g), dried and loaded on a 100 g Ultra column. Gradient from 88/12 DCM/20% MeOH in DCM up to 70/30 in 10 CV. The pure fractions were combined to give pure 22 (602 mg, 0.430 mmol, 64.2% Yield) as a white product. Analytical Data: LC/MS, 3 min lipophilic method, RT 1.51 min; MS (ES$^+$) m/z (relative intensity) 1401.5 ([M+H]$^{+\cdot}$, 100);

(d) bis(4-((S)-2-((S)-2-amino-3-methylbutanamido)propanamido)benzyl) 8,8'-(propane-1,3-diylbis(oxy))(11S,11aS,11'S,11a'S)-bis(11-hydroxy-7-methoxy-2-methylene-5-oxo-2,3,11,11a-tetrahydro-1H-benzo[e]pyrrolo[1,2-a][1,4]diazepine-10(5H)-carboxylate) (23)

Tetrakis(triphenylphosphine)palladium(0) (8.2 mg, 0.0071 mmol, 100 mass %) was added to a mixture of 22 (250 mg, 0.179 mmol) and pyrrolidine (37.0 µL, 0.444 mmol, 2.49 eq) in DCM (7.50 mL) and methanol (0.5 mL). The reaction mixture was stirred under argon at room temperature for 1 h 30 minutes and was found complete by LCMS.

Ammonium chloride in water (30 mL, 6 mass %) was added and the mixture was stirred vigorously. The mixture was then decanted in a biotage phase separation cartridge. The DCM layer was evaporated to dryness under vacuum. The residue was dissolved in chloroform (20 mL) and the solvent removed by rotoevaporation under vacuum at 35° C. This cycle was repeated a second time, followed by drying under hard vacuum (3 mbar, on rotoevaporator) to give the crude product 23 (220 mg, 0.179 mmol, 100%) as a white solid which was used directly in the next step without further purification. Analytical Data: LC/MS, 3 min method, 2 peaks, RT 1.15 min; MS (ES$^+$) m/z (relative intensity) 616.9 ([M+2H]$^{2+\cdot}$, 100); 1232.1 ([M+H]$^{+\cdot}$, 10).

(e) bis(4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl) 8,8'-(propane-1,3-diylbis(oxy))(11S,11aS,11'S,11a'S)-bis(11-hydroxy-7-methoxy-2-methylene-5-oxo-2,3,11,11a-tetrahydro-1H-benzo[e]pyrrolo[1,2-a][1,4]diazepine-10(5H)-carboxylate) (24)

Chloroform (4.1 mL) and methanol (0.2 mL) were added to 23, followed by mal-amido-peg8-acid (238 mg, 0.394 mmol, 2.2 eq) and EDCI (85.0 mg, 0.443 mmol, 2.48 eq). The reaction was allowed to proceed at room temperature for 45 min when completion was observed by LCMS. The reaction mixture was concentrated (2 mL), loaded on a 3 g biotage silica samplet and dried under vacuum. The samplet was loaded on a 25 g Ultra Biotage column, and eluted (gradient 10/90 to 58/42 of 20% MeOH in DCM/DCM in 12CV; Elution at around 55% of 20% MeOH). All fractions were analysed by TLC (10% MeOH in DCM). The pure fractions were pooled. The solvent was removed by evaporation to give 24 (250 mg, 0.105 mmol, 58.8% Yield).

Analytical Data: LC/MS, 15 min method, RT 6.20 min; MS (ES$^+$) m/z (relative intensity) 1191.5 ([M+2H]$^{2+•}$, 100); $^1$H NMR (400 MHz, DMSO-d6) δ 9.92 (s, 2H), 8.16 (d, J=6.9 Hz, 2H), 7.99 (t, J=5.5 Hz, 2H), 7.86 (d, J=8.6 Hz, 2H), 7.68-7.42 (m, 4H), 7.39-7.11 (m, 4H), 7.07 (s, 2H), 7.00 (s, 4H), 6.81 (s, 2H), 6.60 (s, 2H), 5.46-5.30 (m, 2H), 5.21-4.79 (m, 8H), 4.39 (t, J=7.0 Hz, 2H), 4.22 (dd, J=8.7, 6.7 Hz, 2H), 4.15-3.88 (m, 8H), 3.77 (s, 6H), 3.65-3.55 (m, 8H), 3.54-3.40 (m, 58H), 3.37 (t, J=5.9 Hz, 4H), 3.15 (q, J=5.8 Hz, 4H), 2.95-2.79 (m, 2H), 2.57-2.52 (m, 2H), 2.49-2.37 (m, 4H), 2.37-2.29 (m, 4H), 2.22-2.10 (m, 2H), 2.03-1.88 (m, 2H), 1.30 (d, J=7.0 Hz, 6H), 0.85 (dd, J=15.3, 6.7 Hz, 12H).

Example 6

(i) Synthesis of (S,E)-(2-(((tert-butyldimethylsilyl)oxy)methyl)-4-ethylidenepyrrolidin-1-yl)(5-methoxy-2-nitro-4-((triisopropylsilyl)oxy)phenyl)methanone (29)

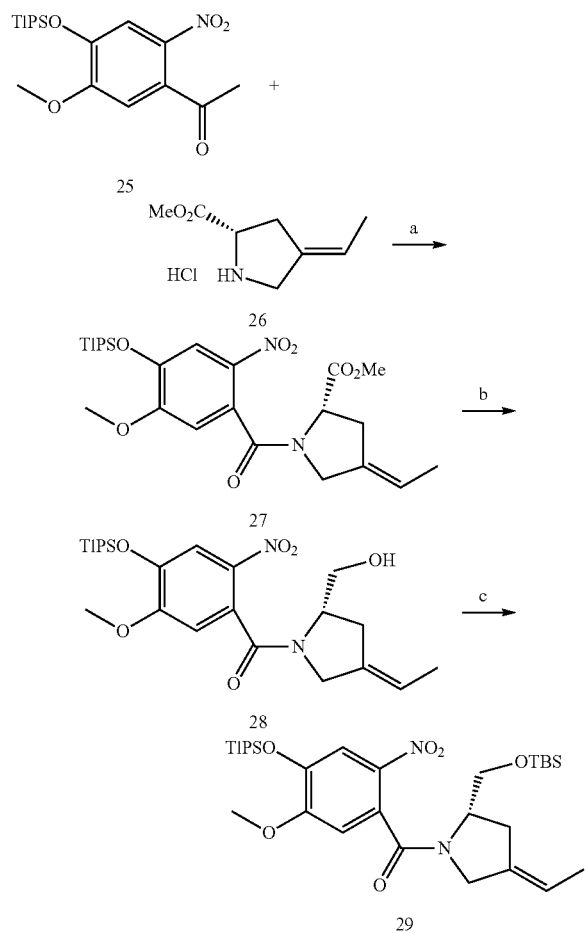

Compound 25 is described in Tiberghien et al, *ACS Med. Chem. Lett.*, 2016, 7 (11), pp 983-987. Compound 26 is described in Smits and Zemribo, *Org. Lett.*, 2013, 15 (17), pp 4406-4409.

(a) methyl(S,E)-4-ethylidene-1-(5-methoxy-2-nitro-4-((triisopropylsilyl)oxy)benzoyl)pyrrolidine-2-carboxylate (27)

25 (325 g, 1.2 eq) and 26 (1.0 eq.) were dissolved in DCM (3.25 L) and cooled to −40° C. T3P (2 eq) was added portionwise at −40° C., followed by DIEA (6.0 eq). The mixture was stirred for 1 h at −40° C. Reaction completion was observed by LCMS. Aqueous acetic acid (10%, 3.25 L) was added at 0° C. The organic phase was separated and washed a second time with aqueous acetic acid (10%, 3.25 L), followed by brine (3.25 L). The volatiles were removed under vacuum to leave the crude product 27 as a brown oil, which was purified by silica gel chromatography (petroleum ether/EtOAc, gradient from 100/1 to 10/1, collection from 20/1. (591 g, purity 87.6% by LC, 70% by NMR, yield=60%). RT: 6.374 min.

Analytical Method Used for Compound 27
Column: Agilent Poroshell 120 EC-C18 4.6*100 mm, 2.7 um
Mobile phase A: 0.05% TFA in Water
Mobile phase B: 0.05% TFA in ACN
Diluent: ACN
Flow rate: 1.0 mL/min
Injection volume: 1 μL
Column temperature: 40° C.
Detector: 220 nm
Run Time: 8.1 minutes
Post time: 2 minutes

| Gradient Table | | | | |
|---|---|---|---|---|
| Time (min) | 0.0 | 4.0 | 8.0 | 8.1 |
| % Mobile Phase A | 80 | 0 | 0 | 95 |
| % Mobile Phase B | 20 | 100 | 100 | 5 |

(b) (S,E)-(4-ethylidene-2-(hydroxymethyl)pyrrolidin-1-yl)(5-methoxy-2-nitro-4-((triisopropylsilyl)oxy)phenyl)methanone (28)

27 (591 g, 1 eq) was dissolved to DCM and cooled to 0° C. Lithium borohydride (2.0 eq) was added portionwise. The reaction mixture was stirred at 0° C. for 6 h. Reaction completion was observed by LCMS. Aqueous acetic acid (10%, 5.9 L) was added at 0° C. The organic phase was separated and washed a second time with aqueous acetic acid (10%, 5.9 L), followed by brine (5.9 L). The volatiles were removed under vacuum to leave a residue which was purified by flash chromatography (petroleum ether/EtOAc, gradient from 50/1 to 1/1. Collection from 5/1) to give 28 as an off white solid (250 g, 64% yield). RT: 7.922 min.

(c) (S,E)-(2-(((tert-butyldimethylsilyl)oxy)methyl)-4-ethylidenepyrrolidin-1-yl)(5-methoxy-2-nitro-4-((triisopropylsilyl)oxy)phenyl)methanone (29)

28 (250 g, 1 eq) and imidazole (2 eq) were dissolved in DCM (1.5 L, 6 V) at room temperature. TBSCl (1.5 eq) was added portionwise whilst keeping the temperature below 30° C. The reaction mixture was allowed to stir at 25° C. for 1 hour, when disappearance of starting material was observed by HPLC. The mixture was filtered through cotton wool. The filter cake was washed with DCM (500 mL). The filtrate was washed with aqueous acetic acid (10%, 2.5 L) at 10° C., followed by brine (2.5 L). The organic phase was dried with anhydrous sodium sulphate and concentrated under vacuum to give the product 29 as a yellow oil which was found sufficiently pure to be used in the next step (285 g, 92.2% yield). RT: 11.002 min. MS (ES$^+$) m/z (relative intensity) 663.4 ([M+H]$^{+•}$, 100);

Analytical Method Used for Compound 28 and 29
Column: Agilent Poroshell 120 EC-C18 4.6*100 mm, 2.7 um
Mobile phase A: 0.05% TFA in Water
Mobile phase B: 0.05% TFA in ACN
Diluent: ACN
Flow rate: 1.0 mL/min
Injection volume: 2 μL
Column temperature: 40° C.
Detector: 220 nm
Run Time: 12.1 minutes
Post time: 2 minutes

| Gradient Table | | | | |
|---|---|---|---|---|
| Time (min) | 0.0 | 6.0 | 12.0 | 12.1 |
| % Mobile Phase A | 80 | 0 | 0 | 80 |
| % Mobile Phase B | 20 | 100 | 100 | 20 |

(ii) Synthesis of bis(4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl) 8,8'-(pentane-1,5-diylbis(oxy)) (2E,2'E,11S,11 aS,11'S,11 a'S)-bis(2-ethylidene-11-hydroxy-7-methoxy-5-oxo-2,3,11,11 a-tetrahydro-1H-benzo[e]pyrrolo[1,2-a][1,4]diazepine-10(5H)-carboxylate) (37)

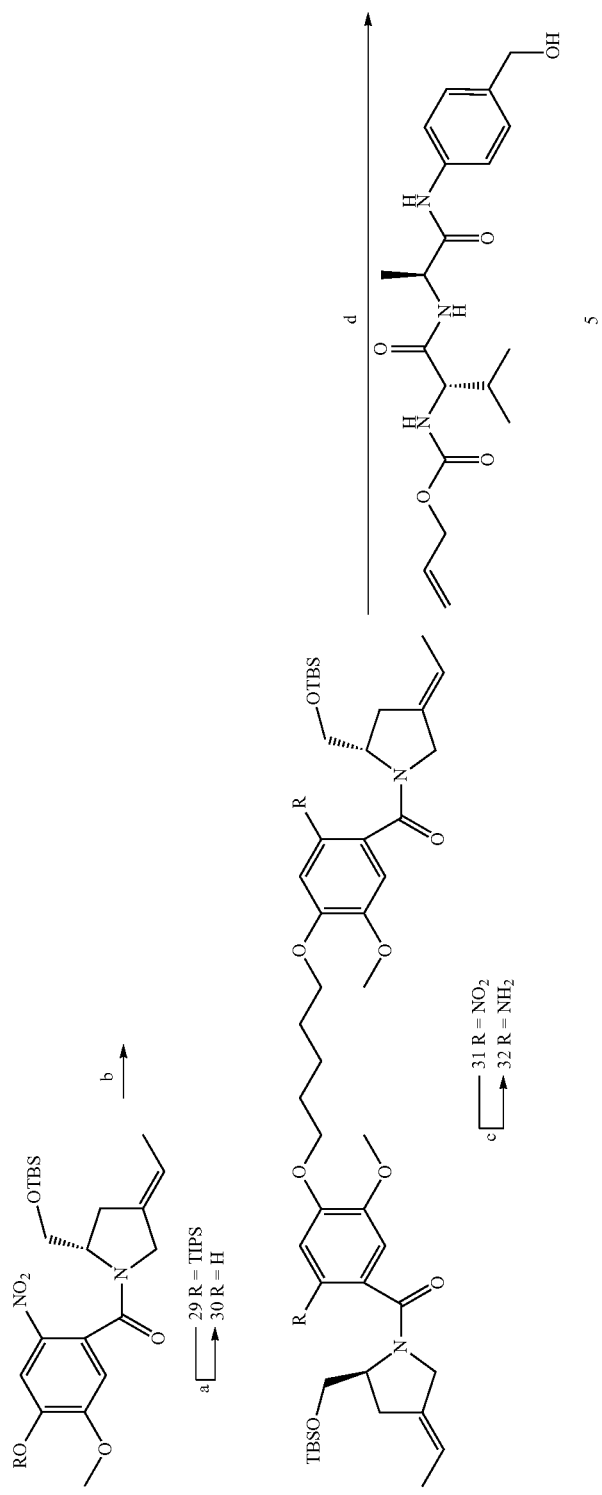

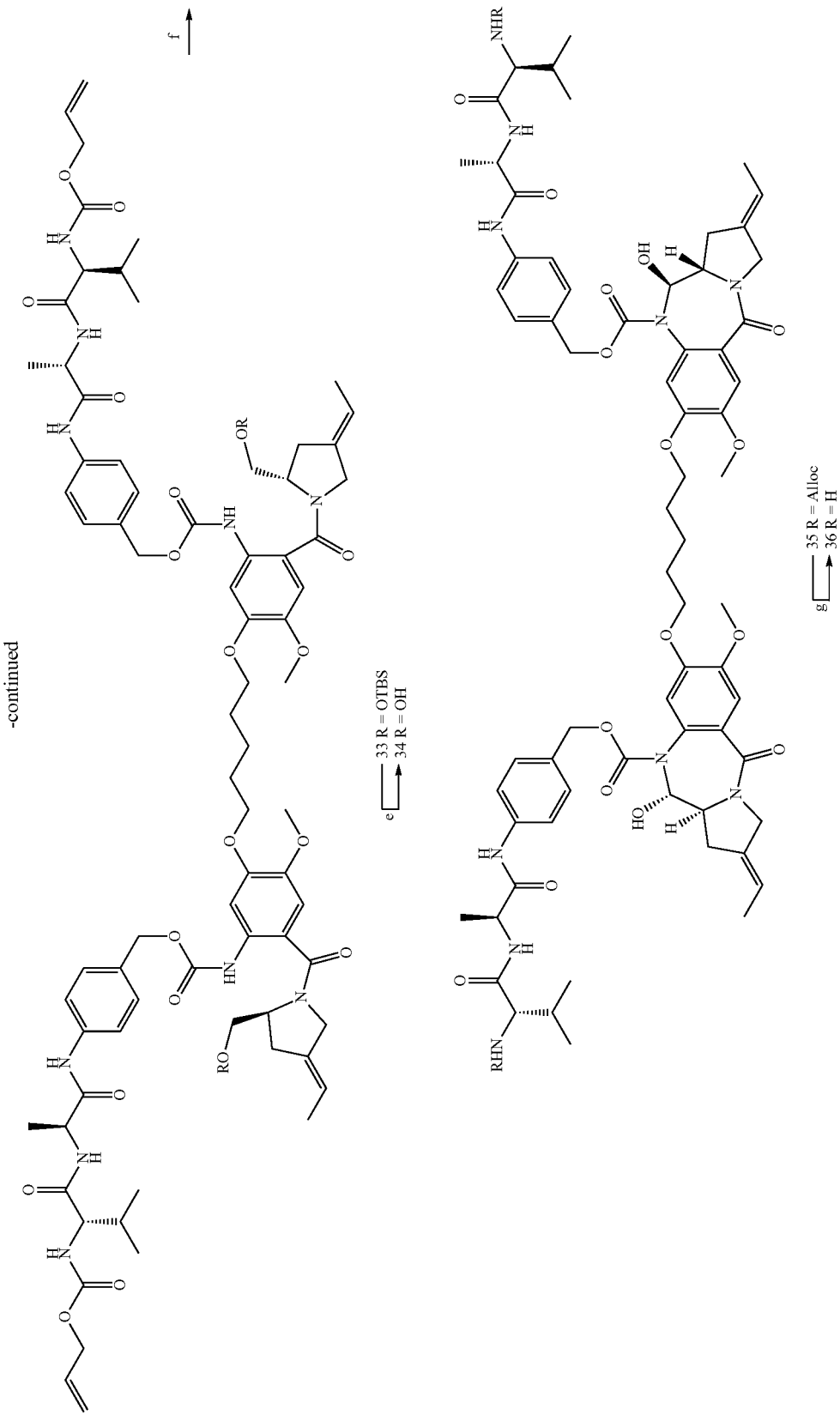

-continued
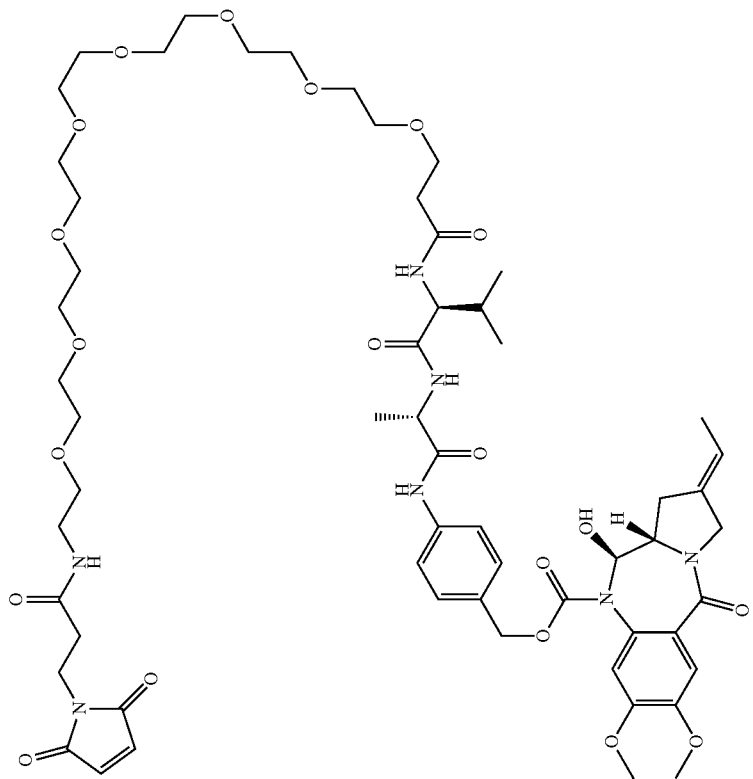
37
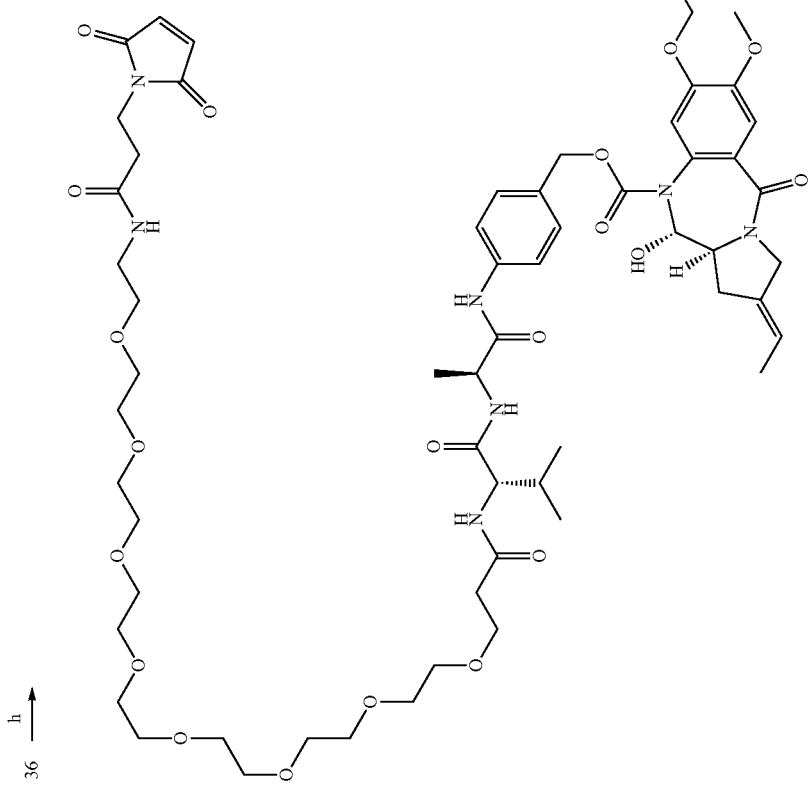
36

(a) (S,E)-(2-(((tert-butyldimethylsilyl)oxy)methyl)-4-ethylidenepyrrolidin-1-yl)(4-hydroxy-5-methoxy-2-nitrophenyl)methanone (30)

TIPS protected phenol 29 (10.0 g, 16.9 mmol) was dissolved in a mixture of ethyl acetate (20.0 mL) and DMF (20.0 mL) at 40° C. A solution of lithium acetate (0.668 g, 10.1 mmol, 0.6 eq) in water (3.0 mL) was added. The reaction was allowed to proceed at 40° C. for 4 h at which point completion was observed by LCMS. The reaction mixture was partitioned between 2-MeTHF (200 mL) and 2% citric acid in water (200 mL). The organic phase was washed with brine (70 mL) and dried over magnesium sulfate. The volatiles were removed under vacuum. The solid residue was precipitated by addition of diethyl ether (50 mL) and hexane (200 mL). The product was collected by filtration, washed with a little diethyl ether and dried overnight under vacuum to give 30 as a pale yellow solid. (5.8 g, 13 mmol, 79% Yield). Analytical Data: LC/MS, 3 min lipophilic method, RT 1.82 min; MS (ES$^+$) m/z (relative intensity) 437.8 ([M+H]$^{+•}$, 100);

(b) ((pentane-1,5-diylbis(oxy))bis(5-methoxy-2-nitro-4,1-phenylene))bis(((S,E)-2-(((tert-butyldimethylsilyl)oxy)methyl)-4-ethylidenepyrrolidin-1-yl)methanone) (31)

1,5-dibromopentane (0.986 g, 4.29 mmol, 0.5 eq) followed by potassium carbonate (1.30 g, 9.41 mmol, 1.1 eq) was added to a solution of 30 (3.74 g, 8.57 mmol) and tetrabutylammonium iodide (0.63 g, 1.7 mmol, 0.2 eq) in acetone (20.0 mL) in a 100 mL round-bottomed flask. The reaction mixture was stirred rapidly and heated at 60° C. for 2 h, and then allowed to stir at 45° C. overnight. The reaction was found complete by LCMS. The mixture was partitioned in ethyl acetate (150 mL) and water (200 mL, then washed with brine (100 mL), dried over magnesium sulfate. The volatiles were removed under vacuum to give the product 31 (4.04 g, 4.29 mmol, 100% Yield), which was used in the next step without further purification. Analytical Data: LC/MS, 3 min lipophilic method, RT 2.39 min; MS (ES$^+$) m/z (relative intensity) 942.3 ([M+H]$^{+•}$, 100);

(c) ((pentane-1,5-diylbis(oxy))bis(2-amino-5-methoxy-4,1-phenylene))bis(((S,E)-2-(((tert-butyldimethylsilyl)oxy)methyl)-4-ethylidenepyrrolidin-1-yl)methanone) (32)

Zinc (20.6 g, 315 mmol, 74 eq) was added to a mixture of ethanol (64.0 mL), water (4.00 mL), and formic acid (4.00 mL, 106 mmol, 25 eq) at 10° C. (ice bath), and stirred vigorously. To this mixture, a solution of 31 (4.00 g, 4.25 mmol) in ethanol (16.0 mL) was added dropwise with a pipette, whilst keeping the temperature below 35° C. The zinc mass was occasionally stirred manually. The reaction was allowed to proceed further for 30 min at room temperature, when completion was reached. The mixture was diluted with ethyl acetate (200 mL). The solids were removed by filtration over celite. The sinter was rinsed with ethyl acetate (200 mL). The filtrate was washed with water (300 mL), saturated sodium bicarbonate (150 mL), brine (100 mL), and dried over magnesium sulphate. The volatiles were removed by evaporation and the residue was purified by automated flash chromatography (100 g ultra, biotage, ethyl acetate/hexane gradient from 30% up 80% in 8 CV, elution from 58% from 10 CV, to give 32 (1.94 g, 2.20 mmol, 51.8% Yield) as a pale yellow foam. Analytical Data: LC/MS, 3 min lipophilic method, RT 2.29 min; MS (ES$^+$) m/z (relative intensity) 882.4 ([M+H]$^{+•}$, 100);

(d) bis(4-((S)-2-((S)-2-(((allyloxy)carbonyl)amino)-3-methylbutanamido)propanamido)benzyl) ((pentane-1,5-diylbis(oxy))bis(6-((S,E)-2-(((tert-butyldimethylsilyl)oxy)methyl)-4-ethylidenepyrrolidine-1-carbonyl)-4-methoxy-3,1-phenylene))dicarbamate (33)

Triphosgene (0.461 g, 1.55 mmol, 0.72 eq) was added in one portion to a mixture of 32 (1.90 g, 2.16 mmol) and triethylamine (1.32 g, 13.0 mmol, 6 eq) in DCM (45 mL) at 0° C. The ice batch was removed, and after 15 min, 5 (1.79 g, 4.74 mmol, 2.2 eq) was added in one portion as a fine powder, followed by triethylamine (0.661 g, 6.53 mmol, 3 eq) and dibutyltin dilaurate (0.129 mL, 0.215 mmol, 0.1 eq). The reaction mixture was allowed to stir at 37° C. for 4 h, followed by stirring at room temperature overnight. The organic phase was diluted with DCM (100 mL) and washed with water (200 mL), saturated ammonium chloride (100 mL), and brine (50 mL), followed by drying over magnesium sulfate. The volatiles were removed by evaporation under reduced pressure to give 3 (3.00 g, 1.78 mmol, 82% Yield). The crude product was reacted directly in the next step. Analytical Data: LC/MS, 3 min lipophilic method, RT 2.31 min; MS (ES$^+$) m/z (relative intensity) 1689.6 ([M+H]$^{+•}$, 100);

(e) bis(4-((S)-2-((S)-2-(((allyloxy)carbonyl)amino)-3-methylbutanamido)propanamido)benzyl) ((pentane-1,5-diylbis(oxy))bis(6-((S,E)-4-ethylidene-2-(hydroxymethyl)pyrrolidine-1-carbonyl)-4-methoxy-3,1-phenylene))dicarbamate (34)

Bis-TBS ether 33 (3.00 g, 1.78 mmol) was dissolved in a mixture of 2-methyltetrahydrofuran (9 mL), acetic acid (9 mL) and water (1.5 mL). The mixture was heated at 40° C. for 2 h. LCMS monitoring indicated an unsatisfactory rate of reaction (40%) completion. Paratoluenesulfonic acid hydrate (203 mg, 1.07 mmol, 0.6 eq) was added, which accelerated the reaction. Completion was observed in 30 min.

The reaction mixture was partitioned between ethyl acetate (150 mL) and water (200 mL), then washed with saturated NaHCO$_3$ (150 mL), and brine (100 mL). The organics were dried over magnesium sulfate and concentrated under vacuum. The residue was purified by chromatography (50 g ultra, dry loaded on loose silica gel, ethyl acetate/acetone, gradient from 85/15 to 0/100, elution around 55% acetone. Pure fractions were combined and concentrated under vacuum to give the pure product 34 (2.20 g, 1.51 mmol, 84.8% Yield) as a white solid. Analytical Data: LC/MS, 3 min lipophilic method, RT 1.67 min; MS (ES$^+$) m/z (relative intensity) 1461.6 ([M+H]$^{+•}$, 100);

(f) bis(4-((S)-2-((S)-2-(((allyloxy)carbonyl)amino)-3-methylbutanamido)propanamido)benzyl) 8,8'-(pentane-1,5-diylbis(oxy))(2E,2'E,11S,11aS,11'S,11a'S)-bis(2-ethylidene-11-hydroxy-7-methoxy-5-oxo-2,3,11,11a-tetrahydro-1H-benzo[e]pyrrolo[1,2-a][1,4]diazepine-10(5H)-carboxylate) (35)

Stahl Tempo 0.2M Solution (3.50 mL, 0.700 mmol, 0.47 eq) followed by tetrakisacetonitrile copper(I) triflate (290 mg, 0.770 mmol, 0.52 eq) was added to a solution of 34 (2.17 g, 1.49 mmol) in DMF (3.00 mL) in a 500 mL flask.

The reaction mixture was stirred rapidly and heated at 40° C. for 5 h (completion), followed by 30° C. for 18 h under an air balloon, at which point the reaction mixture was diluted with dichloromethane (60 mL) and water (60 mL) and stirred for 5 min. The reaction mixture was decanted in a phase separator and the DCM phase was dried under reduce pressure. MEK (60 mL) was added and the residue DMF was removed by azeotroping under reduce pressure (2 times) to give the crude product as a solid. This was redissolved in DCM (5 to 10 mL) and loaded on a 100 g Ultra column. Gradient from 75/25 DCM/10% MeOH in DCM up to 40/60 (elution around 50/50). The pure fractions were combined to give 35 (1.35 g, 0.927 mmol, 62.4% Yield) as a white product. Analytical Data: LC/MS, 3 min lipophilic method, RT 1.63 min; MS (ES$^+$) m/z (relative intensity) 1457.3 ([M+H]$^{+*}$, 100); 15 min method, RT 7.52 min; MS (ES$^+$) m/z (relative intensity) 1456.6 ([M+H]$^{+*}$, 100);

(g) bis(4-((S)-2-((S)-2-amino-3-methylbutanamido) propanamido)benzyl) 8,8'-(pentane-1,5-diylbis(oxy)) (2E,2'E,11S,11aS,11'S,11a'S)-bis(2-ethylidene-11-hydroxy-7-methoxy-5-oxo-2,3,11,11a-tetrahydro-1H-benzo[e]pyrrolo[1,2-a][1,4]diazepine-10(5H)-carboxylate) (36)

Tetrakis(triphenylphosphine)palladium(0) (10.0 mg, 0.0086 mmol, 0.01 eq) was added to a mixture of 35 (1.33 g, 0.914 mmol) and pyrrolidine (190 µL, 2.28 mmol, 2.5 eq) in DCM (7.50 mL) and methanol (0.5 mL). The reaction mixture was stirred under argon at room temperature for 1 h 30 minutes and was found complete by LCMS. Ammonium chloride in water (30 mL, 6 mass %) was added and the mixture was stirred vigorously. The mixture was then decanted in a biotage phase separation cartridge. The DCM layer was evaporated to dryness under vacuum. The residue was dissolved in chloroform (20 mL) and the solvent removed by evaporation under vacuum at 35° C. This cycle was repeated a second time, followed by drying under hard vacuum (3 mbar) to give crude 36 (1.17 g, 0.914 mmol, 100% Yield) as white solid. Analytical Data: LC/MS, 3 min method, RT 1.23 min, 2 peaks; MS (ES$^+$) m/z (relative intensity) 645.0 ([M+2H]$^{2+*}$, 100); 1288.8 ([M+H]$^{+*}$, 10).

(h) bis(4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl) 8,8'-(pentane-1,5-diylbis(oxy)) (2E,2'E,11S,11aS,11'S,11a'S)-bis(2-ethylidene-11-hydroxy-7-methoxy-5-oxo-2,3,11,11a-tetrahydro-1H-benzo[e]pyrrolo[1,2-a][1,4]diazepine-10(5H)-carboxylate) (37)

DCM (10.00 mL) and methanol (0.4 mL) were added to 36 (393 mg, 0.305 mmol), followed by mal-amido-peg8-acid (380 mg, 0.628 mmol, 2.06 eq) and EDCI (128 mg, 0.668 mmol, 2.2 eq). The reaction was allowed to proceed at room temperature for 4 h when completion was observed by LCMS. Ammonium chloride in water (30 mL, 6 mass %) was added and the mixture was stirred vigorously. The mixture was decanted in a biotage phase separation cartridge. The DCM layer was evaporated to dryness under vacuum and the crude residue was purified by chromatography (25 g Ultra gradient 15/85 to 100/0 of 20% MeOH in DCM/DCM in 12CV; hold at elution around 48%). The fractions were analysed by TLC (10% MeOH in DCM). The pure fractions were pooled. The solvent was removed by evaporation. The residue was purified further by reverse phase preparative HPLC (gradient 15 to 75% water/acetonitrile+0.01% formic acid) followed by freeze-drying and aliquoted from DCM to give 37 (516 mg, 0.212 mmol, 69.4% Yield) as a white foam. The purity was 97.65%. Analytical Data: LC/MS, 15 min method, RT 6.61 min; MS (ES$^+$) m/z (relative intensity) 1219.7 ([M+2H]$^{2+*}$, 100); $^1$H NMR (400 MHz, DMSO-d6) δ 9.92 (s, 2H), 8.17 (d, J=6.9 Hz, 2H), 8.01 (t, J=5.6 Hz, 2H), 7.87 (d, J=8.7 Hz, 2H), 7.72-7.44 (m, 4H), 7.39-7.10 (m, 4H), 7.05 (s, 2H), 7.00 (s, 4H), 6.76 (s, 2H), 6.66-6.46 (m, 2H), 5.56 (d, J=7.1 Hz, 2H), 5.34 (dd, J=9.7, 5.9 Hz, 2H), 5.21-4.70 (m, 4H), 4.39 (t, J=7.0 Hz, 2H), 4.22 (dd, J=8.7, 6.7 Hz, 2H), 4.15-4.01 (m, 2H), 3.94 (d, J=15.3 Hz, 4H), 3.86-3.72 (m, 8H), 3.60 (t, J=7.3 Hz, 8H), 3.55-3.42 (m, 58H), 3.37 (t, J=5.9 Hz, 4H), 3.15 (q, J=5.8 Hz, 4H), 2.76-2.56 (m, 4H), 2.46 (t, J=6.8 Hz, 2H), 2.40 (t, J=6.5 Hz, 2H), 2.36-2.29 (m, 4H), 1.96 (q, J=6.7 Hz, 2H), 1.78 (s, 4H), 1.66 (d, J=6.6 Hz, 6H), 1.57 (d, J=8.6 Hz, 2H), 1.30 (d, J=7.0 Hz, 6H), 0.85 (dd, J=15.2, 6.7 Hz, 12H).

Production of Herceptin-Flexmab and NIP228-Flexmab Antibodies

General

Cell lines SKBR-3 (HER2$^+$, 1.5×10$^6$ receptors/cell), MDA-MB-453 (HER2$^+$, 7.7×10$^4$ receptors/cell), and MCF-7 (HER2$^-$) were obtained from ATCC and maintained in T175 tissue culture flasks (Corning) using the manufacturer's recommended media (SKBR-3: McCoys 5A+10% FBS, MDA-MB-453: DMEM+10% FBS, and MCF-7: DMEM+10% FBS). 293F cells (Invitrogen) used for transfection were maintained in 293F Freestyle media (Invitrogen). SKBR-3, MDA-MB-453, and MCF-7 cells were cultured in a 37° C. incubator with 5% CO$_2$. 293F cells were cultured in shake flasks (2 L, Corning) at 37° C. with 8% CO$_2$ and rotation at 120 rpm. All reagents were purchased from Sigma Aldrich, VWR, or JT Baker unless otherwise specified and used without additional purification.

Design and Construction of Herceptin-Flexmab and NIP228-Flexmab Antibodies

Figure 3:
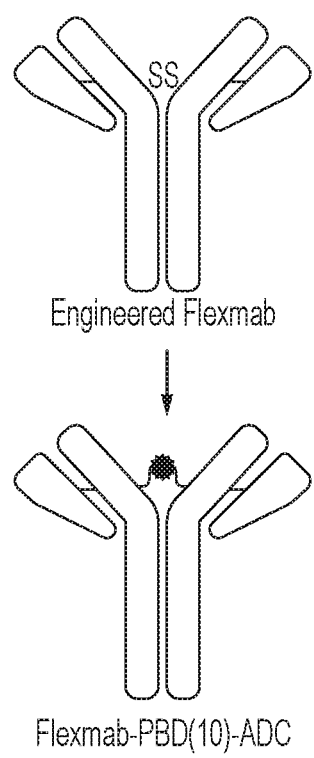
FIG. 3 shows schematic representations of (A) modified antibodies suitable for use in the present invention, (B) an antibody drug conjugate comprising a PBD of the present invention.

The Herceptin wild-type antibody was used as the template to engineer the Herceptin-Flexmab. The light chain of the Herceptin-Flexmab consists of two mutations, F118C and C214V, whereas the heavy chain contains three mutations, L124C, C216V, and C225V (see FIGS. 3 and 5—in FIG. 5, C represent engineered cysteines, V represent cysteine to valine mutations and C represents cysteine used for conjugation/rebridging). The F118C mutation in the light chain forms a disulfide bond with the L124C mutation in the heavy chain. This engineered disulfide is not solvent exposed, but serves to preserve the covalent linkage between the light and heavy chains. The C222 hinge cysteine was left unmodified and served as the location for site-specific conjugation with the pBD-based drug linker. The light chain and heavy chain sequences for the Herceptin-Flexmab were codon-optimized for mammalian expression and procured from GeneArt (Life Technologies). The optimized Herceptin-Flexmab construct was subcloned with standard molecular biology techniques using the BssHII/NheI sites (light chain) and the SalI/NotI sites (heavy chain) into a MedImmune proprietary mammalian expression vector which contains an IgG light chain signal peptide for secretion and cytomegalovirus promoters for recombinant expression. The completed mammalian expression plasmid, pOE-Herceptin-Flexmab was confirmed by DNA sequencing. The negative control NIP228-Flexmab antibody was generated as described for the Herceptin-Flexmab while using the wild-type NIP228 antibody (MedImmune proprietary) as a template.

Expression and Purification of Herceptin-Flexmab and NIP228-Flexmab Antibodies

Expression and purification of Herceptin-Flexmab and NIP228-Flexmab antibodies was conducted according to previously published methods (Dimasi, N., et al., *Journal of Molecular Biology*, 2009, 393, 672-692; DOI: 10.1016/j.jmb.2009.08.032). Following transient 293F expression and protein-A purification, the antibodies were formulated into conjugation buffer (1× PBS, 0.1 mM EDTA, pH 7.2) using Slide-A-Lyzer dialysis cassettes at 4° C. (10 kDa MWCO, Thermo) and concentrated to 8.0 mg/mL (Herceptin-Flexmab) and 5.52 mg/mL (NIP228-Flexmab) using Vivaspin concentrators (10 kDa MWCO, GE Healthcare). Final concentrations were determined using a Nanodrop spectrophotometer ($A_{280}$, Thermo). Transient expression yields after 6 days were 500 mg/L and 150 mg/L for Herceptin-Flexmab and NIP228-Flexmab, respectively.

Example 7—Construction of Herceptin-Flexmab and NIP228-Flexmab ADCs

Figure 4:
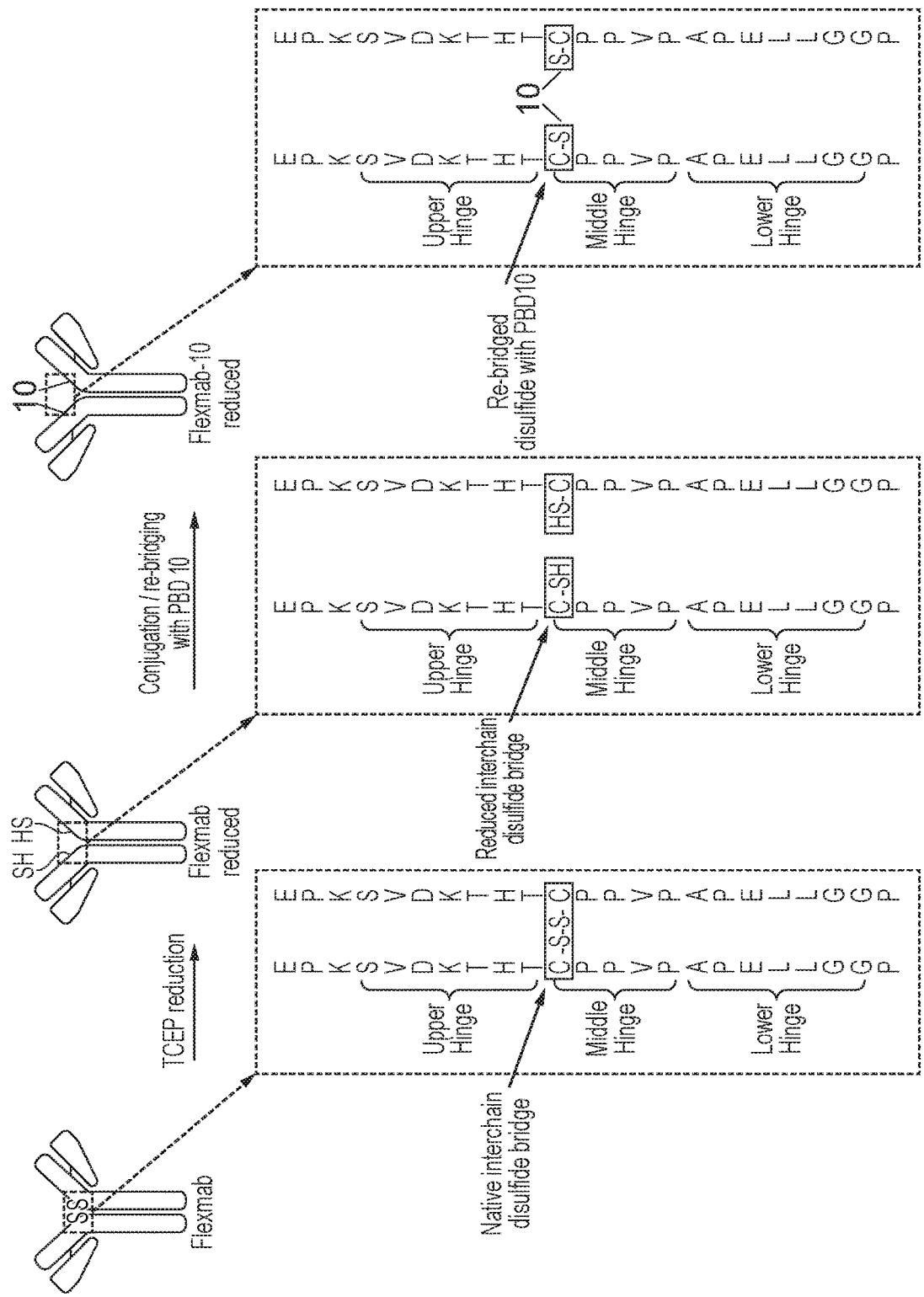
FIG. 4 shows a schematic representation of the conjugation of a modified antibody to Compound 10.

Herceptin-Flexmab (15 mg, 100 nmoles) in conjugation buffer (1× PBS, 1 mM EDTA, pH 7.2, 3 mL) was reduced using TCEP (3 eq., 300 nmoles, Thermo) for 2 h at room temperature. Following reduction, DMSO (10% v/v, 300 µL) was added to the reduced antibody, followed by the addition of compound 10 (3 eq., 300 nmoles). The conjugation reaction was allowed to proceed at room temperature for 3 h. Excess compound 10 was quenched using N-acetyl cysteine (5 eq. over compound 10, 1.5 µmoles, Sigma Aldrich) and the ADC was dialyzed against three buffer exchanges of conjugation buffer at 4° C. using a Slide-A-Lyzer dialysis cassette (10 kDa MWCO, Thermo). The ADC was diluted 1:5 with DI-$H_2O$ and loaded onto a type II ceramic hydroxyapatite column (Bio-Rad) at 5 mL/min using an AKTA Pure FPLC (GE Healthcare) and the column was washed with 20 column volumes of CHT buffer A (10 mM $NaPO_3$, pH 7). Elution of the ADC was performed using a linear gradient of CHT buffer B (0-2 M NaCl in 10 mM $NaPO_3$, pH 7) over 20 mins. The eluted ADC was dialyzed overnight at 4° C. into conjugation buffer using a Slide-A-Lyzer dialysis cassette (10 kDa MWCO) and diluted 1:5 with HIC buffer A (25 mM Tris-HCl, 1.5M $(NH_4)_2 SO_4$, pH 8). The ADC was loaded onto a semi-preparative hydrophobic interaction chromatography (HIC) column (HiTrap Butyl-S FF, GE Healthcare) at 1 mL/min using an AKTA Pure FPLC and washed with 20 column volumes of HIC buffer A. The ADC was eluted using a linear gradient of HIC buffer B (25 mM Tris-HCl, 5% isopropyl alcohol) over 45 mins at 1 mL/min. Purified Herceptin-Flexmab-10 was dialyzed into conjugation buffer overnight at 4° C., concentrated using a Vivaspin concentrator (10 kDa MWCO) to 2 mg/mL, and sterile filtered through a 0.2 µm syringe filter (Pall Corporation). The process is shown schematically in FIG. 4. The highlighted V's represent valine mutations.

The site-specific conjugation of compound 10 to NIP228-Flexmab and subsequent purification was performed as described for Herceptin-Flexmab-10.

Example 8—Analytical Characterization of ADCs

SDS-PAGE

SDS-PAGE was used to confirm the molecular weights of the Herceptin-Flexmab, Herceptin-Flexmab-10, NIP228-Flexmab, and NIP228-Flexmab-10 constructs. Samples (2 µg, parental or conjugated) were mixed 1:4 with LDS Bolt sample buffer (Invitrogen), 1:10 with NuPAGE reducing buffer (Invitrogen), and heated to 70° C. for 10 minutes followed by loading into a 10% Bis-tris Bolt gel (Invitrogen). Gels were electrophoresed at 150 V and stained using Simply Blue staining reagent (Invitrogen) and destained using DI-$H_2O$. Gels were imaged using a Gel Doc EZ Imaging system (Bio-RAD).

Reduced SDS-PAGE was used to confirm molecular weight of the purified Herceptin-Flexmab and NIP228-Flexmab antibodies and ADCs. The results demonstrates separation of light (LC) and heavy chains (HC) of the Herceptin-Flexmab with molecular weights of ~25 kDa and 50 kDa, respectively. Conjugation of the dual-maleimide compound 10 payload to the Herceptin-Flexmab resulted in very efficient bridging of the heavy chains with the presence of a 100 kDa band. Similar results were observed with the NIP228-Flexmab, with clear identification of the light and heavy chains under reducing conditions. Highly efficient disulfide bridging of the NIP228-Flexmab heavy chains with compound 10 was observed. No aggregation was observed for either antibody or ADC.

Hydrophobic Interaction Chromatography

Analytical hydrophobic interaction chromatography was used to assess the conjugation efficiencies of compound 10 onto the Herceptin-Flexmab and NIP228-Flexmab antibodies and to evaluate drug-to-antibody ratios (DARs) for each ADC. ADCs (500 µg in 50 µL) were individually loaded onto a Proteomix HIC Butyl-NP5 column (4.6 mm I.D.×3.5 cm×5 µm, Sepax) using HIC buffer A (25 mM Tris-HCl, 1.5M (NH4)2 SO4, pH 8) and the ADCs were eluted using a linear gradient of HIC buffer B (25 mM Tris-HCl, 5% isopropyl alcohol, pH 7, 5-100%) over 13 mins at 0.8 mL/min. Absorbance was measured at 280 nm and 330 nm and eluted peaks were manually integrated to determine conjugation efficiency of each ADC. Conjugation efficiencies and DARs were calculated based on Equation 1 and Equation 2, respectively.

$$\text{Conjugation Efficiency} = \left[ \frac{Area_{Conjugated}}{(Area_{Unconjugated} + Area_{Conjugated})} \right] \times 100 \quad \text{Equation 1}$$

$$DAR = \left[ \frac{Area_{DAR1} + 2(Area_{DAR2}) + n(Area_{DAR\ldots n})}{(Area_{DAR0} + Area_{DAR1} + Area_{DAR2} + Area_{DAR\ldots n})} \right] \quad \text{Equation 2}$$

| ADC | $Area_{DAR0}$ | $Area_{DAR1}$ | $Area_{DAR2}$ | $Eff_{conj}$ | DAR |
|---|---|---|---|---|---|
| Herceptin-Flexmab3-10 | 138.4 | 1285.9 | N/A | 90.3 | 0.90 |
| NIP228-Flexmab3-10 | 118.1 | 1191.4 | N/A | 90.1 | 0.90 |

Size-Exclusion Chromatography

Size-exclusion chromatography HPLC (SEC-HPLC) was conducted on the parental antibodies and ADCs to analyze purity and aggregation using an Agilent 1200 series HPLC. Samples (100 µg in 100 µL conjugation buffer) were injected onto a TSK Gel column (G3000SW, 8 mm I.D.×30 cm×5 µm, Tosoh Bioscience) using 0.1 M $NaPO_4$, 0.1M $NaSO_4$, 10% isopropanol, pH 6.8 as the mobile phase at a flow rate of 1 mL/min. Absorbance of eluted peaks were measured at $280_{nm}$ followed by manual integration to determine purity and percent aggregation of each sample.

Following protein A purification, each antibody yielded high monomeric contents in excess of 98%, and these characteristic were maintained following the conjugation of the compound 10 payload to generate the DAR=1 ADCs.

The Herceptin-Flexmab and Herceptin-Flexmab-10 eluted with retention times ($T_R$) of 8.65 mins and 8.66 mins, and 9.01 mins, respectively. The NIP228-Flexmab and NIP228-Flexmab-10 eluted with a $T_R$=8.52 mins and 8.54 mins respectively.

Reduced Reverse-Phase HPLC

To confirm site-specific conjugation of compound 10 onto the heavy chain of the antibodies, reduced reverse-phase HPLC (rRP-HPLC) was utilized. ADCs were treated with dithiothreitol (DTT, 50 mM) for 30 minutes at room temperature. Following reduction, the ADCs were injected onto a PLRP-S column (1000 Å, 2.1 mm×50 mm, Agilent) and eluted using a gradient mobile phase of RP-HPLC solvent A (0.1% trifluoroacetic acid in water) and RP-HPLC solvent B (0.1% trifluoroacetic acid in acetonitrile) consisting of 5% solvent B-100% solvent B over 25 mins. Gradient elutions were conducted at 80° C. using a flow rate of 1 mL/min. Absorbance was measured at $280_{nm}$.

The chromatograms of the Herceptin-Flexmab and Herceptin-Flexmab-10 ADC were overlaid. The light chains of both species co-eluted (Herceptin-Flexmab-10 $T_R$=17.57 mins; Herceptin-Flexmab $T_R$=17.54 mins), however there was a marked shift in retention time for the heavy chain of the Herceptin-Flexmab-10 ($T_R$=21.31 mins) when compared to the unconjugated Herceptin-Flexmab antibody ($T_R$=19.75 mins). A small amount of unconjugated heavy chain was also visible on the Herceptin-Flexmab-10 chromatogram ($T_R$=19.97 mins).

The chromatograms for the negative controls NIP228-Flexmab and NIP228-Flexmab-10 were also overlaid for comparative analysis. The heavy chain of the NIP228-Flexmab-10 ADC showed a shift in retention time ($T_R$=21.57 mins) when compared to the heavy chain of the NIP228-Flexmab ($T_R$=20.09 mins). A small amount of unconjugated heavy chain was visible for the NIP228-Flexmab-10 ($T_R$=20.35 mins).

Mass Spectrometry

Intact and reduced reverse-phase liquid chromatography mass spectrometry (LCMS) was utilized to confirm molecular weights of the Herceptin-Flexmab and NIP228-Flexmab antibodies and ADCs. Approximately 2 μg (4 μL) of antibody or ADC was injected onto an Agilent 1200 series HPLC connected in series to an Agilent 6520 Accurate-Mass Time-of-Flight (TOF) LC-MS. The antibody or ADC was loaded onto a Zorbax 300 Diphenyl Rapid Resolution HD column (2.1 mm×50 mm×1.8 μm) and eluted using a flow rate of 0.5 mL/min consisting of a step gradient of 1-80% Solvent B (0.1% formic acid in acetonitrile) after 2 mins (Solvent A: 0.1 formic acid in water). Data was acquired and analyzed using MassHunter software (Agilent).

Purified Herceptin-Flexmab produced a peak at 147, 985.36 Da (G0f calc: 147,980.8 Da). Following conjugation of the compound 10 payload (MW: 2408.67 Da), LCMS revealed the molecular weight of the Herceptin-Flexmab3-10 as 150,396.71 Da (G0f calc: 150,394.03 Da). Analysis of the NIP228-Flexmab by LCMS revealed a peak at 146, 770.36 Da (G0f calc: 146743.98 Da). Conjugation of the compound 10 payload produced a peak with MW of 149, 199.75 Da (G0f calc: 149,152.65 Da).

Differential Scanning Calorimetry (DSC)

Antibodies and ADCs were extensively dialyzed into 25 mM Histidine pH 6 at 4° C. and formulated at 0.5 mg/mL. DSC experiments were carried out using a MicroCal VP-DSC instrument (Malvern). The raw data was normalized for concentration and scan rate (1° C./min). Data analysis and deconvolution were carried out using the Origin 7 software (Malvern). Deconvolution analysis was conducted using a non-two-state model and the best fits were obtained using 10-15 iteration cycles. The denaturation temperatures, Tm, corresponding to the maximum of the transition peaks were determined for each construct.

Results from DSC experiments revealed the $T_m$ transition temperatures for the CH2 and Fab domains of the Herceptin (CH2 $T_m1$=68.95° C., Fab $T_m2$=81.43° C.) and NIP228 (CH2 $T_m1$=69.09° C., Fab $T_m2$=74.22° C.) wild-type antibodies (Wakankar, A. A., et al., *Bioconjugate Chemistry*, 2010, 21, 1588-1595; DOI: 10.1021/bc900434c). The NIP228 antibody displayed a third $T_m$ transition temperature for the CH3 domain at 81.92° C. The introduction of the Flexmab technology into these antibodies caused these $T_m$ transition temperatures to reverse, with the Fab domain having a lower $T_m$ transition temperature compared to the CH2 domain (Herceptin-Flexmab Fab $T_m1$=68.21° C., CH2 $T_m1$=81.05° C.; NIP228-Flexmab Fab $T_m1$=66.58° C., CH2 $T_m3$=81.85° C.). As seen with the NIP228 wild-type antibody, we observed a third $T_m$ transition temperature on the NIP228-Flexmab for the CH3 domain ($T_m2$=76.28° C.). As expected, following conjugation of compound 10 to the Herceptin-Flexmab and NIP228-Flexmab antibodies, very minimal changes were observed in the $T_m$ transition temperatures. (Herceptin-Flexmab-10 Fab $T_m1$=67.83° C., CH2 $T_m1$=81.11° C.; NIP228-Flexmab-10 Fab $T_m1$=66.11° C., CH2 $T_m3$=82.19° C.). The third $T_m$ transition temperature for the CH3 domain of NIP228-Flexmab-10 ($T_m2$=78.78° C.) was minimally changed compared to the NIP228-Flexmab.

Example 9—In Vitro Characterization of Herceptin-Flexmab and NIP228-Flexmab Antibodies and ADCs Cell Binding by Flow Cytometry Binding affinities and specificities of the Herceptin-Flexmab and NIP228-Flexmab ADCs were confirmed using flow cytometry. On the study day, SKBR-3 (HER2$^+$) and MCF-7 (HER2$^-$) cells were dissociated from their flask with TrypLE (Life Technologies) trypsin, and resuspended in their respective growth media. Cells were counted on a ViCell cell counter (Beckman Coulter) and brought to a concentration of 1×10$^6$ cells/mL. Cells were transferred in duplicate to wells (5×10$^4$ cells/well) of a 96-well plate (Falcon) and centrifuged at 1200 rpm at 4° C. Pelleted cells were resuspended in 180 μL of flow cytometry buffer (PBS pH 7.2, 2% FBS, on ice) and antibody or ADC was individually added to cells (20 μL of serial dilution: 200 μg/ml-0.01 μg/mL; final concentration 20 μg/mL-0.001 μg/mL). Antibodies and cells were incubated at 4° C. for 1 hour, after which they were washed with flow cytometry buffer and pelleted by centrifugation (2×, 1200 rpm). After the final spin, cell pellets were resuspended in AlexaFluor 647-conjugated anti-human secondary antibody (150 μL, 8 μg/mL, in PBS pH 7.2, 2% FBS) and incubated at 4° C. for 1 hour. Cells were washed with flow cytometry buffer and centrifuged (2×, 1200 rpm), followed by resuspension in 135 μL of flow cytometry buffer. DAPI was added (15 μL from 10×stock, 1 μM final, Sigma Aldrich) to each cell suspension to act as a live/dead stain. Fluorescence data from the cells was collected using a LSRII flow cytometer (Beckton Dickson) and data was analyzed using FlowJo analysis software (Version 9, FlowJo, LLC). Binding curves were generated using GraphPad Prism (Version 6, GraphPad Software, Inc.).

The Herceptin-Flexmab-10 ADC showed high affinity ($EC_{50}$=0.24 μg/mL) and selectivity to the SKBR-3 cell line whereas no binding was observed towards the MCF-7 cell line.

Serum Stability Studies

Mouse serum (Jackson Immunoresearch Labs) was filtered through a 0.2 μm syringe filter (Pall Corporation) into sterile polypropylene tubes and kept on ice. ADC (200 μg) was added to mouse serum to a final concentration of 200 μg/mL and samples were incubated at 37° C. PBS was used as a negative control. Aliquots of 200 μL were taken from each sample at T=0, 24, 72, and 148 hours of incubation. The T=0 time point was placed on dry ice within the first minutes after the addition of ADC to serum. Samples were stored at −80° C. until subjected to affinity capture and analysis by LCMS. Anti-human IgG (Fc-specific) agarose (Sigma Aldrich) was used to affinity capture the ADCs from mouse serum. For each time point, 50 μL of anti-human Fc agarose beads were mixed with 300 μL of PBS and 100 μL of serum sample for 30 min at room temperature under continuous rotation. The beads were washed three times with 1× PBS to remove any unbound serum proteins and the ADCs were eluted using 100 μL IgG elution buffer (Thermo Scientific) and neutralized with 20 μL 1 M Tris pH 8. Individual samples (20 μL) were analyzed by LCMS as described above and the raw data was analyzed using Masshunter software.

After seven days of incubation, LCMS revealed that less than 1% of the compound 10 payload was lost from Herceptin-Flexmab-10. Such good stably in vitro suggests that off-target toxicity could be reduced in vivo.

Cytotoxicity Assays

SKBR-3, MDA-MD-453, and MCF-7 cells were maintained as described above. On the day prior to treatment, cells were dissociated from their flask with TrypLE trypsin, and resuspended in growth media. Cells were counted on a ViCell cell counter and brought to a concentration of $1.0 \times 10^5$ cells/mL in their respective growth media. Cell suspensions (100 μL, $1.0 \times 10^4$ cells/well) were transferred to wells of a white wall, clear bottom 96-well plate (Corning). Cells were allowed to adhere overnight in a 37° C. incubator with 5% $CO_2$. On the treatment day, serial dilutions of ADCs were prepared with a range of 30 μg/mL-1.5 ng/mL and 50 μL of each dilution was added to the wells in triplicate (10 μg/mL-0.5 ng/mL final ADC concentrations, 150 μL total volume/well). Appropriate untreated wells were also added to each plate to serve as controls. On day 5, plates were removed from the incubator and allowed to equilibrate to room temperature. Plates were centrifuged (1300 rpm, 5 mins) and supernatants were aspirated. Media (SKBR-3: McCoy's 5A, MDA-MB-453 and MCF-7: DMEM) without phenol red or FBS was added to each well (50 μL), followed by the addition of CellTiter-Glo® reagent (50 μL). Plates were shaken for 1 hour in the dark at room temperature and luminescence was measured using a Envision™ plate reader (PerkinElmer). Percent viability was calculated as: (Unknown/Avg controls)*100. Experimental data was plotted using GraphPad Prism to generate $IC_{50}$ curves.

After 3 days of incubation on MDA-MB-453 cells (low HER2 expression; $7.7 \times 10^4$ HER2 receptors/cell), Herceptin-Flexmab-10 showed an $IC_{50}$=1.08 nM with ~90% cell viability. After 5 days, Herceptin-Flexmab-10 had an $IC_{50}$=0.0375 nM with ~35% cell viability.

After 3 days of incubation on SKBR-3 cells (high HER2 expression; $1.5 \times 10^6$ HER2 receptors/cell) Herceptin-Flexmab-10 showed an $IC_{50}$=0.229 nM with ~30% cell viability. After 5 days, Herceptin-Flexmab-10 had an $IC_{50}$=0.0355 nM with ~5% cell viability.

Example 10—In Vivo Characterization of Herceptin-Flexmab and NIP228-Flexmab Antibodies and ADCs All studies involved the use of animals were performed humanely under a protocol approved by the MedImmune Institutional Animal Care and Use Committee in a facility accredited by AAALAC International.

Xenografts

NCI-N87 cells ($5 \times 10^6$) in 50% Matrigel were inoculated subcutaneously into 4-6 week old female athymic nude mice (Harlan). When tumors reached 200 mm³, mice were randomized assigned into groups, 5 mice per group. ADCs were administered IV at the indicated doses and dosed at day 5 post cell inoculation. Tumor volumes were measured twice weekly with calipers. The tumor volumes were calculated using the formula ½×L x W² (L=length; W=width). Body weights were measured to assess tolerability of the treatments. The tumor growth and body weight curves were plotted using Prism5 software (GraphPad, La Jolla, Calif.). Tumor volumes are expressed as mean±SEM.

FIG. 1 shows the effect of a single dose at 1.0 mg/kg (♦) compared to non-treatment (●)
  the dose yielded tumor regression followed by tumor stasis for 55 days.

Figure 2:
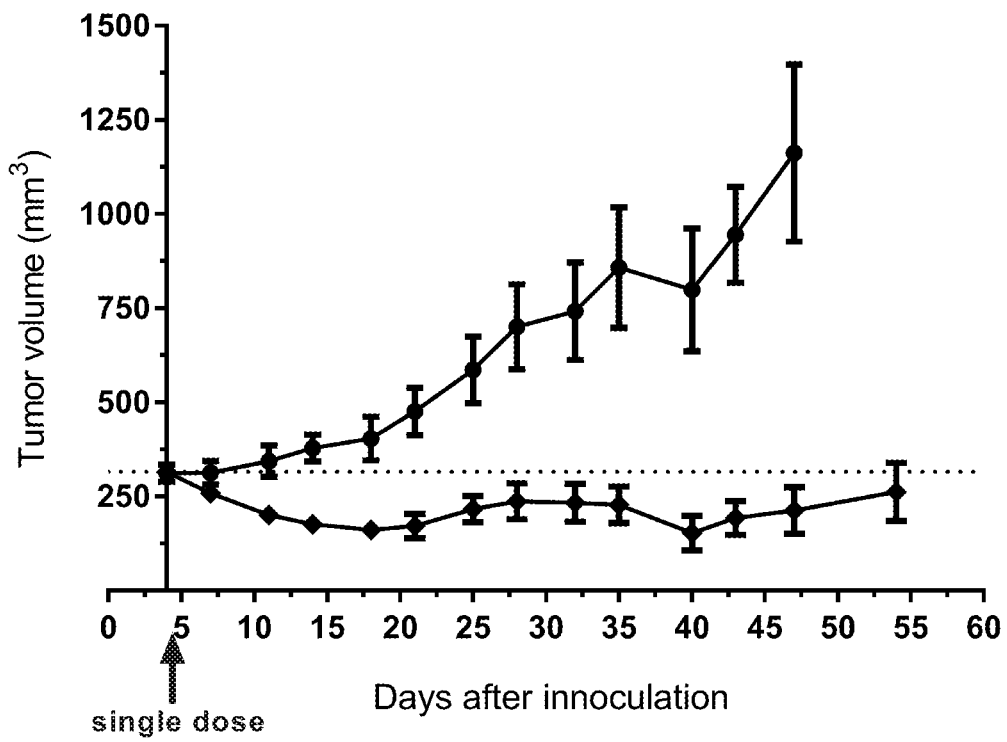
FIG. 2 shows the effect of a lower single dose of the same conjugate of the invention compared to non-treatment in a NCI-N87 xenograft model.

FIG. 2 shows the effect of a single dose at 0.3 mg/kg (♦) compared to non-treatment (●)
  the dose also yielded tumor regression followed by tumor stasis for 55 days.

Toxicity

Male Sprague Dawley rats (8-12 weeks old, 5 per group) were administered a single IV injection (Day 1) of 0.75, 1.5, 3, or 4 mg/kg of Herceptin-Flexmab-10 and rats were evaluated for 21 days. Toxicokinetic (TK) satellite animals (3 per group) were included in each treatment arm to measure plasma concentration of total antibody and ADC. Control rats (5 per group) were administered a single IV injection of vehicle control on Day 1. All main study animals were evaluated for clinical signs, changes in body weight, clinical pathology, gross pathology with organ weights, and microscopic observations. All TK satellite animals were evaluated for clinical signs, changes in body weight, and pharmacokinetic analysis. Hematology and serum chemistry samples were collected and analyzed on Days 8 and 15. Additional samples for coagulation analysis were collected and analyzed on Day 22 only. Blood samples for pharmacokinetic analysis were collected in $K_2$ EDTA tubes prior to dosing and at multiple time points on Days 1, 8, 15, 22. A gross necropsy was performed on all main study animals and a standard list of organs, including brain, lung, liver, kidney, spleen, thymus, testes, heart, and bone, were embedded in paraffin, sectioned, stained with hematoxylin and eosin, and examined microscopically by a board certified veterinary pathologist.

Doses as high as 4 mg/kg of Herceptin-Flexmab-10 were well tolerated.

Therapeutic Index

The Therapeutic Index can be calculated by dividing the maximum tolerated single dose (MTD) of non-targeted ADC in rat, by the minimal effective single dose (MED) of the a targeted ADC. The MED is the single dose necessary to achieve tumour stasis in an in vivo model at 28 days (for NCI-N87 xenograft). Thus for Herceptin-Flexmab-10 the calculated Therapeutic Index is at least 13.3.

Example 11

Herceptin and R347 antibodies engineered to have cysteine inserted between the 239 and 240 positions were produced following the methods described in Dimasi, N., et al., Molecular Pharmaceutics, 2017, 14, 1501-1516 (DOI: 10.1021/acs.molpharmaceut.6b00995).

HerC239i-10 ADC

DTT (100 molar equivalent/antibody, 26.7 micromole) was added to a solution of Herceptin-C239i antibody (40 mg, 266.7 nanomole) in PBS, 1 mM EDTA, pH 7.4 and the final volume was made up to 8 mL. The reduction was carried out at room temperature for 4 hrs with gentle shaking, before DTT was removed by spin filtration using Amicon Ultracell 30 kDa MWCO spin filter. (L)-dehydroascorbic acid (DHAA, 20 molar equivalent/antibody, 5.3 micromole, 106.7 µL at 50 mM in DMSO) was added to the reduced antibody (5 mg/mL, 8 mL) in PBS, 1 mM EDTA, pH 7.4, and the reoxidation took place at room temperature for overnight with gentle shaking. The DHAA was removed by filtration through a 0.22 µm membrane filter, and Compound 10 was added as a DMSO solution (3 molar equivalent/antibody, 0.8 micromole, in 0.9 mL DMSO) to 8.1 mL of the reoxidised antibody (40 mg, 266.7 nanomole) in PBS, 1 mM EDTA, pH 7.4, for a 10% (v/v) final DMSO concentration. The solution was left to react at room temperature for 4 hrs with gentle shaking. The conjugation was quenched by the addition of N-acetyl cysteine (4 micromoles, 40 µL at 100 mM), and purified by hydrophobic interaction chromatography using FPLC and HP-Butyl column (5 mL) with a gradient run of 1 M $(NH4)_2SO_4$, 25 mM Potassium Phosphate pH 6.0, and 25 mM Potassium Phosphate pH 6.0. Fractions containing over 95% DAR1 were pooled, concentrated, buffer exchanged to PBS, pH 7.4, by spin filtration using 15 mL Amicon Ultracell 50 kDa MWCO spin filter, sterile filtered and analysed.

UHPLC analysis on a Shimadzu Prominence system using a Proteomix HIC Butyl-NP5, 5 µm, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of HerC239i-10 ADC at 214 nm shows singly conjugated Compound 10 only, consistent with a drug-per-antibody ratio (DAR) of 1.00 molecules of Compound 10 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a neat sample of HerC239i-10 ADC at 280 nm shows a monomer purity of 99%. UHPLC SEC analysis gives a concentration of final HerC239i-10 ADC at 1.71 mg/mL in 11.1 mL, obtained mass of HerC239i-10 ADC is 18.9 mg (47% yield).

R347C239i-10 ADC

DTT (100 molar equivalent/antibody, 133.3 micromole) was added to a solution of R347-Maia antibody (200 mg, 1.33 micromole) in PBS, 1 mM EDTA, pH 7.4 and the final volume was made up to 40 mL. The reduction was carried out at room temperature for 4 hrs with gentle shaking, before DTT was removed by tangential flow filtration (30 kDa fiber filter). (L)-dehydroascorbic acid (DHAA, 20 molar equivalent/antibody, 26.7 micromole, 533.3 µL at 50 mM in DMSO) was added to the reduced antibody (4 mg/mL, 50 mL) in PBS, 1 mM EDTA, pH 7.4, and the reoxidation took place at room temperature for overnight with gentle shaking. The DHAA was removed by filtration through a 0.22 µm membrane filter, and Compound 10 was added as a DMSO solution (2 molar equivalent/antibody, 2.67 micromole, in 5.6 mL DMSO) to 50.5 mL of the reoxidised antibody (200 mg, 1.33 micromole) in PBS, 1 mM EDTA, pH 7.4, for a 10% (v/v) final DMSO concentration. The solution was left to react at room temperature for 4 hrs with gentle shaking. The conjugation was quenched by the addition of N-acetyl cysteine (6.7 micromoles, 66.7 µL at 100 mM), and purified by hydrophobic interaction chromatography using FPLC and HP-Butyl column (5 mL) with a gradient run of 1 M $(NH4)_2SO_4$, 25 mM Potassium Phosphate pH 6.0, and 25 mM Potassium Phosphate pH 6.0. Fractions containing over 95% DAR1 were pooled, concentrated, buffer exchanged to 25 mM Histidine, 200 mM Sucrose, pH 6.0, by spin filtration using 15 mL Amicon Ultracell 50 kDa MWCO spin filter, sterile filtered and analysed.

UHPLC analysis on a Shimadzu Prominence system using a Proteomix HIC Butyl-NP5, 5 µm, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of R347C239i-10 ADC at 214 nm shows singly conjugated Compound 10 only, consistent with a drug-per-antibody ratio (DAR) of 1.00 molecules of Compound 10 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a neat sample of R347C239i-10 ADC at 280 nm shows a monomer purity of 99%. UHPLC SEC analysis gives a concentration of final R347C239i-10 ADC at 1.72 mg/mL in 55 mL, obtained mass of R347C239i-10 ADC is 94.5 mg (47% yield).

1C1C239i-10 ADC

DTT (100 molar equivalent/antibody, 3.3 micromole) was added to a solution of 1C1-Maia antibody (5 mg, 33.3 nanomole) in PBS, 1 mM EDTA, pH 7.4 and the final volume was made up to 2.5 mL. The reduction was carried out at room temperature for 5 hrs with gentle shaking, before DTT was removed by spin filtration using Amicon Ultracell 30 kDa MWCO spin filter. (L)-dehydroascorbic acid (DHAA, 20 molar equivalent/antibody, 0.67 micromole, 13.3 µL at 50 mM in DMSO) was added to the reduced antibody (2 mg/mL, 2.5 mL) in PBS, 1 mM EDTA, pH 7.4, and the reoxidation took place at room temperature for overnight with gentle shaking. The DHAA was removed by filtration through a 0.22 µm membrane filter, and Compound 10 was added as a DMSO solution (3 molar equivalent/antibody, 0.1 micromole, in 0.27 mL DMSO) to 2.5 mL of the reoxidised antibody (5 mg, 33.3 nanomole) in PBS, 1 mM EDTA, pH 7.4, for a 10% (v/v) final DMSO concentration. The solution was left to react at room temperature for 5 hrs with gentle shaking. The conjugation was quenched by the addition of N-acetyl cysteine (2 micromoles, 39.6 µL at 100 mM), and purified by preparative size exclusion chromatography using FPLC and Superdex 200 26/600 column with PBS pH 7.4 as an elution buffer. Fractions containing over 95% monomers were pooled, concentrated, buffer exchanged to 25 mM Histidine, 200 mM Sucrose, pH 6.0 by spin filtration using 15 mL Amicon Ultracell 50 kDa MWCO spin filter, sterile filtered and analysed.

UHPLC analysis on a Shimadzu Prominence system using a Proteomix HIC Butyl-NP5, 5 µm, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of 1C1C239i-10 ADC at 214 nm shows unconjugated antibody and a mixture of singly conjugated and doubly conjugated Compound 10, consistent with a drug-per-antibody ratio (DAR) of 1.04 molecules of Compound 10 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a neat sample of 1C1C239i-10 ADC at 280 nm shows a monomer purity of 100%. UHPLC SEC analysis gives a concentration of final 1C1C239i-10 ADC at 1.45 mg/mL in 2.3 mL, obtained mass of 1C1C239i-10 ADC is 3.34 mg (67% yield).

HerC239i-11 ADC

DTT (100 molar equivalent/antibody, 3.3 micromole) was added to a solution of Herceptin-Maia antibody (5 mg, 33.3 nanomole) in PBS, 1 mM EDTA, pH 7.4 and the final volume was made up to 2.5 mL. The reduction was carried out at room temperature for 5 hrs with gentle shaking, before DTT was removed by spin filtration using Amicon Ultracell 30 kDa MWCO spin filter. (L)-dehydroascorbic acid (DHAA, 20 molar equivalent/antibody, 0.67 micromole, 13.3 µL at 50 mM in DMSO) was added to the reduced antibody (2 mg/mL, 2.5 mL) in PBS, 1 mM EDTA, pH 7.4, and the reoxidation took place at room temperature for overnight with gentle shaking. The DHAA was removed by filtration through a 0.22 µm membrane filter, and Compound 11 was added as a DMSO solution (1.5 molar equivalent/antibody, 0.05 micromole, in 0.27 mL DMSO) to 2.5 mL of the reoxidised antibody (5 mg, 33.3 nanomole) in PBS, 1 mM EDTA, pH 7.4, for a 10% (v/v) final DMSO concentration. The solution was left to react at room temperature for overnight with gentle shaking. The conjugation was quenched by the addition of N-acetyl cysteine (2 micromoles, 39.6 µL at 100 mM), and purified by preparative size exclusion chromatography using FPLC and Superdex 200 26/600 column with PBS pH 7.4 as an elution buffer. Fractions containing over 95% monomers were pooled, concentrated, buffer exchanged to 25 mM Histidine, 200 mM Sucrose, pH 6.0 by spin filtration using 15 mL Amicon Ultracell 50 kDa MWCO spin filter, sterile filtered and analysed.

UHPLC analysis on a Shimadzu Prominence system using a Proteomix HIC Butyl-NP5, 5 µm, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of HerC239i-11 ADC at 214 nm shows unconjugated antibody and a mixture of singly conjugated and doubly conjugated Compound 11, consistent with a drug-per-antibody ratio (DAR) of 1.10 molecules of Compound 11 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of HerC239i-11 ADC at 280 nm shows a monomer purity of 99%. UHPLC SEC analysis gives a concentration of final HerC239i-11 ADC at 1.29 mg/mL in 4.0 mL, obtained mass of HerC239i-11 ADC is 3.23 mg (65% yield).

1C1C239i-11 ADC

DTT (100 molar equivalent/antibody, 3.3 micromole) was added to a solution of 1C1-Maia antibody (5 mg, 33.3 nanomole) in PBS, 1 mM EDTA, pH 7.4 and the final volume was made up to 2.5 mL. The reduction was carried out at room temperature for 5 hrs with gentle shaking, before DTT was removed by spin filtration using Amicon Ultracell 30 kDa MWCO spin filter. (L)-dehydroascorbic acid (DHAA, 20 molar equivalent/antibody, 0.67 micromole, 13.3 µL at 50 mM in DMSO) was added to the reduced antibody (2 mg/mL, 2.5 mL) in PBS, 1 mM EDTA, pH 7.4, and the reoxidation took place at room temperature for overnight with gentle shaking. The DHAA was removed by filtration through a 0.22 µm membrane filter, and Compound 11 was added as a DMSO solution (1.5 molar equivalent/antibody, 0.05 micromole, in 0.27 mL DMSO) to 2.5 mL of the reoxidised antibody (5 mg, 33.3 nanomole) in PBS, 1 mM EDTA, pH 7.4, for a 10% (v/v) final DMSO concentration. The solution was left to react at room temperature for overnight with gentle shaking. The conjugation was quenched by the addition of N-acetyl cysteine (2 micromoles, 39.6 µL at 100 mM), and purified by preparative size exclusion chromatography using FPLC and Superdex 200 26/600 column with PBS pH 7.4 as an elution buffer. Fractions containing over 95% monomers were pooled, concentrated, buffer exchanged to 25 mM Histidine, 200 mM Sucrose, pH 6.0 by spin filtration using 15 mL Amicon Ultracell 50 kDa MWCO spin filter, sterile filtered and analysed.

UHPLC analysis on a Shimadzu Prominence system using a Proteomix HIC Butyl-NP5, 5 µm, non-porous, 4.6×35 mm (Sepax) column eluting with a gradient of 1.5M ammonium sulphate, 25 mM sodium acetate, pH 7.4 and 25 mM sodium acetate, pH 7.4 with 20% acetonitrile (v/v) on a neat sample of 1C1C239i-11 ADC at 214 nm shows unconjugated antibody and a mixture of singly conjugated and doubly conjugated Compound 11, consistent with a drug-per-antibody ratio (DAR) of 1.05 molecules of Compound 11 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/V) on a sample of 1C1C239i-11 ADC at 280 nm shows a monomer purity of 99%. UHPLC SEC analysis gives a concentration of final 1C1C239i-11 ADC at 1.50 mg/mL in 2.2 mL, obtained mass of 1C1C239i-11 ADC is 3.3 mg (66% yield).

Additional conjugations were carried out to the following antibodies with Compound 10: RSV-C239i; B7H4-E02-C239i; PSMA-C239i; and CDH6-50B-C239i.

Example 12

In Vitro PC3 1C1 Assay

Medium from sub-confluent (80-90% confluency) PC3 cells in a T75 flask was aspirated and the flask rinsed with PBS (about 20 ml) and emptied. Trypsin-EDTA (5 ml) was added, the flask returned to the 37° C. gassed incubator for up to about 5 minutes, then rapped sharply to dislodge and dissociate cells from the plastic. The cell suspension was transferred to a sterile 50 ml screw-top centrifuge tube, diluted with growth medium to a final volume of 15 ml, then centrifuged (400 g for 5 min). The supernatant was aspirated and the pellet re-suspended in 10 ml culture medium. Repeated pipetting may be necessary to produce monodisperse cell suspensions. The cell concentration and viability are measured of trypan blue cell stained cells, using the LUNA II. Cells were diluted to 1500 cells/well, dispensed (50 μl/well) into white 96 well flat bottom plates and incubated overnight before use.

A stock solution (1 ml) of antibody drug conjugate (ADC) (20 μg/ml) was made by dilution of filter-sterilised ADC into cell culture medium. A set of 8×10-fold dilutions of stock ADC were made in a 24 well plate by serial transfer of 100 μl onto 900 μl of cell culture medium. ADC dilution was dispensed (50 μl/well) into 4 replicate wells of the 96-well plate, containing 50 μl cell suspension seeded the previous day. Control wells received 50 μl cell culture medium. The 96-well plate containing cells and ADCs was incubated at 37° C. in a $CO_2$-gassed incubator for 6 days. At the end of the incubation period, plates were equilibrated to room temperature for 30 min before CellTiter-Glo (Promega) was dispensed (100 μl per well) into each well. Plates were placed on an orbital shaker for 2 min before stabilisation at room temperature for 10 min. Well luminescence was measured and percentage cell survival was calculated from the mean luminescence in the 4 ADC-treated wells compared to the mean luminescence in the 4 control untreated wells (100%). $IC_{50}$ was determined from the dose-response data using GraphPad Prism using the non-linear curve fit algorithm: sigmoidal dose response, X is log(concentration). Cell growth medium for PC3 was: F12K with glutamine, 10% (v/v) HyClone™ Fetal Bovine Serum.

| ADC | $EC_{50}$ (μg/ml) |
|---|---|
| 1C1C239i-10 ADC | 0.002247 |
| 1C1C239i-11 ADC | 0.003987 |

In Vitro MTS Assay

The in vitro activity of ADCs was measured in the Her2-expressing cell line NCI-N87 and the Her2 negative cell line MDA-MB-468.

The concentration and viability of cells from a sub-confluent (80-90% confluency) T75 flask are measured by trypan blue staining, and counted using the LUNA-II™ Automated Cell Counter. Cells were diluted to $2×10^5$/ml, dispensed (50 μl per well) into 96-well flat-bottom plates.

A stock solution (1 ml) of antibody drug conjugate (ADC) (20 μg/ml) was made by dilution of filter-sterilised ADC into cell culture medium. A set of 8×10-fold dilutions of stock ADC were made in a 24-well plate by serial transfer of 100 μl into 900 μl of cell culture medium. ADC dilution was dispensed (50 μl per well) into 4 replicate wells of the 96-well plate, containing 50 μl cell suspension seeded the previously. Control wells received 50 μl cell culture medium. The 96-well plate containing cells and ADCs was incubated at 37 C in a CO2-gassed incubator for the exposure time.

At the end of the incubation period, cell viability was measured by MTS assay. MTS (Promega) was dispensed (20 μl per well) into each well and incubated for 4 hours at 37 C in the CO2-gassed incubator. Well absorbance was measured at 490 nm. Percentage cell survival was calculated from the mean absorbance in the 4 ADC-treated wells compared to the mean absorbance in the 4 control untreated wells (100%). $IC_{50}$ was determined from the dose-response data using GraphPad Prism using the non-linear curve fit algorithm: sigmoidal dose-response curve with variable slope.

ADC incubation times were 4 days with MDA-MB-468 and 7 days for NCI-N87. MDA-MB-468 and NCI-N87 were cultured in RPMI 1640 with Glutamax+10% (v/v) HyClone™ Fetal Bovine Serum.

| $EC_{50}$ (μg/ml) | NCI-N87 | MDA-MB-468 |
|---|---|---|
| HerC239i-10 ADC | 0.0002893 | 14.9 |
| HerC239i-11 ADC | 0.0005823 | 11.4 |

Example 13

Mice

Female severe combined immune-deficient mice (Fox Chase SCID®, C.B-17/lcr-Prkdcscid, Charles River) were ten weeks old with a body weight (BW) range of 16.2 to 21.9 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fibre. The mice were housed on irradiated Enricho'Cobs™ Laboratory Animal Bedding in static micro-isolators on a 12-hour light cycle at 20-22° C. (68-72° F.) and 40-60% humidity. CR Discovery Services specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

JIMT-1 Xenografts

Tumour Cell Culture

JIMT-1 human breast carcinoma cells were cultured in Dulbecco's Modified Eagle's Medium (DMEM) containing 10% fetal bovine serum, 2 mM glutamine, 100 units/ml penicillin G sodium, 100 μg/mL streptomycin sulfate, and 25 μg/mL gentamicin. The cells were cultured in tissue culture flasks in a humidified incubator at 37° C., in an atmosphere of 5% $CO_2$ and 95% air.

In Vivo Implantation and Tumour Growth

On the day of implant, JIMT-1 cells were harvested during log phase growth and resuspended in phosphate buffered saline (PBS) at a concentration of $1×10^8$ cells/ml in 50% Matrigel™ (BD Biosciences). Xenografts were initiated by subcutaneously implanting $1×10^7$ JIMT-1 cells (0.1 ml suspension) into the right flank of each test animal. Tumours were monitored as their volumes approached the target range of 100 to 150 mm³ and were measured in two dimensions using calipers. Tumour volume was calculated using the formula:

$$\text{Tumour Volume (mm}^3) = \frac{w^2 \times l}{2}$$

where w=width and l=length, in mm, of the tumour. Tumour weight may be estimated with the assumption that 1 mg is equivalent to 1 mm³ of tumour volume.

Treatment

Fourteen days after tumour implantation, designated as Day 1 of the study, the animals were sorted into groups (n=10) with individual tumour volumes of 75 to 162 mm$^3$ and group mean tumour volumes of 115 to 117 mm$^3$.

HerC239i-10 ADC and HerC239i-SG3249 ADC were administered intravenously in a single dose of 0.3 mg/kg on Day 1. A vehicle-treated group served as tumour growth controls. Tumours were measured twice per week.

HerC239i-SG3249 is a conjugate made from SG32349, as described, for example, in Dimasi, N., et al., Molecular Pharmaceutics, 2017, 14, 1501-1516 (DOI: 10.1021/acs.molpharmaceut.6b00995) and has a DAR of ???

The effect on tumour volume is shown in FIG. 6 where:

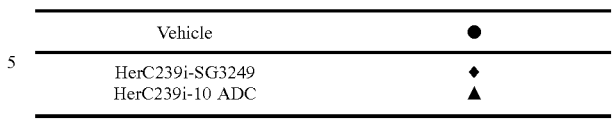

HerC239i-10 ADC demonstrates an equivalent activity to HerC239i-SG3249 ADC, despite only have halve as many PBD dimer warheads.

All documents and other references mentioned above are herein incorporated by reference.

The invention claimed is:

1. A conjugate of formula I:

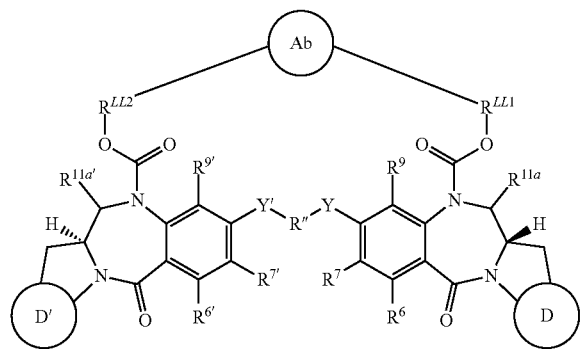

I

Wherein

Ab is a modified antibody having at least one free conjugation site on each heavy chain D represents either group D1 or D2:

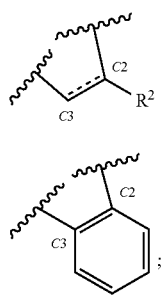

the dotted line indicates the optional presence of a double bond between C2 and C3;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

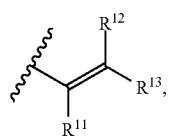

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

wherein one of $R^{15a}$ and $R^{15b}$ is H and the other is selected from:

phenyl, which phenyl is optionally substituted by a group selected from halo, methyl, methoxy; pyridyl; and thiophenyl; and (if)

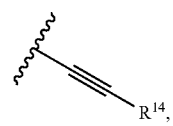

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is selected from H, OH, F, diF and

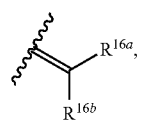

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

D' represents either group D'1 or D'2:

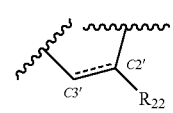

D'1

-continued

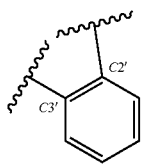
D'2 wherein the dotted line indicates the optional presence of a double bond between C2' and C3';
when there is a double bond present between C2' and C3', $R^{22}$ is selected from the group consisting of:
(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;
(iib) $C_{1-5}$ saturated aliphatic alkyl;
(iic) $C_{3-6}$ saturated cycloalkyl;
(iid)

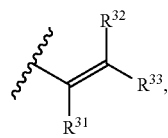

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{22}$ group is no more than 5;
(iie)

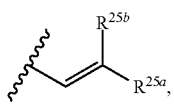

wherein one of $R^{25a}$ and $R^{25b}$ is H and the other is selected from: phenyl, which phenyl is optionally substituted by a group selected from halo, methyl, methoxy; pyridyl; and thiophenyl; and
(iif)

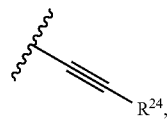

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{22}$ is selected from H, OH, F, diF and

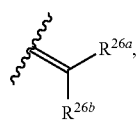

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NRR', nitro, $Me_3Sn$ and halo;
R" is a $C_{3-12}$ alkylene group, which chain may be interrupted by one or more heteroatoms, selected from O, S, $NR^{N2}$, where $R^{N2}$ is H or $C_{1-4}$ alkyl, and/or aromatic rings, selected from benzene or pyridine;
Y and Y' are selected from O, S, or NH;
$R^{11a}$ is selected from OH, $OR^A$, where $R^A$ is $C_{1-4}$ alkyl;
$R^{6'}$, $R^{7'}$, $R^{9'}$ and $R^{11a'}$ are selected from the same groups as $R^6$, $R^7$, $R^9$ and $R^{11a}$ respectively; and
$R^{LL1}$ and $R^{LL2}$ are linkers connected to the antibody at different sites which are independently of formula IIIa':

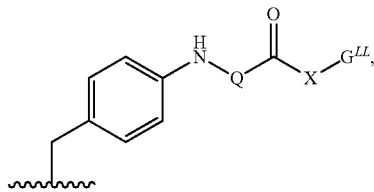
IIIa' wherein
Q is
an amino-acid residue, a dipeptide residue or a tripeptide residue;
X is:

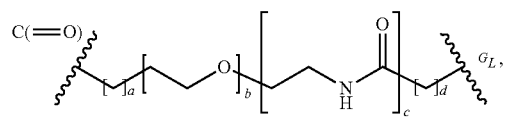

where a=0 to 5, b=0 to 16, c=0 or 1, d=0 to 5;
$G^{LL}$ is selected from:

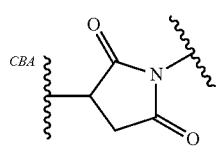
($G^{LL1-1}$)

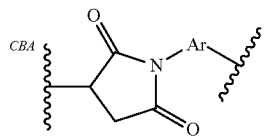
($G^{LL1-2}$)

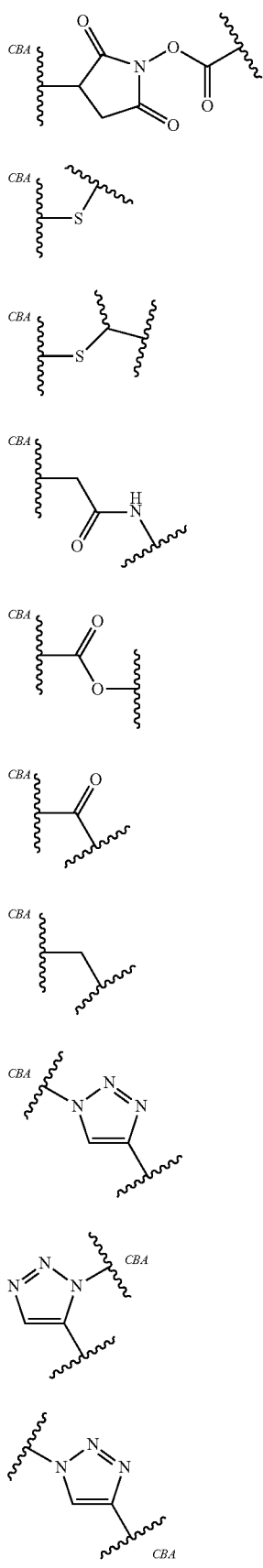
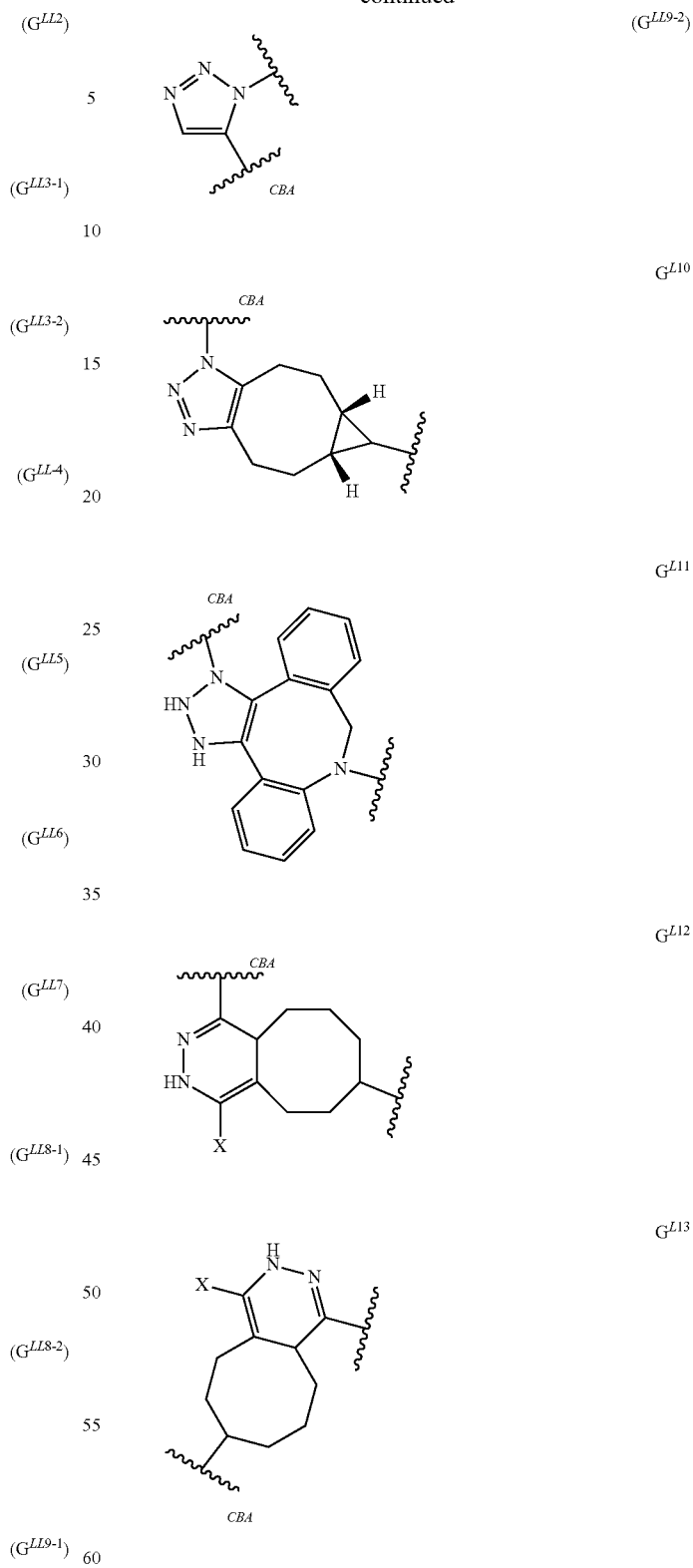
where Ar represents phenylene and X independently represents $C^{1-4}$ alkyl;
where CBA is Ab and represents a cell binding agent which is a modified antibody having at least one free conjugation site on each heavy chain.

2. A conjugate according to claim 1, wherein:
a) both Y and Y' are O; and/or
b) R" is $C_{3-7}$ alkylene or
a group of formula:

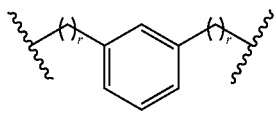

where r is 1 or 2; and/or
c) $R^9$ is H; and/or
d) $R^6$ is H; and/or
e) $R^7$ is selected from H, OH, OR or $C_{1-4}$ alkyloxy group.

3. A conjugate according to claim 1, wherein D is D1, there is a double bond between C2 and C3, and $R^2$ is:
a) a $C_{5-7}$ aryl group wherein $R^2$ optionally bears one to three substituent groups selected from methoxy, ethoxy, fluoro, chloro, cyano, bis-oxy-methylene, methyl-piperazinyl, morpholino and methyl-thiophenyl
b) a $C_{8-10}$ aryl group wherein $R^2$ optionally bears one to three substituent groups selected from methoxy, ethoxy, fluoro, chloro, cyano, bis-oxy-methylene, methyl-piperazinyl, morpholino and methyl-thiophenyl;
c) a $C_{1-5}$ saturated aliphatic alkyl group, optionally wherein $R^2$ is methyl, ethyl or propyl;
d) a group of formula:

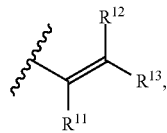

optionally wherein:
i) the total number of carbon atoms in the $R^2$ group is no more than 4;
ii) one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl; or
iii) two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

4. A conjugate according to claim 1, wherein there is a double bond between C2 and C3, and $R^2$ is a $C_{3-6}$ saturated cycloalkyl group, optionally wherein $R^2$ is cyclopropyl.

5. A conjugate according to claim 1, wherein D is D1, there is a double bond between C2 and C3, and $R^2$ is:
a) a group of formula:

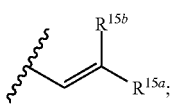

or
b) the group:

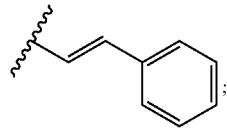 [SMILES: */C=C/c1ccccc1]

or
c) a group of formula:

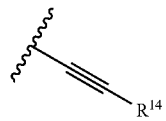

wherein $R^{14}$ is selected from H, methyl, ethyl, ethenyl and ethynyl.

6. A conjugate according to claim 1, wherein D is D1, there is a single bond between C2 and C3, and $R^2$ is:
a) H; or,
b)

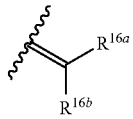

and $R^{16a}$ and $R^{16b}$ are both H; or
c)

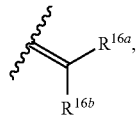

and $R^{16a}$ and $R^{16b}$ are both methyl; or
d)

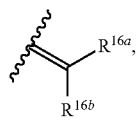

one of $R^{16a}$ and $R^{16b}$ is H, and the other is selected from $C_{1-4}$ saturated alkyl, $C_{2-3}$ alkenyl, which alkyl and alkenyl groups are optionally substituted.

7. A conjugate according to claim 1, wherein D' is D'1, there is a double bond between C2' and C3', and $R^{22}$ is:
a) a $C_{5-7}$ aryl group wherein $R^{22}$ optionally bears one to three substituent groups selected from methoxy, ethoxy, fluoro, chloro, cyano, bis-oxy-methylene, methyl-piperazinyl, morpholino and methyl-thiophenyl; or
b) a $C_{1-5}$ saturated aliphatic alkyl group; or
c) a $C_{3-6}$ saturated cycloalkyl group; or d) a group of formula:

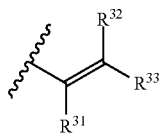

wherein:
  i) the total number of carbon atoms in the $R^{22}$ group is no more than 4; or
  ii) one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl; or
  iii) two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl; or
e) a group of formula:

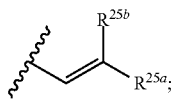

or
f) the group:

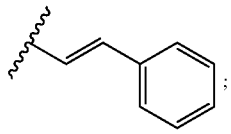

or
g) a group of formula:

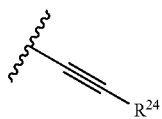

wherein $R^{24}$ is selected from H, methyl, ethyl, ethenyl and ethynyl.

8. A conjugate according to claim 1, wherein D' is D'1, there is a single bond between C2' and C3', and $R^{22}$ is:
  a) H; or
  b)

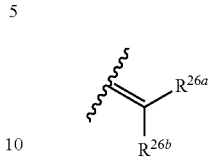

and $R^{26a}$ and $R^{26b}$ are both H; or
  c)

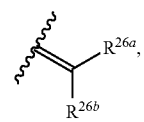

and $R^{26a}$ and $R^{26b}$ are both methyl; or
  d)

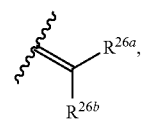

one of $R^{26a}$ and $R^{26b}$ is H, and the other is selected from $C_{1-4}$ saturated alkyl, $C_{2-3}$ alkenyl, which alkyl and alkenyl groups are optionally substituted.

9. A conjugate according to claim 1, wherein $R^{11a}$ is:
  a) OH; or
  b) $OR^A$, where $R^A$ is $C_{1-4}$ alkyl.

10. A conjugate according to claim 1, wherein:
  a) $R^{6'}$ is selected from the same groups as $R^6$, $R^{7'}$ is selected from the same groups as $R^7$, $R^{9'}$ is selected from the same groups as $R^9$, $R^{11a'}$ is selected from the same groups as $R^{11a}$ and Y' is selected from the same groups as Y; and/or
  b) $R^{6'}$ is the same group as $R^6$, $R^{7'}$ is the same group as $R^7$, $R^{9'}$ is the same group as $R^9$, $R^{11a'}$ is the same group as $R^{11a}$ and Y' is the same group as Y; and/or
  c) $R^{22}$ is the same group as $R^2$.

11. A conjugate according to claim 1, which is of formula Ia-1, Ia-2 or Ia-3:

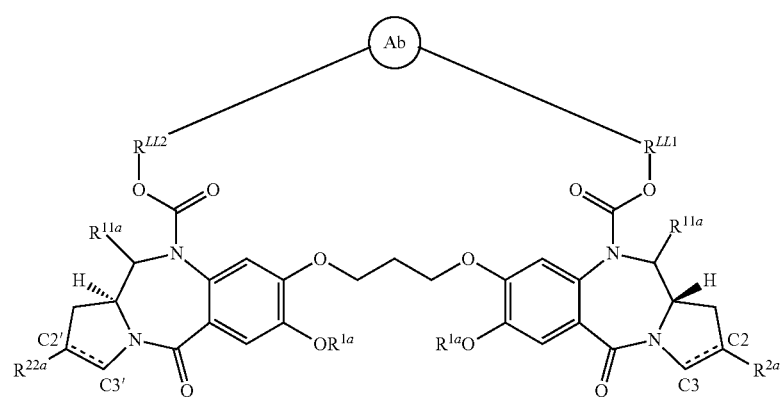

-continued

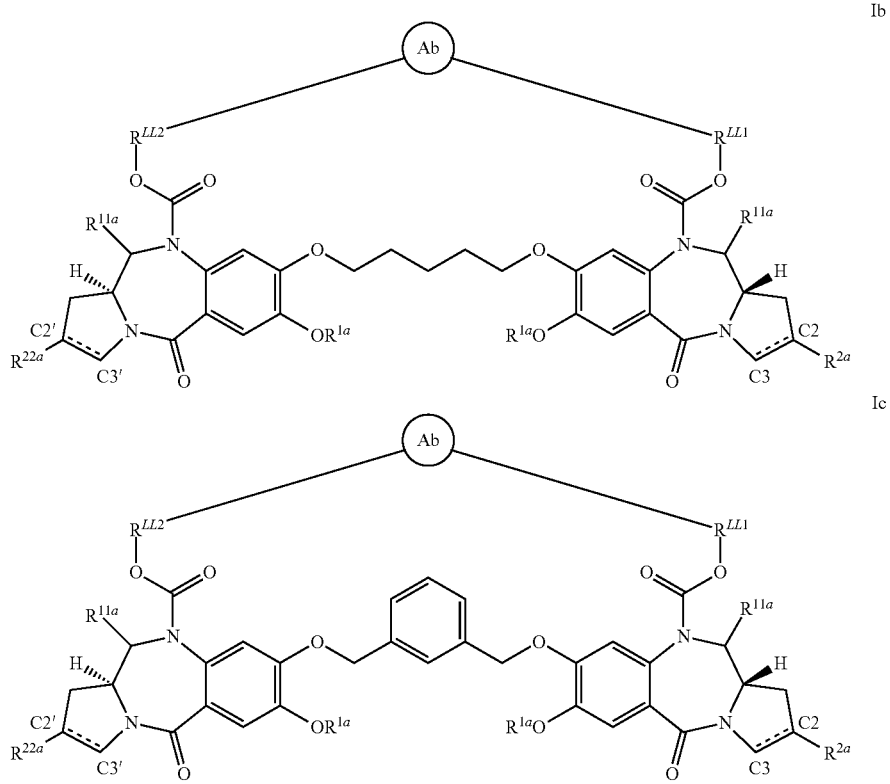

where $R^{2a}$ and $R^{22a}$ are the same and are selected from:

(a) 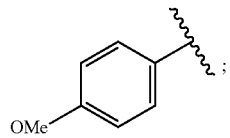

(b) 

(c) 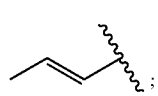

(d) 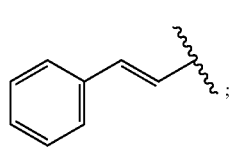

(e) 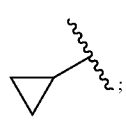

(f) 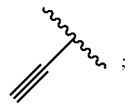

-continued (g) 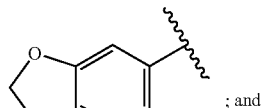

; and (h) 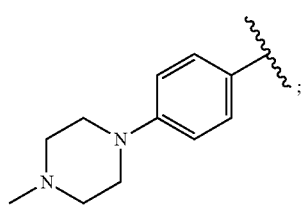

;

$R^{1a}$ is selected from methyl and benzyl;
$R^{LL1}$, $R^{LL2}$ and $R^{11a}$ are as defined in claim 1.

12. A conjugate according to claim 2, wherein $R^{LL1}$ is of formula IIIa', and Q is:
a) an amino acid residue selected from Phe, Lys, Val, Ala, Cit, Leu, Ile, Arg, and Trp; or
b) a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$; or c) a tripeptide residue.
13. A conjugate according to claim 1, wherein $R^{LL1}$ is of formula IIIa' and:
a) a is 0 to 3; and/or
b) b is 0 to 12; and/or
c) d is 0 to 3.
14. A conjugate according to claim 1, wherein $R^{LL1}$ is of formula IIIa' and a is 0, c is 1 and d is 2, and b is from 0 to 8 optionally wherein b is 0, 4 or 8.
15. A conjugate according to claim 1, wherein $R^{LL2}$ is of formula IIIa', and Q is:
a) an amino acid residue selected from Phe, Lys, Val, Ala, Cit, Leu, Ile, Arg, and Trp; or
b) a dipeptide residue selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$; or
c) a tripeptide residue.
16. A conjugate according to claim 1, wherein $R^{LL2}$ is of formula IIIa' and:
a) a is 0 to 3; and/or
b) b is 0 to 12; and/or
c) d is 0 to 3.
17. A conjugate according to claim 1, wherein $R^{LL2}$ is of formula IIIa' and a is 0, c is 1 and d is 2, and b is from 0 to 8.
18. A conjugate according to claim 1 of formula Id:

21. The conjugate according to claim 19, wherein the modified antibody has been modified so that the native interchain cysteine residues have been substituted for amino acid residues lacking thiol groups.
22. The conjugate according to claim 1, wherein the modified antibody comprises at least one additional substitution in each heavy chain of an amino acid residue comprising a reactive group suitable for conjugation to a linker.
23. The conjugate according to claim 22 wherein the position that is substituted is selected from those set forth below:

| Antibody | Isotype | IgG1 | IgG2 | IgG3 | IgG4 |
|---|---|---|---|---|---|
| Position (Kabat EU) and Corresponding Amino Acid | 239 | Ser | Ser | Ser | Ser |
| | 282 | Val | Val | Val | Val |
| | 289 | Thr | Thr | Thr | Thr |
| | 297 | Asn | Asn | Asn | Asn |
| | 312 | Asp | Asp | Asp | Asp |
| | 324 | Ser | Ser | Ser | Ser |
| | 330 | Ala | Ala | Ala | Ser |
| | 335 | Thr | Thr | Thr | Thr |
| | 337 | Ser | Ser | Ser | Ser |
| | 339 | Ala | Thr | Thr | Ala |
| | 356 | Glu | Glu | Glu | Glu |
| | 359 | Thr | Thr | Thr | Thr |
| | 361 | Asn | Asn | Asn | Asn |
| | 383 | Ser | Ser | Ser | Ser |
| | 384 | Asn | Asn | Ser | Asn |
| | 398 | Leu | Leu | Leu | Leu |
| | 400 | Ser | Ser | Ser | Ser |
| | 422 | Val | Val | Ile | Val |
| | 440 | Ser | Ser | Ser | Ser |
| | 442 | Ser | Ser | Ser | Ser |
| SEQ ID NO: | | 1 | 2 | 3 | 4 |

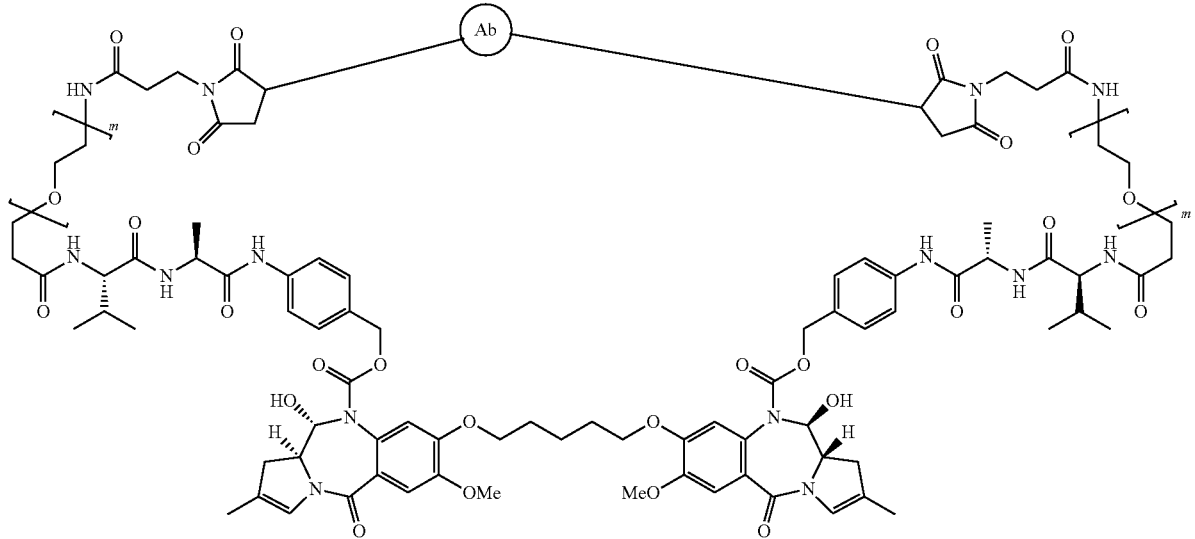

where m is an integer from 2 to 8.
19. The conjugate according to claim 1 wherein the modified antibody having at least one free conjugation site on each heavy chain is an IgG1, IgG2, IgG3 or IgG4 antibody.
20. The conjugate according to claim 19 wherein the modified antibody having at least one free conjugation site on each heavy chain is a human antibody or a humanized antibody.

24. A pharmaceutical composition comprising the conjugate of claim 1, a pharmaceutically acceptable diluent, carrier or excipient.
25. A method of medical treatment comprising administering to a patient the pharmaceutical composition of claim 24.
26. The method of claim 24 wherein the method of medical treatment is for treating cancer.

27. The method of claim 25, wherein the patient is administered a chemotherapeutic agent, in combination with the conjugate.

28. A method of treating a mammal having a proliferative disease, comprising administering an effective amount of a conjugate according to claim 1 or a pharmaceutical composition.

29. A compound of formula II:

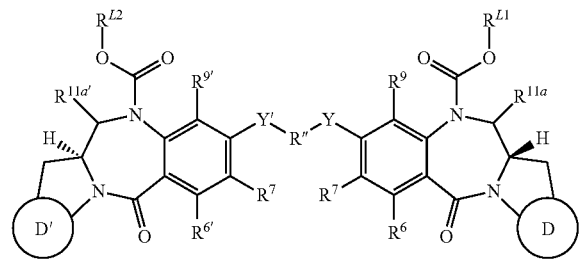

and salts and solvates thereof,

D represents either group D1 or D2:

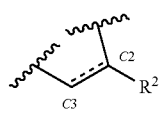

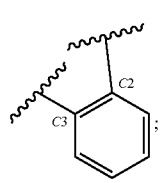

the dotted line indicates the optional presence of a double bond between C2 and C3;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

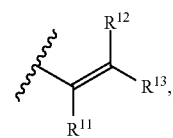

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

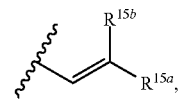

wherein one of $R^{15a}$ and $R^{15b}$ is H and the other is selected from:
phenyl, which phenyl is optionally substituted by a group selected from halo, methyl, methoxy; pyridyl; and thiophenyl; and (if)

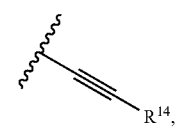

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is selected from H, OH, F, diF and

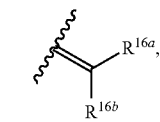

where $R^{16A}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

D' represents either group D'1 or D'2:

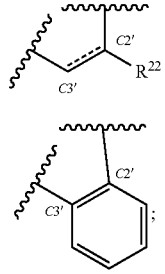

wherein the dotted line indicates the optional presence of a double bond between C2' and C3' when there is a double bond present between C2' and C3', $R^{22}$ is selected from the group consisting of:

(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(iib) $C_{1-5}$ saturated aliphatic alkyl;

(iic) $C_{3-6}$ saturated cycloalkyl;

(iid)

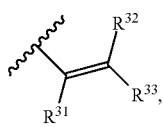

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^{22}$ group is no more than 5;

(iie)

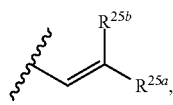

wherein one of $R^{25a}$ and $R^{25b}$ is H and the other is selected from: phenyl, which phenyl is optionally substituted by a group selected from halo, methyl, methoxy; pyridyl; and thiophenyl; and (iif)

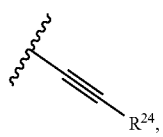

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{22}$ is selected from H, OH, F, diF and

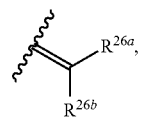

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NRR', nitro, $Me_3Sn$ and halo;
R" is a $C_{3-12}$ alkylene group, which chain may be interrupted by one or more heteroatoms, selected from O, S, $NR^{N2}$, where $R^{N2}$ is H or $C_{1-4}$ alkyl, and/or aromatic rings, selected from benzene or pyridine;
Y and Y' are selected from O, S, or NH;

$R^{11a}$ is selected from OH, $OR^A$, where $R^A$ is $C_{1-4}$ alkyl;
$R^{6'}$, $R^{7'}$, $R^{9'}$ and $R^{11a'}$ are selected from the same groups as $R^6$, $R^7$, $R^9$ and $R^{11a}$ respectively;
$R^{L1}$ and $R^{L2}$ are linkers for connecting to a cell binding agent, which are independently of formula IIIa:

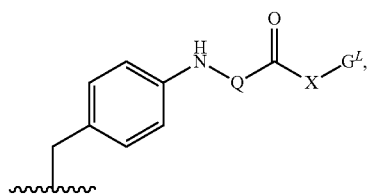

IIIa where Q is an amino-acid residue, a dipeptide residue or a tripeptide residue;
X is:

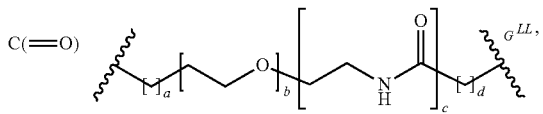

where a=0 to 5, b=0 to 16, c=0 or 1, d=0 to 5;
and $G^L$ is selected from:

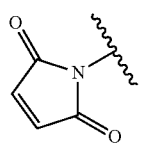

($G^{L1-1}$)

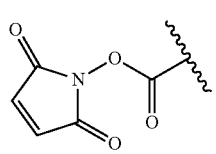

($G^{L2}$)

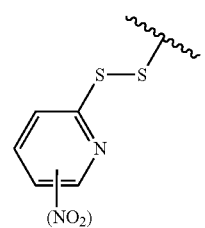

($G^{L3-1}$)

where the $NO_2$ group is optional

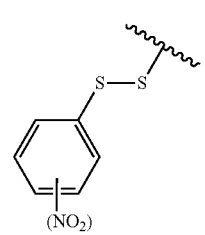

($G^{L3-2}$)

where the $NO_2$ group is optional

-continued
(G<sup>L3-3</sup>)
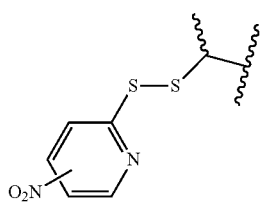
where the NO₂ group is optional
(G<sup>L3-4</sup>)
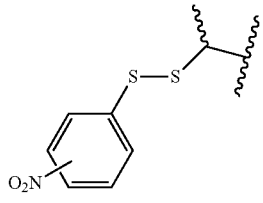
where the NO₂ group is optional
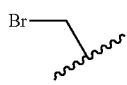
(G<sup>L1-2</sup>)
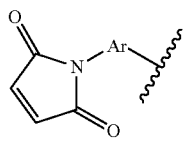
(G<sup>L4</sup>)
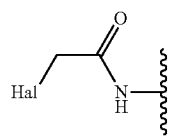
Where Hal = I, Br, Cl
(G<sup>L5</sup>)
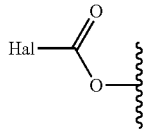
(G<sup>L6</sup>)
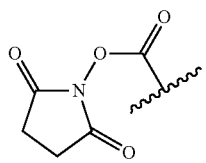
(G<sup>L7</sup>)
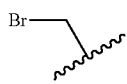
-continued
(G<sup>L8</sup>)
(G<sup>L9</sup>)
(G<sup>L10</sup>)
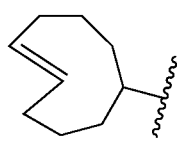
(G<sup>L11</sup>)
(G<sup>L12</sup>)
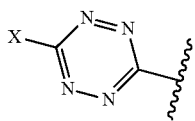
(G<sup>L13</sup>)
where Ar represents phenylene, and X independently represents $C^{1-4}$ alkyl.

30. A compound according to claim 29, wherein the compound is of formula Id:
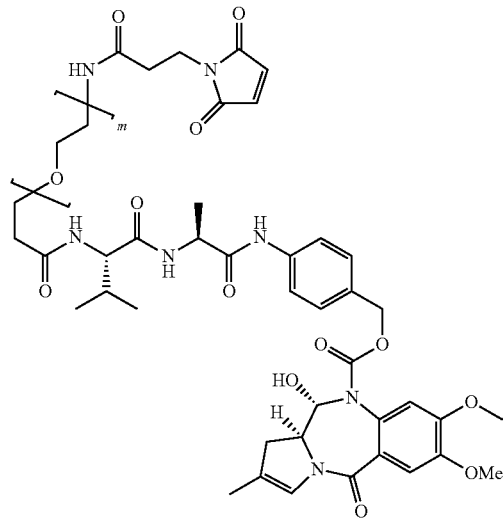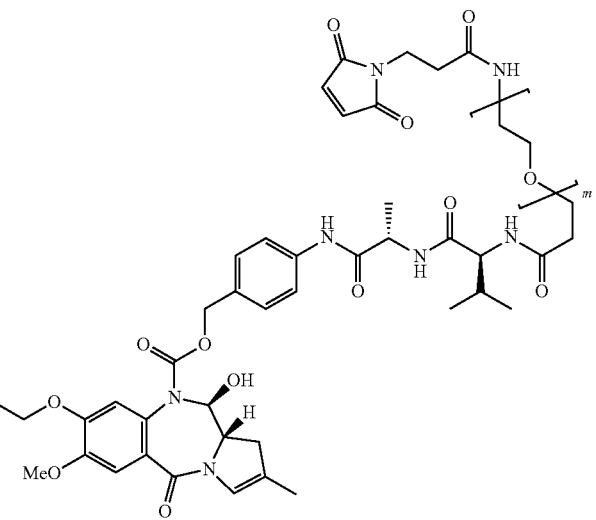
25
where m is an integer from 2 to 8.
31. The conjugate according to claim 22, wherein the additionally substituted amino acid is a cysteine or a non-natural amino acid.
* * * * *

UNITED STATES PATENT AND TRADEMARK OFFICE
CERTIFICATE OF CORRECTION

Page 1 of 5

PATENT NO. : 11,649,250 B2
APPLICATION NO. : 16/639667
DATED : May 16, 2023
INVENTOR(S) : Nazzareno Dimasi et al.

It is certified that error appears in the above-identified patent and that said Letters Patent is hereby corrected as shown below:

On the Title Page

Item (57) the Abstract figure (I) reads:

Whereas it should read:

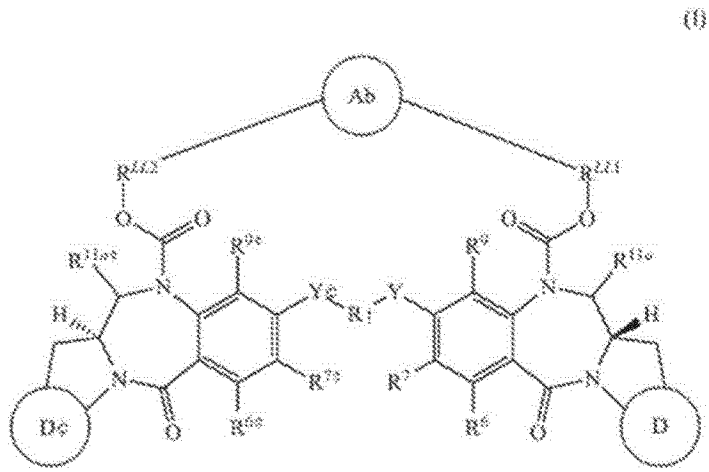

Signed and Sealed this
Twenty-fourth Day of December, 2024

Derrick Brent
*Acting Director of the United States Patent and Trademark Office*

CERTIFICATE OF CORRECTION (continued)
U.S. Pat. No. 11,649,250 B2

In the Claims

Claim 1, Column 110, Lines 62-66 and Column 111, Lines 2-8 read:

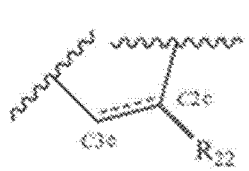 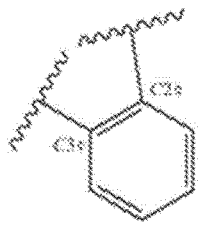

Whereas it should read:

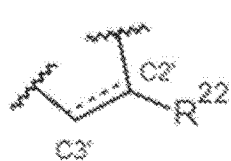 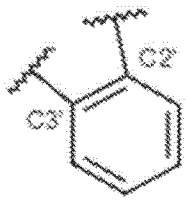

Claim 1, Column 112, Lines 27-35 reads:

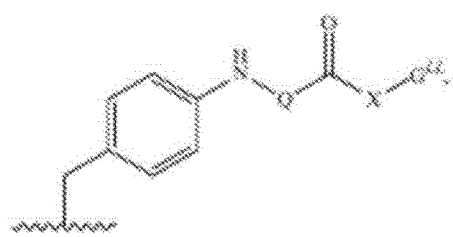

Whereas it should read:

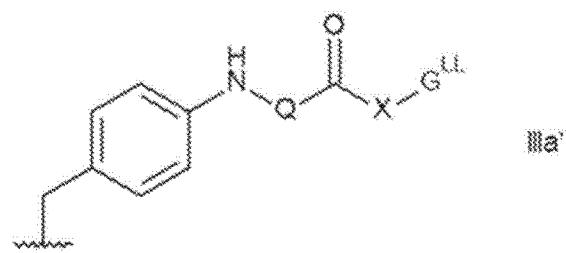

CERTIFICATE OF CORRECTION (continued)
U.S. Pat. No. 11,649,250 B2

Claim 11, Column 119, Lines 1-33 reads:

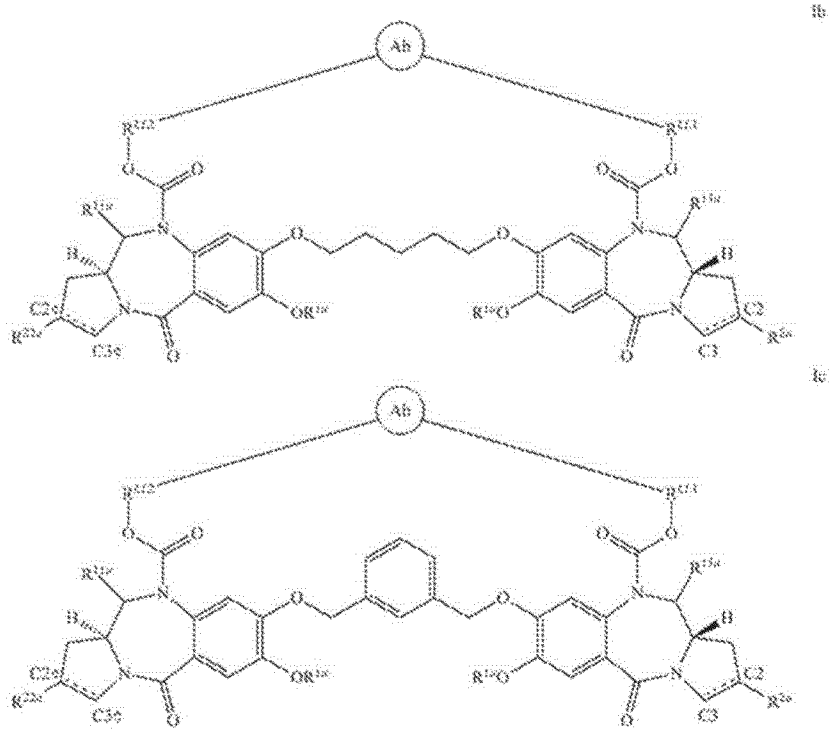

Whereas they should read:

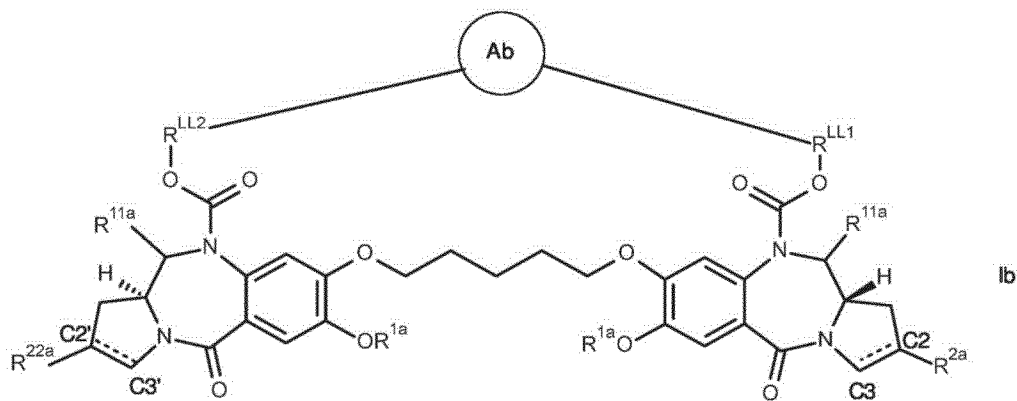

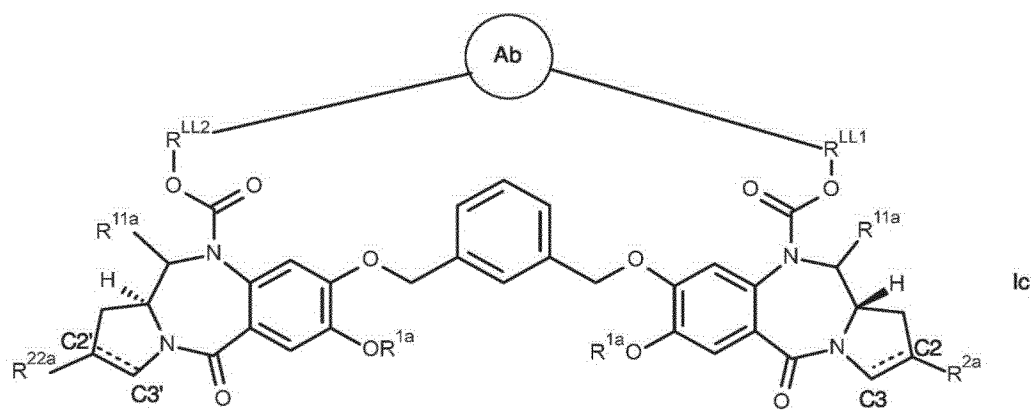

CERTIFICATE OF CORRECTION (continued)
U.S. Pat. No. 11,649,250 B2

Claim 29, Column 123, Lines 12-23 reads:

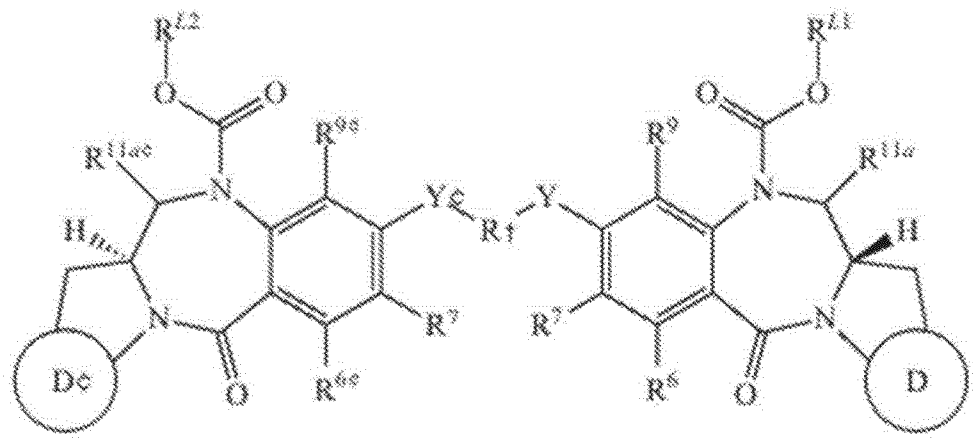

II

Whereas it should read:

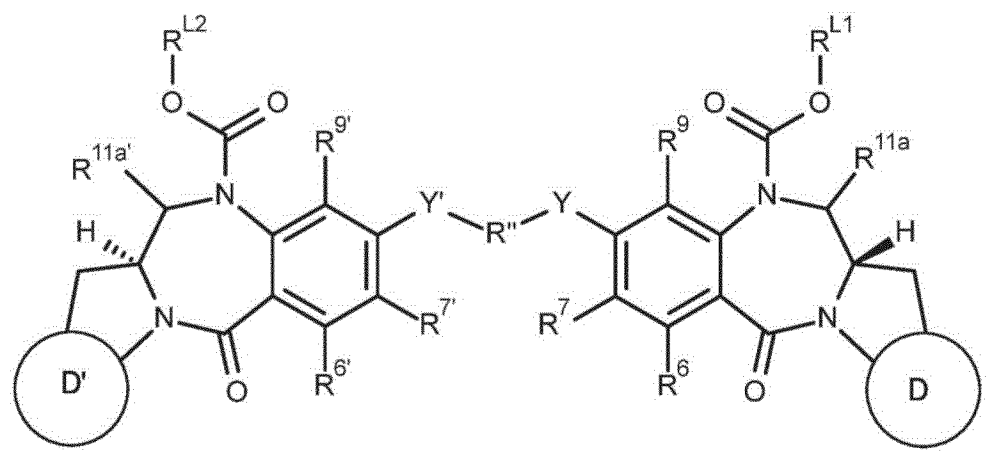

II

Claim 29, Column 124, Lines 46-57 reads:

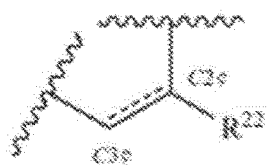

D'1

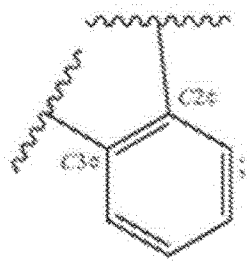

D'2

CERTIFICATE OF CORRECTION (continued)
U.S. Pat. No. 11,649,250 B2

Whereas it should read:

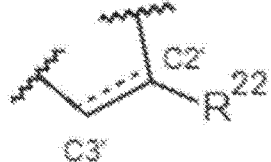 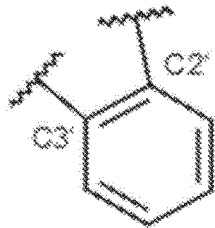

D'1                  D'2

SEQUENCE LISTING

```
<160> NUMBER OF SEQ ID NOS: 4

<210> SEQ ID NO 1
<211> LENGTH: 20
<212> TYPE: PRT
<213> ORGANISM: Artificial sequence
<220> FEATURE:
<223> OTHER INFORMATION: Sythetic

<400> SEQUENCE: 1

Ser Val Thr Asn Asp Ser Ala Thr Ser Ala Glu Thr Asn Ser Asn Leu
1               5                   10                  15

Ser Val Ser Ser
            20

<210> SEQ ID NO 2
<211> LENGTH: 20
<212> TYPE: PRT
<213> ORGANISM: Artificial sequence
<220> FEATURE:
<223> OTHER INFORMATION: Sythetic

<400> SEQUENCE: 2

Ser Val Thr Asn Asp Ser Ala Thr Ser Thr Glu Thr Asn Ser Asn Leu
1               5                   10                  15

Ser Val Ser Ser
            20

<210> SEQ ID NO 3
<211> LENGTH: 20
<212> TYPE: PRT
<213> ORGANISM: Artificial sequence
<220> FEATURE:
<223> OTHER INFORMATION: Sythetic

<400> SEQUENCE: 3

Ser Val Thr Asn Asp Ser Ala Thr Ser Thr Glu Thr Asn Ser Ser Leu
1               5                   10                  15

Ser Ile Ser Ser
            20

<210> SEQ ID NO 4
<211> LENGTH: 20
<212> TYPE: PRT
<213> ORGANISM: Artificial sequence
<220> FEATURE:
<223> OTHER INFORMATION: Sythetic

<400> SEQUENCE: 4

Ser Val Thr Asn Asp Ser Ser Thr Ser Ala Glu Thr Asn Ser Asn Leu
1               5                   10                  15
```

Ser Val Ser Ser
                20